United States Patent
Ricci

(10) Patent No.: US 10,699,326 B2
(45) Date of Patent: *Jun. 30, 2020

(54) USER-ADJUSTED DISPLAY DEVICES AND METHODS OF OPERATING THE SAME

(71) Applicant: NIO USA, Inc., San Jose, CA (US)

(72) Inventor: Christopher P. Ricci, Saratoga, CA (US)

(73) Assignee: NIO USA, Inc., San Jose, CA (US)

( * ) Notice: Subject to any disclaimer, the term of this patent is extended or adjusted under 35 U.S.C. 154(b) by 62 days.

This patent is subject to a terminal disclaimer.

(21) Appl. No.: 15/393,097

(22) Filed: Dec. 28, 2016

(65) Prior Publication Data
US 2018/0012089 A1    Jan. 11, 2018

Related U.S. Application Data

(60) Provisional application No. 62/359,563, filed on Jul. 7, 2016, provisional application No. 62/378,348, filed on Aug. 23, 2016.

(51) Int. Cl.
*G06Q 30/06* (2012.01)
*H04W 4/44* (2018.01)
(Continued)

(52) U.S. Cl.
CPC ........ *G06Q 30/0635* (2013.01); *A61B 5/1171* (2016.02); *A61B 5/1172* (2013.01);
(Continued)

(58) Field of Classification Search
CPC ............ G06K 9/00845; G06K 9/00597; G06F 3/013; G08B 21/06
See application file for complete search history.

(56) References Cited

U.S. PATENT DOCUMENTS 4,361,202 A   11/1982   Minovitch
4,476,954 A   10/1984   Johnson et al.
(Continued)

FOREIGN PATENT DOCUMENTS

CN   1417755   5/2003
CN   1847817   10/2006
(Continued)

OTHER PUBLICATIONS

U.S. Appl. No. 61/567,962, filed Dec. 7, 2011, Baarman et al.
(Continued)

*Primary Examiner* — Vincent Rudolph
*Assistant Examiner* — Raphael Schwartz
(74) *Attorney, Agent, or Firm* — Sheridan Ross P.C.

(57) ABSTRACT

A device includes a microprocessor and a computer readable medium coupled to the microprocessor. The computer readable medium includes instructions stored thereon that cause the microprocessor to receive output from at least one sensor monitoring an interior space of a vehicle and determine, based on the received output, a condition of an occupant in the interior space of the vehicle. The instructions cause the microprocessor to determine, based on the determined condition of the occupant, to alter a first presentation of information displayed to a display device of the vehicle to a second presentation of the information displayed to the display device. The instructions case the microprocessor to render the second presentation of the information to the display device of the vehicle to replace the first presentation of the information displayed to the display device of the vehicle.

17 Claims, 16 Drawing Sheets

(51) Int. Cl.

| | |
|---|---|
| G01C 21/36 | (2006.01) |
| G08G 1/0962 | (2006.01) |
| G08G 1/0967 | (2006.01) |
| G08G 1/0968 | (2006.01) |
| H01Q 1/32 | (2006.01) |
| H04W 12/06 | (2009.01) |
| G06F 21/31 | (2013.01) |
| G06Q 20/10 | (2012.01) |
| G06Q 20/14 | (2012.01) |
| G06Q 20/32 | (2012.01) |
| G06Q 20/40 | (2012.01) |
| H04L 9/32 | (2006.01) |
| B60L 53/14 | (2019.01) |
| B60L 53/12 | (2019.01) |
| B60L 53/80 | (2019.01) |
| B60L 53/65 | (2019.01) |
| B60L 53/66 | (2019.01) |
| G06Q 10/00 | (2012.01) |
| G06Q 30/02 | (2012.01) |
| G07C 5/00 | (2006.01) |
| H04W 4/80 | (2018.01) |
| G06Q 30/00 | (2012.01) |
| G07C 5/08 | (2006.01) |
| A61B 5/1171 | (2016.01) |
| A61B 5/1172 | (2016.01) |
| G07C 5/02 | (2006.01) |
| G07C 9/00 | (2020.01) |
| G06F 3/01 | (2006.01) |
| G06K 9/00 | (2006.01) |
| H02J 7/00 | (2006.01) |
| H01Q 21/30 | (2006.01) |
| H04B 5/00 | (2006.01) |
| B60W 40/08 | (2012.01) |
| B60W 50/08 | (2020.01) |
| G08G 1/017 | (2006.01) |
| G08G 1/00 | (2006.01) |
| G07B 15/06 | (2011.01) |
| G06F 21/62 | (2013.01) |
| H04W 12/02 | (2009.01) |
| G05D 1/00 | (2006.01) |
| G06F 21/32 | (2013.01) |
| B60L 5/24 | (2006.01) |
| B60M 7/00 | (2006.01) |
| G08G 1/16 | (2006.01) |
| B60L 7/10 | (2006.01) |
| B60L 8/00 | (2006.01) |
| B60L 9/00 | (2019.01) |
| G01S 13/931 | (2020.01) |
| B60K 35/00 | (2006.01) |
| B60R 11/00 | (2006.01) |
| B60W 50/14 | (2020.01) |
| B60M 1/00 | (2006.01) |

(52) U.S. Cl.
CPC .......... *A61B 5/1176* (2013.01); *B60L 53/12* (2019.02); *B60L 53/14* (2019.02); *B60L 53/65* (2019.02); *B60L 53/665* (2019.02); *B60L 53/80* (2019.02); *B60W 40/08* (2013.01); *B60W 50/08* (2013.01); *G01C 21/36* (2013.01); *G01C 21/3617* (2013.01); *G01C 21/3697* (2013.01); *G05D 1/0011* (2013.01); *G05D 1/0088* (2013.01); *G06F 3/011* (2013.01); *G06F 21/31* (2013.01); *G06F 21/32* (2013.01); *G06F 21/6245* (2013.01); *G06K 9/00087* (2013.01); *G06K 9/00832* (2013.01); *G06K 9/00845* (2013.01); *G06Q 10/20* (2013.01); *G06Q 20/105* (2013.01); *G06Q 20/108* (2013.01); *G06Q 20/14* (2013.01); *G06Q 20/32* (2013.01); *G06Q 20/3224* (2013.01); *G06Q 20/401* (2013.01); *G06Q 20/405* (2013.01); *G06Q 20/4012* (2013.01); *G06Q 30/012* (2013.01); *G06Q 30/0206* (2013.01); *G06Q 30/0208* (2013.01); *G06Q 30/0601* (2013.01); *G06Q 30/0609* (2013.01); *G06Q 30/0613* (2013.01); *G06Q 30/0625* (2013.01); *G06Q 30/0637* (2013.01); *G07B 15/063* (2013.01); *G07C 5/008* (2013.01); *G07C 5/02* (2013.01); *G07C 5/0808* (2013.01); *G07C 5/0816* (2013.01); *G07C 5/0858* (2013.01); *G07C 9/00563* (2013.01); *G08G 1/017* (2013.01); *G08G 1/0962* (2013.01); *G08G 1/09626* (2013.01); *G08G 1/096775* (2013.01); *G08G 1/096827* (2013.01); *G08G 1/096838* (2013.01); *G08G 1/20* (2013.01); *H01Q 1/325* (2013.01); *H01Q 1/3266* (2013.01); *H01Q 1/3275* (2013.01); *H01Q 1/3283* (2013.01); *H01Q 1/3291* (2013.01); *H01Q 21/30* (2013.01); *H02J 7/0068* (2013.01); *H04B 5/0037* (2013.01); *H04L 9/321* (2013.01); *H04L 9/3226* (2013.01); *H04W 4/44* (2018.02); *H04W 4/80* (2018.02); *H04W 12/02* (2013.01); *H04W 12/06* (2013.01); *A61B 2503/22* (2013.01); *B60K 35/00* (2013.01); *B60K 2370/1537* (2019.05); *B60K 2370/334* (2019.05); *B60L 5/24* (2013.01); *B60L 7/10* (2013.01); *B60L 8/003* (2013.01); *B60L 8/006* (2013.01); *B60L 9/00* (2013.01); *B60L 2240/549* (2013.01); *B60L 2240/70* (2013.01); *B60L 2240/72* (2013.01); *B60L 2270/32* (2013.01); *B60M 1/00* (2013.01); *B60M 7/00* (2013.01); *B60R 2011/0003* (2013.01); *B60R 2011/004* (2013.01); *B60R 2300/30* (2013.01); *B60R 2300/804* (2013.01); *B60R 2325/105* (2013.01); *B60W 2040/0809* (2013.01); *B60W 2050/143* (2013.01); *B60W 2050/146* (2013.01); *B60W 2300/34* (2013.01); *B60W 2540/00* (2013.01); *B60W 2540/21* (2020.02); *B60W 2540/215* (2020.02); *B60Y 2200/91* (2013.01); *B60Y 2200/912* (2013.01); *B60Y 2200/92* (2013.01); *B60Y 2300/60* (2013.01); *B60Y 2302/07* (2013.01); *B60Y 2400/92* (2013.01); *G01S 2013/9316* (2020.01); *G06K 9/00288* (2013.01); *G06K 9/00885* (2013.01); *G08G 1/16* (2013.01); *H04L 2209/80* (2013.01); *H04L 2209/805* (2013.01); *H04L 2209/84* (2013.01); *Y02T 10/7005* (2013.01); *Y02T 10/7072* (2013.01); *Y02T 10/7083* (2013.01); *Y02T 10/7291* (2013.01); *Y02T 90/121* (2013.01); *Y02T 90/122* (2013.01); *Y02T 90/124* (2013.01); *Y02T 90/128* (2013.01); *Y02T 90/14* (2013.01); *Y02T 90/16* (2013.01); *Y02T 90/161* (2013.01); *Y02T 90/163* (2013.01); *Y02T 90/169* (2013.01); *Y04S 30/14* (2013.01)

(56) References Cited

U.S. PATENT DOCUMENTS

| | | |
|---|---|---|
| 4,754,255 A | 6/1988 | Sanders et al. |
| 4,875,391 A | 10/1989 | Leising et al. |

(56) References Cited

U.S. PATENT DOCUMENTS

| | | | |
|---|---|---|---|
| 5,136,498 A | 8/1992 | McLaughlin et al. |
| 5,204,817 A | 4/1993 | Yoshida |
| 5,363,306 A | 11/1994 | Kuwahara et al. |
| 5,508,689 A | 4/1996 | Rado et al. |
| 5,521,815 A | 5/1996 | Rose |
| 5,529,138 A | 6/1996 | Shaw et al. |
| 5,531,122 A | 7/1996 | Chatham et al. |
| 5,572,450 A | 11/1996 | Worthy |
| 5,610,821 A | 3/1997 | Gazis et al. |
| 5,648,769 A | 7/1997 | Sato et al. |
| 5,710,702 A | 1/1998 | Hayashi et al. |
| 5,794,164 A | 8/1998 | Beckert et al. |
| 5,797,134 A | 8/1998 | McMillan et al. |
| 5,812,067 A | 9/1998 | Bergholz et al. |
| 5,825,283 A | 10/1998 | Camhi |
| 5,838,251 A | 11/1998 | Brinkmeyer et al. |
| 5,847,661 A | 12/1998 | Ricci |
| 5,890,080 A | 3/1999 | Coverdill et al. |
| 5,928,294 A | 7/1999 | Zelinkovsky |
| 5,949,345 A | 9/1999 | Heckert et al. |
| 5,983,161 A | 11/1999 | Lemelson et al. |
| 5,986,575 A | 11/1999 | Jones et al. |
| 6,038,426 A | 3/2000 | Williams, Jr. |
| 6,081,756 A | 6/2000 | Mio et al. |
| D429,684 S | 8/2000 | Johnson |
| 6,128,003 A | 10/2000 | Smith et al. |
| 6,141,620 A | 10/2000 | Zyburt et al. |
| 6,148,261 A | 11/2000 | Obradovich et al. |
| 6,152,514 A | 11/2000 | McLellen |
| 6,157,321 A | 12/2000 | Ricci |
| 6,198,996 B1 | 3/2001 | Berstis |
| 6,199,001 B1 | 3/2001 | Ohta et al. |
| 6,202,008 B1 | 3/2001 | Beckert et al. |
| 6,252,544 B1 | 6/2001 | Hoffberg |
| 6,267,428 B1 | 7/2001 | Baldas et al. |
| 6,302,438 B1 | 10/2001 | Stopper, Jr. et al. |
| 6,310,542 B1 | 10/2001 | Gehlot |
| 6,317,058 B1 | 11/2001 | Lemelson et al. |
| 6,339,826 B2 | 1/2002 | Hayes, Jr. et al. |
| 6,356,838 B1 | 3/2002 | Paul |
| 6,388,579 B1 | 5/2002 | Adcox et al. |
| 6,480,224 B1 | 11/2002 | Brown |
| 6,502,022 B1 | 12/2002 | Chastain et al. |
| 6,519,519 B1 | 2/2003 | Stopczynski |
| 6,557,752 B1 | 5/2003 | Yacoob |
| 6,563,910 B2 | 5/2003 | Menard et al. |
| 6,587,739 B1 | 7/2003 | Abrams et al. |
| 6,598,227 B1 | 7/2003 | Berry et al. |
| 6,607,212 B1 | 8/2003 | Reimer et al. |
| 6,617,981 B2 | 9/2003 | Basinger |
| 6,661,345 B1 * | 12/2003 | Bevan ............... G08B 21/06 |
| | | 340/575 |
| 6,662,077 B2 | 12/2003 | Haag |
| 6,675,081 B2 | 1/2004 | Shuman et al. |
| 6,678,747 B2 | 1/2004 | Goossen et al. |
| 6,681,176 B2 | 1/2004 | Funk et al. |
| 6,690,260 B1 | 2/2004 | Ashihara |
| 6,690,940 B1 | 2/2004 | Brown et al. |
| 6,724,920 B1 | 4/2004 | Berenz et al. |
| 6,754,580 B1 | 6/2004 | Ask et al. |
| 6,757,593 B2 | 6/2004 | Mori et al. |
| 6,762,684 B1 | 7/2004 | Camhi |
| 6,765,495 B1 | 7/2004 | Dunning et al. |
| 6,778,888 B2 | 8/2004 | Cataldo et al. |
| 6,782,240 B1 | 8/2004 | Tabe |
| 6,785,531 B2 | 8/2004 | Lepley et al. |
| 6,816,783 B2 | 11/2004 | Hashima et al. |
| 6,820,259 B1 | 11/2004 | Kawamata et al. |
| 6,944,533 B2 | 9/2005 | Obradovich et al. |
| 6,950,022 B2 | 9/2005 | Breed |
| 6,958,707 B1 | 10/2005 | Siegel |
| 6,992,580 B2 | 1/2006 | Kotzin et al. |
| 7,019,641 B1 | 3/2006 | Lakshmanan et al. |
| 7,020,544 B2 | 3/2006 | Shinada et al. |
| 7,021,691 B1 | 4/2006 | Schmidt et al. |
| 7,042,345 B2 | 5/2006 | Ellis |
| 7,047,129 B2 | 5/2006 | Uotani |
| 7,058,898 B2 | 6/2006 | McWalter et al. |
| 7,096,431 B2 | 8/2006 | Tambata et al. |
| 7,142,696 B1 | 11/2006 | Engelsberg et al. |
| 7,164,117 B2 | 1/2007 | Breed et al. |
| 7,187,947 B1 | 3/2007 | White et al. |
| 7,203,598 B1 | 4/2007 | Whitsell |
| 7,233,861 B2 | 6/2007 | Van Buer et al. |
| 7,239,960 B2 | 7/2007 | Yokota et al. |
| 7,277,454 B2 | 10/2007 | Mocek et al. |
| 7,284,769 B2 | 10/2007 | Breed |
| 7,289,645 B2 | 10/2007 | Yamamoto et al. |
| 7,295,921 B2 | 11/2007 | Spencer et al. |
| 7,313,547 B2 | 12/2007 | Mocek et al. |
| 7,333,012 B1 | 2/2008 | Nguyen |
| 7,343,148 B1 | 3/2008 | O'Neil |
| 7,386,376 B2 | 6/2008 | Basir et al. |
| 7,386,799 B1 | 6/2008 | Clanton et al. |
| 7,432,829 B2 | 10/2008 | Poltorak |
| 7,474,264 B2 | 1/2009 | Bolduc et al. |
| 7,493,140 B2 | 2/2009 | Michmerhuizen et al. |
| 7,526,539 B1 | 4/2009 | Hsu |
| 7,548,815 B2 | 6/2009 | Watkins et al. |
| 7,566,083 B2 | 7/2009 | Vitito |
| 7,606,660 B2 | 10/2009 | Diaz et al. |
| 7,606,867 B1 | 10/2009 | Singhal et al. |
| 7,643,913 B2 | 1/2010 | Taki et al. |
| 7,650,234 B2 | 1/2010 | Obradovich et al. |
| 7,671,764 B2 | 3/2010 | Uyeki et al. |
| 7,680,596 B2 | 3/2010 | Uyeki et al. |
| 7,683,771 B1 | 3/2010 | Loeb |
| 7,711,468 B1 | 5/2010 | Levy |
| 7,734,315 B2 | 6/2010 | Rathus et al. |
| 7,748,021 B2 | 6/2010 | Obradovich et al. |
| RE41,449 E | 7/2010 | Krahnstoever et al. |
| 7,791,499 B2 | 9/2010 | Mohan et al. |
| 7,796,190 B2 | 9/2010 | Basso et al. |
| 7,802,832 B2 | 9/2010 | Carnevali |
| 7,821,421 B2 | 10/2010 | Tamir et al. |
| 7,832,762 B2 | 11/2010 | Breed |
| 7,864,073 B2 | 1/2011 | Lee et al. |
| 7,872,591 B2 | 1/2011 | Kane et al. |
| 7,873,471 B2 | 1/2011 | Gieseke |
| 7,881,703 B2 | 2/2011 | Roundtree et al. |
| 7,891,004 B1 | 2/2011 | Gelvin et al. |
| 7,891,719 B2 | 2/2011 | Carnevali |
| 7,899,610 B2 | 3/2011 | McClellan |
| 7,966,678 B2 | 6/2011 | Ten Eyck et al. |
| 7,969,290 B2 | 6/2011 | Waeller et al. |
| 7,969,324 B2 | 6/2011 | Chevion et al. |
| 8,060,631 B2 | 11/2011 | Collart et al. |
| 8,064,925 B1 | 11/2011 | Sun et al. |
| 8,066,313 B2 | 11/2011 | Carnevali |
| 8,098,170 B1 | 1/2012 | Szczerba et al. |
| 8,113,564 B2 | 2/2012 | Carnevali |
| 8,131,419 B2 | 3/2012 | Ampunan et al. |
| 8,157,310 B2 | 4/2012 | Carnevali |
| 8,162,368 B2 | 4/2012 | Carnevali |
| 8,175,802 B2 | 5/2012 | Forstall et al. |
| 8,233,919 B2 | 7/2012 | Haag et al. |
| 8,245,609 B1 | 8/2012 | Greenwald et al. |
| 8,306,514 B1 | 11/2012 | Nunally |
| 8,334,847 B2 | 12/2012 | Tomkins |
| 8,346,233 B2 | 1/2013 | Aaron et al. |
| 8,346,432 B2 | 1/2013 | Van Wiemeersch et al. |
| 8,350,721 B2 | 1/2013 | Carr |
| 8,352,282 B2 | 1/2013 | Jensen et al. |
| 8,369,263 B2 | 2/2013 | Dowling et al. |
| 8,417,449 B1 | 4/2013 | Denise |
| 8,432,260 B2 | 4/2013 | Talty et al. |
| 8,442,389 B2 | 5/2013 | Kashima et al. |
| 8,442,758 B1 | 5/2013 | Rovik et al. |
| 8,467,965 B2 | 6/2013 | Chang |
| 8,497,842 B2 | 7/2013 | Tomkins et al. |
| 8,498,809 B2 | 7/2013 | Bill |
| 8,509,982 B2 | 8/2013 | Montemerlo et al. |
| 8,521,410 B2 | 8/2013 | Mizuno et al. |
| 8,527,143 B2 | 9/2013 | Tan |

(56) References Cited

U.S. PATENT DOCUMENTS

| | | |
|---|---|---|
| 8,527,146 B1 | 9/2013 | Jackson et al. |
| 8,532,574 B2 | 9/2013 | Kirsch |
| 8,543,330 B2 | 9/2013 | Taylor et al. |
| 8,547,340 B2 | 10/2013 | Sizelove et al. |
| 8,548,669 B2 | 10/2013 | Naylor |
| 8,559,183 B1 | 10/2013 | Davis |
| 8,577,600 B1 | 11/2013 | Pierfelice |
| 8,578,279 B2 | 11/2013 | Chen et al. |
| 8,583,292 B2 | 11/2013 | Preston et al. |
| 8,589,073 B2 | 11/2013 | Guha et al. |
| 8,600,611 B2 | 12/2013 | Seize |
| 8,613,385 B1 | 12/2013 | Hulet et al. |
| 8,621,645 B1 | 12/2013 | Spackman |
| 8,624,727 B2 | 1/2014 | Saigh et al. |
| 8,634,984 B2 | 1/2014 | Sumizawa |
| 8,644,165 B2 | 2/2014 | Saarimaki et al. |
| 8,660,735 B2 | 2/2014 | Tengler et al. |
| 8,671,068 B2 | 3/2014 | Harter et al. |
| 8,688,372 B2 | 4/2014 | Bhogal et al. |
| 8,705,527 B1 | 4/2014 | Addepalli et al. |
| 8,706,143 B1 | 4/2014 | Elias |
| 8,718,797 B1 | 5/2014 | Addepalli et al. |
| 8,725,311 B1 | 5/2014 | Breed |
| 8,730,033 B2 | 5/2014 | Yarnold et al. |
| 8,737,986 B2 | 5/2014 | Rhoads et al. |
| 8,761,673 B2 | 6/2014 | Sakata |
| 8,774,842 B2 | 7/2014 | Jones et al. |
| 8,779,947 B2 | 7/2014 | Tengler et al. |
| 8,782,262 B2 | 7/2014 | Collart et al. |
| 8,793,065 B2 | 7/2014 | Seltzer et al. |
| 8,798,918 B2 | 8/2014 | Onishi et al. |
| 8,805,110 B2 | 8/2014 | Rhoads et al. |
| 8,812,171 B2 | 8/2014 | Fillev et al. |
| 8,817,761 B2 | 8/2014 | Gruberman et al. |
| 8,825,031 B2 | 9/2014 | Aaron et al. |
| 8,825,277 B2 | 9/2014 | McClellan et al. |
| 8,825,382 B2 | 9/2014 | Liu |
| 8,826,261 B1 | 9/2014 | Anand et al. |
| 8,838,088 B1 | 9/2014 | Henn et al. |
| 8,862,317 B2 | 10/2014 | Shin et al. |
| 8,965,460 B1 * | 2/2015 | Rao .................. G06F 3/005 455/566 |
| 8,977,408 B1 | 3/2015 | Cazanas et al. |
| 8,994,718 B2 * | 3/2015 | Latta .................. G06F 3/005 345/419 |
| 9,043,016 B2 | 5/2015 | Filippov et al. |
| 9,229,905 B1 | 1/2016 | Penilla et al. |
| 2001/0010516 A1 | 8/2001 | Roh et al. |
| 2001/0015888 A1 | 8/2001 | Shaler et al. |
| 2002/0009978 A1 | 1/2002 | Dukach et al. |
| 2002/0023010 A1 | 2/2002 | Rittmaster et al. |
| 2002/0026278 A1 | 2/2002 | Feldman et al. |
| 2002/0045484 A1 | 4/2002 | Eck et al. |
| 2002/0065046 A1 | 5/2002 | Mankins et al. |
| 2002/0077985 A1 | 6/2002 | Kobata et al. |
| 2002/0095249 A1 | 7/2002 | Lang |
| 2002/0097145 A1 | 7/2002 | Tumey et al. |
| 2002/0103622 A1 | 8/2002 | Burge |
| 2002/0105968 A1 | 8/2002 | Pruzan et al. |
| 2002/0126876 A1 | 9/2002 | Paul et al. |
| 2002/0128774 A1 | 9/2002 | Takezaki et al. |
| 2002/0143461 A1 | 10/2002 | Burns et al. |
| 2002/0143643 A1 | 10/2002 | Catan |
| 2002/0152010 A1 | 10/2002 | Colmenarez et al. |
| 2002/0154217 A1 | 10/2002 | Ikeda |
| 2002/0169551 A1 | 11/2002 | Inoue et al. |
| 2002/0174021 A1 | 11/2002 | Chu et al. |
| 2003/0004624 A1 | 1/2003 | Wilson et al. |
| 2003/0007227 A1 | 1/2003 | Ogino |
| 2003/0055557 A1 | 3/2003 | Dutta et al. |
| 2003/0060937 A1 | 3/2003 | Shinada et al. |
| 2003/0065432 A1 | 4/2003 | Shuman et al. |
| 2003/0101451 A1 | 5/2003 | Bentolila et al. |
| 2003/0109972 A1 | 6/2003 | Tak |
| 2003/0125846 A1 | 7/2003 | Yu et al. |
| 2003/0132666 A1 | 7/2003 | Bond et al. |
| 2003/0149530 A1 | 8/2003 | Stopczynski |
| 2003/0158638 A1 | 8/2003 | Yakes et al. |
| 2003/0182435 A1 | 9/2003 | Redlich et al. |
| 2003/0202683 A1 | 10/2003 | Ma et al. |
| 2003/0204290 A1 | 10/2003 | Sadler et al. |
| 2003/0230443 A1 | 12/2003 | Cramer et al. |
| 2004/0017292 A1 | 1/2004 | Reese et al. |
| 2004/0024502 A1 | 2/2004 | Squires et al. |
| 2004/0036622 A1 | 2/2004 | Dukach et al. |
| 2004/0039500 A1 | 2/2004 | Amendola et al. |
| 2004/0039504 A1 | 2/2004 | Coffee et al. |
| 2004/0068364 A1 | 4/2004 | Zhao et al. |
| 2004/0070920 A1 | 4/2004 | Flueli |
| 2004/0093155 A1 | 5/2004 | Simonds et al. |
| 2004/0117494 A1 | 6/2004 | Mitchell et al. |
| 2004/0128062 A1 | 7/2004 | Ogino et al. |
| 2004/0153356 A1 | 8/2004 | Lockwood et al. |
| 2004/0162019 A1 | 8/2004 | Horita et al. |
| 2004/0180653 A1 | 9/2004 | Royalty |
| 2004/0182574 A1 | 9/2004 | Adnan et al. |
| 2004/0193347 A1 | 9/2004 | Harumoto et al. |
| 2004/0203974 A1 | 10/2004 | Seibel |
| 2004/0204837 A1 | 10/2004 | Singleton |
| 2004/0209594 A1 | 10/2004 | Naboulsi |
| 2004/0217850 A1 | 11/2004 | Perttunen et al. |
| 2004/0225557 A1 | 11/2004 | Phelan et al. |
| 2004/0255123 A1 | 12/2004 | Noyama et al. |
| 2004/0257208 A1 | 12/2004 | Huang et al. |
| 2004/0260470 A1 | 12/2004 | Rast |
| 2005/0012599 A1 | 1/2005 | DeMatteo |
| 2005/0031100 A1 | 2/2005 | Iggulden et al. |
| 2005/0038598 A1 | 2/2005 | Oesterling et al. |
| 2005/0042999 A1 | 2/2005 | Rappaport |
| 2005/0058337 A1 * | 3/2005 | Fujimura ............ G06K 9/00201 382/159 |
| 2005/0065678 A1 | 3/2005 | Smith et al. |
| 2005/0065711 A1 | 3/2005 | Dahlgren et al. |
| 2005/0086051 A1 | 4/2005 | Brulle-Drews |
| 2005/0093717 A1 | 5/2005 | Lilja |
| 2005/0097541 A1 | 5/2005 | Holland |
| 2005/0100192 A1 | 5/2005 | Fujimura et al. |
| 2005/0114864 A1 | 5/2005 | Surace |
| 2005/0122235 A1 | 6/2005 | Teffer et al. |
| 2005/0124211 A1 | 6/2005 | Diessner et al. |
| 2005/0130744 A1 | 6/2005 | Eck et al. |
| 2005/0144156 A1 | 6/2005 | Barber |
| 2005/0149752 A1 | 7/2005 | Johnson et al. |
| 2005/0153760 A1 | 7/2005 | Varley |
| 2005/0159853 A1 | 7/2005 | Takahashi et al. |
| 2005/0159892 A1 | 7/2005 | Chung |
| 2005/0192727 A1 | 9/2005 | Shostak et al. |
| 2005/0197748 A1 | 9/2005 | Holst et al. |
| 2005/0197767 A1 | 9/2005 | Nortrup |
| 2005/0251324 A1 | 11/2005 | Wiener et al. |
| 2005/0261815 A1 | 11/2005 | Cowelchuk et al. |
| 2005/0278093 A1 | 12/2005 | Kameyama |
| 2005/0283284 A1 | 12/2005 | Grenier et al. |
| 2006/0015819 A1 | 1/2006 | Hawkins et al. |
| 2006/0036358 A1 | 2/2006 | Hale et al. |
| 2006/0044119 A1 | 3/2006 | Egelhaaf |
| 2006/0047386 A1 | 3/2006 | Kanevsky et al. |
| 2006/0058948 A1 | 3/2006 | Blass et al. |
| 2006/0059229 A1 | 3/2006 | Bain et al. |
| 2006/0125631 A1 | 6/2006 | Sharony |
| 2006/0130033 A1 | 6/2006 | Stoffels et al. |
| 2006/0142933 A1 | 6/2006 | Feng |
| 2006/0173841 A1 | 8/2006 | Bill |
| 2006/0175403 A1 | 8/2006 | McConnell et al. |
| 2006/0184319 A1 | 8/2006 | Seick et al. |
| 2006/0212909 A1 | 9/2006 | Girard et al. |
| 2006/0241836 A1 | 10/2006 | Kachouh et al. |
| 2006/0243056 A1 | 11/2006 | Sundermeyer et al. |
| 2006/0250272 A1 | 11/2006 | Puamau |
| 2006/0253307 A1 | 11/2006 | Warren et al. |
| 2006/0259210 A1 | 11/2006 | Tanaka et al. |
| 2006/0274829 A1 | 12/2006 | Siemens et al. |
| 2006/0282204 A1 | 12/2006 | Breed |
| 2006/0287807 A1 | 12/2006 | Teffer |

(56) References Cited

U.S. PATENT DOCUMENTS

| | | |
|---|---|---|
| 2006/0287865 A1 | 12/2006 | Cross et al. |
| 2006/0288382 A1 | 12/2006 | Vitito |
| 2006/0290516 A1 | 12/2006 | Muehlsteff et al. |
| 2007/0001831 A1 | 1/2007 | Raz et al. |
| 2007/0002032 A1 | 1/2007 | Powers et al. |
| 2007/0010942 A1 | 1/2007 | Bill |
| 2007/0015485 A1 | 1/2007 | DeBiasio et al. |
| 2007/0028370 A1 | 2/2007 | Seng |
| 2007/0032225 A1 | 2/2007 | Konicek et al. |
| 2007/0057781 A1 | 3/2007 | Breed |
| 2007/0061057 A1 | 3/2007 | Huang et al. |
| 2007/0067614 A1 | 3/2007 | Berry et al. |
| 2007/0069880 A1 | 3/2007 | Best et al. |
| 2007/0083298 A1 | 4/2007 | Pierce et al. |
| 2007/0088488 A1 | 4/2007 | Reeves et al. |
| 2007/0103328 A1 | 5/2007 | Lakshmanan et al. |
| 2007/0115101 A1 | 5/2007 | Creekbaum et al. |
| 2007/0118301 A1 | 5/2007 | Andarawis et al. |
| 2007/0120697 A1 | 5/2007 | Ayoub et al. |
| 2007/0135995 A1 | 6/2007 | Kikuchi et al. |
| 2007/0156317 A1 | 7/2007 | Breed |
| 2007/0182625 A1 | 8/2007 | Kerai et al. |
| 2007/0182816 A1 | 8/2007 | Fox |
| 2007/0185969 A1 | 8/2007 | Davis |
| 2007/0192486 A1 | 8/2007 | Wilson et al. |
| 2007/0194902 A1 | 8/2007 | Blanco et al. |
| 2007/0194944 A1 | 8/2007 | Galera et al. |
| 2007/0195997 A1 | 8/2007 | Paul et al. |
| 2007/0200663 A1 | 8/2007 | White et al. |
| 2007/0208860 A1 | 9/2007 | Zellner et al. |
| 2007/0213090 A1 | 9/2007 | Holmberg |
| 2007/0228826 A1 | 10/2007 | Jordan et al. |
| 2007/0233341 A1 | 10/2007 | Logsdon |
| 2007/0250228 A1 | 10/2007 | Reddy et al. |
| 2007/0257815 A1 | 11/2007 | Gunderson et al. |
| 2007/0276596 A1 | 11/2007 | Solomon et al. |
| 2007/0280505 A1 | 12/2007 | Breed |
| 2008/0005974 A1 | 1/2008 | Delgado Vazquez et al. |
| 2008/0023253 A1 | 1/2008 | Prost-Fin et al. |
| 2008/0027337 A1 | 1/2008 | Dugan et al. |
| 2008/0033635 A1 | 2/2008 | Obradovich et al. |
| 2008/0042824 A1 | 2/2008 | Kates |
| 2008/0051957 A1 | 2/2008 | Breed et al. |
| 2008/0052627 A1 | 2/2008 | Oguchi |
| 2008/0071465 A1 | 3/2008 | Chapman et al. |
| 2008/0082237 A1 | 4/2008 | Breed |
| 2008/0086455 A1 | 4/2008 | Meisels et al. |
| 2008/0090522 A1 | 4/2008 | Oyama |
| 2008/0104227 A1 | 5/2008 | Birnie et al. |
| 2008/0119994 A1 | 5/2008 | Kameyama |
| 2008/0129475 A1 | 6/2008 | Breed et al. |
| 2008/0143085 A1 | 6/2008 | Breed et al. |
| 2008/0147280 A1 | 6/2008 | Breed |
| 2008/0148374 A1 | 6/2008 | Spaur et al. |
| 2008/0154712 A1 | 6/2008 | Wellman |
| 2008/0154957 A1 | 6/2008 | Taylor et al. |
| 2008/0161986 A1 | 7/2008 | Breed |
| 2008/0164985 A1 | 7/2008 | Iketani et al. |
| 2008/0169940 A1 | 7/2008 | Lee et al. |
| 2008/0174451 A1 | 7/2008 | Harrington et al. |
| 2008/0212215 A1 | 9/2008 | Schofield et al. |
| 2008/0216067 A1 | 9/2008 | Villing |
| 2008/0228358 A1 | 9/2008 | Wang et al. |
| 2008/0234919 A1 | 9/2008 | Ritter et al. |
| 2008/0252487 A1 | 10/2008 | McClellan et al. |
| 2008/0253613 A1 | 10/2008 | Jones et al. |
| 2008/0255721 A1 | 10/2008 | Yamada |
| 2008/0255722 A1 | 10/2008 | McClellan et al. |
| 2008/0269958 A1 | 10/2008 | Filev et al. |
| 2008/0281508 A1 | 11/2008 | Fu |
| 2008/0300778 A1 | 12/2008 | Kuznetsov |
| 2008/0305780 A1 | 12/2008 | Williams et al. |
| 2008/0319602 A1 | 12/2008 | McClellan et al. |
| 2009/0006525 A1 | 1/2009 | Moore |
| 2009/0024419 A1 | 1/2009 | McClellan et al. |
| 2009/0037719 A1 | 2/2009 | Sakthikumar et al. |
| 2009/0040026 A1 | 2/2009 | Tanaka |
| 2009/0055178 A1 | 2/2009 | Coon |
| 2009/0082951 A1 | 3/2009 | Graessley |
| 2009/0096597 A1* | 4/2009 | Avery, Jr. ............. G08G 1/0962 340/435 |
| 2009/0099720 A1 | 4/2009 | Elgali |
| 2009/0112393 A1 | 4/2009 | Maten et al. |
| 2009/0112452 A1 | 4/2009 | Buck et al. |
| 2009/0119657 A1 | 5/2009 | Link, II |
| 2009/0125174 A1 | 5/2009 | Delean |
| 2009/0132294 A1 | 5/2009 | Haines |
| 2009/0138336 A1 | 5/2009 | Ashley et al. |
| 2009/0144622 A1 | 6/2009 | Evans et al. |
| 2009/0157312 A1 | 6/2009 | Black et al. |
| 2009/0158200 A1 | 6/2009 | Palahnuk et al. |
| 2009/0180668 A1 | 7/2009 | Jones et al. |
| 2009/0189373 A1 | 7/2009 | Schramm et al. |
| 2009/0189979 A1 | 7/2009 | Smyth |
| 2009/0195370 A1 | 8/2009 | Huffman et al. |
| 2009/0210257 A1 | 8/2009 | Chalfant et al. |
| 2009/0216935 A1 | 8/2009 | Flick |
| 2009/0222200 A1 | 9/2009 | Link et al. |
| 2009/0224931 A1 | 9/2009 | Dietz et al. |
| 2009/0224942 A1 | 9/2009 | Goudy et al. |
| 2009/0234578 A1 | 9/2009 | Newby et al. |
| 2009/0241883 A1 | 10/2009 | Nagoshi et al. |
| 2009/0254446 A1 | 10/2009 | Chernyak |
| 2009/0264849 A1 | 10/2009 | La Croix |
| 2009/0275321 A1 | 11/2009 | Crowe |
| 2009/0278750 A1 | 11/2009 | Man et al. |
| 2009/0278915 A1 | 11/2009 | Kramer et al. |
| 2009/0279839 A1 | 11/2009 | Nakamura et al. |
| 2009/0284359 A1 | 11/2009 | Huang et al. |
| 2009/0287405 A1 | 11/2009 | Liu et al. |
| 2009/0299572 A1 | 12/2009 | Fujikawa et al. |
| 2009/0312998 A1 | 12/2009 | Berckmans et al. |
| 2009/0319181 A1 | 12/2009 | Khosravy et al. |
| 2010/0008053 A1 | 1/2010 | Osternack et al. |
| 2010/0023204 A1 | 1/2010 | Basir et al. |
| 2010/0035620 A1 | 2/2010 | Naden et al. |
| 2010/0036560 A1 | 2/2010 | Wright et al. |
| 2010/0042498 A1 | 2/2010 | Schalk |
| 2010/0052945 A1 | 3/2010 | Breed |
| 2010/0057337 A1 | 3/2010 | Fuchs |
| 2010/0066498 A1 | 3/2010 | Fenton |
| 2010/0069115 A1 | 3/2010 | Liu |
| 2010/0070338 A1 | 3/2010 | Siotia et al. |
| 2010/0077094 A1 | 3/2010 | Howarter et al. |
| 2010/0087987 A1 | 4/2010 | Huang et al. |
| 2010/0090817 A1 | 4/2010 | Yamaguchi et al. |
| 2010/0097178 A1 | 4/2010 | Pisz et al. |
| 2010/0097239 A1 | 4/2010 | Campbell et al. |
| 2010/0097458 A1 | 4/2010 | Zhang et al. |
| 2010/0106344 A1 | 4/2010 | Edwards et al. |
| 2010/0106418 A1 | 4/2010 | Kindo et al. |
| 2010/0118025 A1 | 5/2010 | Smith et al. |
| 2010/0121570 A1 | 5/2010 | Tokue et al. |
| 2010/0121645 A1 | 5/2010 | Seitz et al. |
| 2010/0125387 A1 | 5/2010 | Sehyun et al. |
| 2010/0125405 A1 | 5/2010 | Chae et al. |
| 2010/0125811 A1 | 5/2010 | Moore et al. |
| 2010/0127847 A1 | 5/2010 | Evans et al. |
| 2010/0131300 A1 | 5/2010 | Collopy et al. |
| 2010/0134958 A1 | 6/2010 | Disaverio et al. |
| 2010/0136944 A1 | 6/2010 | Taylor et al. |
| 2010/0137037 A1 | 6/2010 | Basir |
| 2010/0144284 A1 | 6/2010 | Chutorash et al. |
| 2010/0145700 A1 | 6/2010 | Kennewick et al. |
| 2010/0145987 A1 | 6/2010 | Harper et al. |
| 2010/0152976 A1 | 6/2010 | White et al. |
| 2010/0169432 A1 | 7/2010 | Santori et al. |
| 2010/0174474 A1 | 7/2010 | Nagase |
| 2010/0179712 A1 | 7/2010 | Pepitone et al. |
| 2010/0185341 A1 | 7/2010 | Wilson et al. |
| 2010/0188831 A1 | 7/2010 | Ortel |
| 2010/0197359 A1 | 8/2010 | Harris |
| 2010/0202346 A1 | 8/2010 | Sitzes et al. |
| 2010/0211259 A1 | 8/2010 | McClellan |

(56) References Cited

U.S. PATENT DOCUMENTS

| | | |
|---|---|---|
| 2010/0211282 A1 | 8/2010 | Nakata et al. |
| 2010/0211300 A1 | 8/2010 | Jaffe et al. |
| 2010/0211304 A1 | 8/2010 | Hwang et al. |
| 2010/0211441 A1 | 8/2010 | Sprigg et al. |
| 2010/0217458 A1 | 8/2010 | Schweiger et al. |
| 2010/0222939 A1 | 9/2010 | Namburu et al. |
| 2010/0228404 A1 | 9/2010 | Link et al. |
| 2010/0234071 A1 | 9/2010 | Shabtay et al. |
| 2010/0235042 A1 | 9/2010 | Ying |
| 2010/0235744 A1 | 9/2010 | Schultz |
| 2010/0235891 A1 | 9/2010 | Oglesbee et al. |
| 2010/0250071 A1 | 9/2010 | Pala et al. |
| 2010/0253493 A1 | 10/2010 | Szczerba et al. |
| 2010/0253526 A1* | 10/2010 | Szczerba ............ B60K 28/066 340/576 |
| 2010/0256836 A1 | 10/2010 | Mudalige |
| 2010/0265104 A1 | 10/2010 | Zlojutro |
| 2010/0268426 A1 | 10/2010 | Pathak et al. |
| 2010/0274410 A1 | 10/2010 | Tsien et al. |
| 2010/0280751 A1 | 11/2010 | Breed |
| 2010/0287303 A1 | 11/2010 | Smith et al. |
| 2010/0289632 A1 | 11/2010 | Seder et al. |
| 2010/0289643 A1 | 11/2010 | Trundle et al. |
| 2010/0291427 A1 | 11/2010 | Zhou |
| 2010/0295676 A1 | 11/2010 | Khachaturov et al. |
| 2010/0304640 A1 | 12/2010 | Sofman et al. |
| 2010/0305807 A1 | 12/2010 | Basir et al. |
| 2010/0306080 A1 | 12/2010 | Trandal et al. |
| 2010/0306309 A1 | 12/2010 | Santori et al. |
| 2010/0306435 A1 | 12/2010 | Nigoghosian et al. |
| 2010/0315218 A1 | 12/2010 | Cades et al. |
| 2010/0321151 A1 | 12/2010 | Matsuura et al. |
| 2010/0325626 A1 | 12/2010 | Greschler et al. |
| 2010/0332130 A1 | 12/2010 | Shimizu et al. |
| 2011/0015853 A1 | 1/2011 | DeKock et al. |
| 2011/0018736 A1 | 1/2011 | Carr |
| 2011/0021213 A1 | 1/2011 | Carr |
| 2011/0021234 A1 | 1/2011 | Tibbits et al. |
| 2011/0028138 A1 | 2/2011 | Davies-Moore et al. |
| 2011/0035098 A1 | 2/2011 | Goto et al. |
| 2011/0035141 A1 | 2/2011 | Barker et al. |
| 2011/0040438 A1 | 2/2011 | Kluge et al. |
| 2011/0050589 A1 | 3/2011 | Yan et al. |
| 2011/0053506 A1 | 3/2011 | Lemke et al. |
| 2011/0077808 A1 | 3/2011 | Hyde et al. |
| 2011/0078024 A1 | 3/2011 | Messier et al. |
| 2011/0080282 A1 | 4/2011 | Kleve et al. |
| 2011/0082615 A1 | 4/2011 | Small et al. |
| 2011/0084824 A1 | 4/2011 | Tewari et al. |
| 2011/0090078 A1 | 4/2011 | Kim et al. |
| 2011/0092159 A1 | 4/2011 | Park et al. |
| 2011/0093154 A1 | 4/2011 | Moinzadeh et al. |
| 2011/0093158 A1 | 4/2011 | Theisen et al. |
| 2011/0093438 A1 | 4/2011 | Poulsen |
| 2011/0093846 A1 | 4/2011 | Moinzadeh et al. |
| 2011/0105097 A1 | 5/2011 | Tadayon et al. |
| 2011/0106375 A1 | 5/2011 | Sundaram et al. |
| 2011/0112717 A1 | 5/2011 | Resner |
| 2011/0112969 A1 | 5/2011 | Zaid et al. |
| 2011/0117933 A1 | 5/2011 | Andersson |
| 2011/0119344 A1 | 5/2011 | Eustis |
| 2011/0130915 A1 | 6/2011 | Wright et al. |
| 2011/0134749 A1 | 6/2011 | Speks et al. |
| 2011/0137520 A1 | 6/2011 | Rector et al. |
| 2011/0145331 A1 | 6/2011 | Christie et al. |
| 2011/0172873 A1 | 7/2011 | Szwabowski et al. |
| 2011/0175754 A1 | 7/2011 | Karpinsky |
| 2011/0183658 A1 | 7/2011 | Zellner |
| 2011/0187520 A1 | 8/2011 | Filev et al. |
| 2011/0193707 A1 | 8/2011 | Ngo |
| 2011/0193726 A1 | 8/2011 | Szwabowski et al. |
| 2011/0195699 A1 | 8/2011 | Tadayon et al. |
| 2011/0197187 A1 | 8/2011 | Roh |
| 2011/0205047 A1 | 8/2011 | Patel et al. |
| 2011/0209079 A1 | 8/2011 | Tarte et al. |
| 2011/0210867 A1 | 9/2011 | Benedikt |
| 2011/0212717 A1 | 9/2011 | Rhoads et al. |
| 2011/0221656 A1 | 9/2011 | Haddick et al. |
| 2011/0224865 A1 | 9/2011 | Gordon et al. |
| 2011/0224898 A1 | 9/2011 | Scofield et al. |
| 2011/0225527 A1 | 9/2011 | Law et al. |
| 2011/0227757 A1 | 9/2011 | Chen et al. |
| 2011/0231091 A1 | 9/2011 | Gourlay et al. |
| 2011/0234369 A1 | 9/2011 | Cai et al. |
| 2011/0245999 A1 | 10/2011 | Kordonowy |
| 2011/0246210 A1 | 10/2011 | Matsur |
| 2011/0247013 A1 | 10/2011 | Feller et al. |
| 2011/0251734 A1 | 10/2011 | Schepp et al. |
| 2011/0257973 A1 | 10/2011 | Chutorash et al. |
| 2011/0267204 A1 | 11/2011 | Chuang et al. |
| 2011/0267205 A1 | 11/2011 | McClellan et al. |
| 2011/0286676 A1 | 11/2011 | El Dokor |
| 2011/0291886 A1 | 12/2011 | Krieter |
| 2011/0291926 A1 | 12/2011 | Gokturk et al. |
| 2011/0298808 A1 | 12/2011 | Rovik |
| 2011/0301844 A1 | 12/2011 | Aono |
| 2011/0307354 A1 | 12/2011 | Erman et al. |
| 2011/0307570 A1 | 12/2011 | Speks |
| 2011/0309926 A1 | 12/2011 | Eikelenberg et al. |
| 2011/0309953 A1 | 12/2011 | Petite et al. |
| 2011/0313653 A1 | 12/2011 | Lindner |
| 2011/0320089 A1 | 12/2011 | Lewis |
| 2012/0006610 A1 | 1/2012 | Wallace et al. |
| 2012/0010807 A1 | 1/2012 | Zhou |
| 2012/0016581 A1 | 1/2012 | Mochizuki et al. |
| 2012/0029852 A1 | 2/2012 | Goff et al. |
| 2012/0030002 A1 | 2/2012 | Bous et al. |
| 2012/0030512 A1 | 2/2012 | Wadhwa et al. |
| 2012/0038489 A1 | 2/2012 | Goldshmidt |
| 2012/0046822 A1 | 2/2012 | Anderson |
| 2012/0047530 A1 | 2/2012 | Shkedi |
| 2012/0053793 A1 | 3/2012 | Sala et al. |
| 2012/0053888 A1 | 3/2012 | Stahlin et al. |
| 2012/0059789 A1 | 3/2012 | Sakai et al. |
| 2012/0065815 A1 | 3/2012 | Hess |
| 2012/0065834 A1 | 3/2012 | Senart |
| 2012/0068956 A1 | 3/2012 | Jira et al. |
| 2012/0071097 A1 | 3/2012 | Matsushita et al. |
| 2012/0072244 A1 | 3/2012 | Collins et al. |
| 2012/0074770 A1 | 3/2012 | Lee |
| 2012/0083960 A1 | 4/2012 | Zhu et al. |
| 2012/0083971 A1 | 4/2012 | Preston |
| 2012/0084773 A1 | 4/2012 | Lee et al. |
| 2012/0089299 A1 | 4/2012 | Breed |
| 2012/0092251 A1 | 4/2012 | Hashimoto et al. |
| 2012/0101876 A1 | 4/2012 | Truvey et al. |
| 2012/0101914 A1 | 4/2012 | Kumar et al. |
| 2012/0105613 A1 | 5/2012 | Weng et al. |
| 2012/0106114 A1 | 5/2012 | Caron et al. |
| 2012/0109446 A1 | 5/2012 | Yousefi et al. |
| 2012/0109451 A1 | 5/2012 | Tan |
| 2012/0110356 A1 | 5/2012 | Yousefi et al. |
| 2012/0113822 A1 | 5/2012 | Letner |
| 2012/0115446 A1 | 5/2012 | Guatama et al. |
| 2012/0116609 A1 | 5/2012 | Jung et al. |
| 2012/0116678 A1 | 5/2012 | Witmer |
| 2012/0116696 A1 | 5/2012 | Wank |
| 2012/0146766 A1 | 6/2012 | Geisler et al. |
| 2012/0146809 A1 | 6/2012 | Oh et al. |
| 2012/0149341 A1 | 6/2012 | Tadayon et al. |
| 2012/0150651 A1 | 6/2012 | Hoffberg et al. |
| 2012/0155636 A1 | 6/2012 | Muthaiah |
| 2012/0158436 A1 | 6/2012 | Bauer et al. |
| 2012/0173900 A1 | 7/2012 | Diab et al. |
| 2012/0173905 A1 | 7/2012 | Diab et al. |
| 2012/0179325 A1 | 7/2012 | Faenger |
| 2012/0179547 A1 | 7/2012 | Besore et al. |
| 2012/0188876 A1 | 7/2012 | Chow et al. |
| 2012/0197523 A1 | 8/2012 | Kirsch |
| 2012/0197669 A1 | 8/2012 | Kote et al. |
| 2012/0204166 A1 | 8/2012 | Ichihara |
| 2012/0210160 A1 | 8/2012 | Fuhrman |
| 2012/0215375 A1 | 8/2012 | Chang |

(56) References Cited

U.S. PATENT DOCUMENTS

| | | | |
|---|---|---|---|
| 2012/0215403 A1* | 8/2012 | Tengler | B60W 50/12 701/36 |
| 2012/0217928 A1 | 8/2012 | Kulidjian | |
| 2012/0218125 A1 | 8/2012 | Demirdjian et al. | |
| 2012/0226413 A1 | 9/2012 | Chen et al. | |
| 2012/0238286 A1 | 9/2012 | Mallavarapu et al. | |
| 2012/0239242 A1 | 9/2012 | Uehara | |
| 2012/0242510 A1 | 9/2012 | Choi et al. | |
| 2012/0254763 A1 | 10/2012 | Protopapas et al. | |
| 2012/0254804 A1 | 10/2012 | Shema et al. | |
| 2012/0259951 A1 | 10/2012 | Schalk et al. | |
| 2012/0265359 A1 | 10/2012 | Das | |
| 2012/0274459 A1 | 11/2012 | Jaisimha et al. | |
| 2012/0274481 A1 | 11/2012 | Ginsberg et al. | |
| 2012/0284292 A1 | 11/2012 | Rechsteiner et al. | |
| 2012/0289217 A1 | 11/2012 | Reimer et al. | |
| 2012/0289253 A1 | 11/2012 | Haag et al. | |
| 2012/0296567 A1 | 11/2012 | Breed | |
| 2012/0313771 A1 | 12/2012 | Wottlifff, III | |
| 2012/0316720 A1 | 12/2012 | Hyde et al. | |
| 2012/0317561 A1 | 12/2012 | Aslam et al. | |
| 2012/0323413 A1 | 12/2012 | Kedar-Dongarkar et al. | |
| 2012/0327231 A1 | 12/2012 | Cochran et al. | |
| 2013/0005263 A1 | 1/2013 | Sakata | |
| 2013/0005414 A1 | 1/2013 | Bindra et al. | |
| 2013/0013157 A1 | 1/2013 | Kim et al. | |
| 2013/0019252 A1 | 1/2013 | Haase et al. | |
| 2013/0024060 A1 | 1/2013 | Sukkarie et al. | |
| 2013/0030645 A1 | 1/2013 | Divine et al. | |
| 2013/0030811 A1 | 1/2013 | Olleon et al. | |
| 2013/0031540 A1 | 1/2013 | Throop et al. | |
| 2013/0031541 A1 | 1/2013 | Wilks et al. | |
| 2013/0035063 A1 | 2/2013 | Fisk et al. | |
| 2013/0046624 A1 | 2/2013 | Calman | |
| 2013/0050069 A1 | 2/2013 | Ota | |
| 2013/0055096 A1 | 2/2013 | Kim et al. | |
| 2013/0059607 A1 | 3/2013 | Herz et al. | |
| 2013/0063336 A1 | 3/2013 | Sugimoto et al. | |
| 2013/0066512 A1 | 3/2013 | Willard et al. | |
| 2013/0067599 A1 | 3/2013 | Raje et al. | |
| 2013/0075530 A1 | 3/2013 | Shander et al. | |
| 2013/0079964 A1 | 3/2013 | Sukkarie et al. | |
| 2013/0083805 A1 | 4/2013 | Lu et al. | |
| 2013/0085787 A1 | 4/2013 | Gore et al. | |
| 2013/0086164 A1 | 4/2013 | Wheeler et al. | |
| 2013/0099915 A1 | 4/2013 | Prasad et al. | |
| 2013/0103196 A1 | 4/2013 | Monceaux et al. | |
| 2013/0105264 A1 | 5/2013 | Ruth et al. | |
| 2013/0116882 A1 | 5/2013 | Link et al. | |
| 2013/0116915 A1 | 5/2013 | Ferreira et al. | |
| 2013/0134730 A1 | 5/2013 | Ricci | |
| 2013/0135118 A1 | 5/2013 | Ricci | |
| 2013/0138591 A1 | 5/2013 | Ricci | |
| 2013/0138714 A1 | 5/2013 | Ricci | |
| 2013/0139140 A1 | 5/2013 | Rao et al. | |
| 2013/0141247 A1 | 6/2013 | Ricci | |
| 2013/0141252 A1 | 6/2013 | Ricci | |
| 2013/0143495 A1 | 6/2013 | Ricci | |
| 2013/0143546 A1 | 6/2013 | Ricci | |
| 2013/0143601 A1 | 6/2013 | Ricci | |
| 2013/0144459 A1 | 6/2013 | Ricci | |
| 2013/0144460 A1 | 6/2013 | Ricci | |
| 2013/0144461 A1 | 6/2013 | Ricci | |
| 2013/0144462 A1 | 6/2013 | Ricci | |
| 2013/0144463 A1 | 6/2013 | Ricci et al. | |
| 2013/0144469 A1 | 6/2013 | Ricci | |
| 2013/0144470 A1 | 6/2013 | Ricci | |
| 2013/0144474 A1 | 6/2013 | Ricci | |
| 2013/0144486 A1 | 6/2013 | Ricci | |
| 2013/0144520 A1 | 6/2013 | Ricci | |
| 2013/0144657 A1 | 6/2013 | Ricci | |
| 2013/0145065 A1 | 6/2013 | Ricci | |
| 2013/0145279 A1 | 6/2013 | Ricci | |
| 2013/0145297 A1 | 6/2013 | Ricci et al. | |
| 2013/0145360 A1 | 6/2013 | Ricci | |
| 2013/0145401 A1 | 6/2013 | Ricci | |
| 2013/0145482 A1 | 6/2013 | Ricci et al. | |
| 2013/0147638 A1 | 6/2013 | Ricci | |
| 2013/0151031 A1 | 6/2013 | Ricci | |
| 2013/0151065 A1 | 6/2013 | Ricci | |
| 2013/0151088 A1 | 6/2013 | Ricci | |
| 2013/0151288 A1 | 6/2013 | Bowne et al. | |
| 2013/0152003 A1 | 6/2013 | Ricci et al. | |
| 2013/0154298 A1 | 6/2013 | Ricci | |
| 2013/0157640 A1 | 6/2013 | Aycock | |
| 2013/0157647 A1 | 6/2013 | Kolodziej | |
| 2013/0158778 A1 | 6/2013 | Tengler et al. | |
| 2013/0158821 A1 | 6/2013 | Ricci | |
| 2013/0166096 A1 | 6/2013 | Jotanovic | |
| 2013/0166097 A1 | 6/2013 | Ricci | |
| 2013/0166098 A1 | 6/2013 | Lavie et al. | |
| 2013/0166152 A1 | 6/2013 | Butterworth | |
| 2013/0166208 A1 | 6/2013 | Forstall et al. | |
| 2013/0167159 A1 | 6/2013 | Ricci et al. | |
| 2013/0173531 A1 | 7/2013 | Rinearson et al. | |
| 2013/0179689 A1 | 7/2013 | Matsumoto et al. | |
| 2013/0190978 A1 | 7/2013 | Kato et al. | |
| 2013/0194108 A1 | 8/2013 | Lapiotis et al. | |
| 2013/0197753 A1* | 8/2013 | Daly | H04B 1/082 701/36 |
| 2013/0197796 A1 | 8/2013 | Obradovich et al. | |
| 2013/0198031 A1 | 8/2013 | Mitchell et al. | |
| 2013/0198737 A1 | 8/2013 | Ricci | |
| 2013/0198802 A1 | 8/2013 | Ricci | |
| 2013/0200991 A1 | 8/2013 | Ricci et al. | |
| 2013/0203400 A1 | 8/2013 | Ricci | |
| 2013/0204455 A1 | 8/2013 | Chia et al. | |
| 2013/0204457 A1 | 8/2013 | King | |
| 2013/0204466 A1 | 8/2013 | Ricci | |
| 2013/0204484 A1 | 8/2013 | Ricci | |
| 2013/0204493 A1 | 8/2013 | Ricci et al. | |
| 2013/0204943 A1 | 8/2013 | Ricci | |
| 2013/0205026 A1 | 8/2013 | Ricci | |
| 2013/0205412 A1 | 8/2013 | Ricci | |
| 2013/0207794 A1 | 8/2013 | Patel et al. | |
| 2013/0212065 A1 | 8/2013 | Rahnama | |
| 2013/0212659 A1 | 8/2013 | Maher et al. | |
| 2013/0215116 A1 | 8/2013 | Siddique et al. | |
| 2013/0218412 A1 | 8/2013 | Ricci | |
| 2013/0218445 A1 | 8/2013 | Basir | |
| 2013/0219039 A1 | 8/2013 | Ricci | |
| 2013/0226365 A1 | 8/2013 | Brozovich | |
| 2013/0226371 A1 | 8/2013 | Rovik et al. | |
| 2013/0226392 A1 | 8/2013 | Schneider et al. | |
| 2013/0226449 A1 | 8/2013 | Rovik et al. | |
| 2013/0226622 A1 | 8/2013 | Adamson et al. | |
| 2013/0227648 A1 | 8/2013 | Ricci | |
| 2013/0231784 A1 | 9/2013 | Rovik et al. | |
| 2013/0231800 A1 | 9/2013 | Ricci | |
| 2013/0232142 A1 | 9/2013 | Nielsen et al. | |
| 2013/0238165 A1 | 9/2013 | Garrett et al. | |
| 2013/0241720 A1 | 9/2013 | Ricci et al. | |
| 2013/0245882 A1 | 9/2013 | Ricci | |
| 2013/0250933 A1 | 9/2013 | Yousefi et al. | |
| 2013/0261871 A1 | 10/2013 | Hobbs et al. | |
| 2013/0261966 A1 | 10/2013 | Wang et al. | |
| 2013/0265178 A1 | 10/2013 | Tengler et al. | |
| 2013/0274997 A1 | 10/2013 | Chien | |
| 2013/0279111 A1 | 10/2013 | Lee | |
| 2013/0279491 A1 | 10/2013 | Rubin et al. | |
| 2013/0282238 A1 | 10/2013 | Ricci et al. | |
| 2013/0282357 A1 | 10/2013 | Rubin et al. | |
| 2013/0282946 A1 | 10/2013 | Ricci | |
| 2013/0288606 A1 | 10/2013 | Kirsch | |
| 2013/0293364 A1 | 11/2013 | Ricci et al. | |
| 2013/0293452 A1 | 11/2013 | Ricci et al. | |
| 2013/0293480 A1 | 11/2013 | Kritt et al. | |
| 2013/0295901 A1 | 11/2013 | Abramson et al. | |
| 2013/0295908 A1 | 11/2013 | Zeinstra et al. | |
| 2013/0295913 A1 | 11/2013 | Matthews et al. | |
| 2013/0300554 A1 | 11/2013 | Braden | |
| 2013/0301584 A1 | 11/2013 | Addepalli et al. | |
| 2013/0304371 A1 | 11/2013 | Kitatani et al. | |
| 2013/0308265 A1 | 11/2013 | Arnouse | |

(56) References Cited

U.S. PATENT DOCUMENTS

| | | |
|---|---|---|
| 2013/0309977 A1 | 11/2013 | Heines et al. |
| 2013/0311038 A1 | 11/2013 | Kim et al. |
| 2013/0325453 A1 | 12/2013 | Levien et al. |
| 2013/0325568 A1 | 12/2013 | Mangalvedkar et al. |
| 2013/0329372 A1 | 12/2013 | Wilkins |
| 2013/0332023 A1 | 12/2013 | Bertosa et al. |
| 2013/0338914 A1 | 12/2013 | Weiss |
| 2013/0339027 A1 | 12/2013 | Dokor et al. |
| 2013/0345929 A1 | 12/2013 | Bowden et al. |
| 2014/0028542 A1 | 1/2014 | Lovitt et al. |
| 2014/0032014 A1 | 1/2014 | DeBiasio et al. |
| 2014/0054957 A1 | 2/2014 | Bellis |
| 2014/0058672 A1 | 2/2014 | Wansley et al. |
| 2014/0066014 A1 | 3/2014 | Nicholson et al. |
| 2014/0067201 A1 | 3/2014 | Visintainer et al. |
| 2014/0067564 A1 | 3/2014 | Yuan |
| 2014/0070917 A1 | 3/2014 | Protopapas |
| 2014/0081544 A1 | 3/2014 | Fry |
| 2014/0088798 A1 | 3/2014 | Himmelstein |
| 2014/0096068 A1 | 4/2014 | Dewan et al. |
| 2014/0097955 A1 | 4/2014 | Lovitt et al. |
| 2014/0104051 A1 | 4/2014 | Breed |
| 2014/0109075 A1 | 4/2014 | Hoffman et al. |
| 2014/0109080 A1 | 4/2014 | Ricci |
| 2014/0120829 A1 | 5/2014 | Bhamidipati et al. |
| 2014/0121862 A1 | 5/2014 | Zarrella et al. |
| 2014/0125802 A1 | 5/2014 | Heckert et al. |
| 2014/0143839 A1 | 5/2014 | Ricci |
| 2014/0164611 A1 | 6/2014 | Molettiere et al. |
| 2014/0168062 A1 | 6/2014 | Katz et al. |
| 2014/0168436 A1 | 6/2014 | Pedicino |
| 2014/0169621 A1 | 6/2014 | Burr |
| 2014/0171752 A1 | 6/2014 | Park et al. |
| 2014/0172727 A1 | 6/2014 | Abhyanker et al. |
| 2014/0188533 A1 | 7/2014 | Davidson |
| 2014/0195272 A1 | 7/2014 | Sadiq et al. |
| 2014/0198216 A1 | 7/2014 | Zhai et al. |
| 2014/0200737 A1 | 7/2014 | Lortz et al. |
| 2014/0207328 A1 | 7/2014 | Wolf et al. |
| 2014/0220966 A1 | 8/2014 | Muetzel et al. |
| 2014/0222298 A1 | 8/2014 | Gurin |
| 2014/0223384 A1 | 8/2014 | Graumann |
| 2014/0240089 A1 | 8/2014 | Chang |
| 2014/0244078 A1 | 8/2014 | Downey et al. |
| 2014/0244111 A1 | 8/2014 | Gross et al. |
| 2014/0244156 A1 | 8/2014 | Magnusson et al. |
| 2014/0245277 A1 | 8/2014 | Petro et al. |
| 2014/0245278 A1 | 8/2014 | Zellen |
| 2014/0245284 A1 | 8/2014 | Alrabady et al. |
| 2014/0252091 A1 | 9/2014 | Morse et al. |
| 2014/0257627 A1 | 9/2014 | Hagan, Jr. |
| 2014/0267035 A1 | 9/2014 | Schalk et al. |
| 2014/0277936 A1 | 9/2014 | El Dokor et al. |
| 2014/0278070 A1 | 9/2014 | McGavran et al. |
| 2014/0278071 A1 | 9/2014 | San Filippo et al. |
| 2014/0281971 A1 | 9/2014 | Isbell, III et al. |
| 2014/0282161 A1 | 9/2014 | Cash |
| 2014/0282278 A1 | 9/2014 | Anderson et al. |
| 2014/0282470 A1 | 9/2014 | Buga et al. |
| 2014/0282931 A1 | 9/2014 | Protopapas |
| 2014/0292545 A1 | 10/2014 | Nemoto |
| 2014/0292665 A1 | 10/2014 | Lathrop et al. |
| 2014/0303899 A1 | 10/2014 | Fung |
| 2014/0306799 A1 | 10/2014 | Ricci |
| 2014/0306814 A1 | 10/2014 | Ricci |
| 2014/0306817 A1 | 10/2014 | Ricci |
| 2014/0306826 A1 | 10/2014 | Ricci |
| 2014/0306833 A1 | 10/2014 | Ricci |
| 2014/0306834 A1 | 10/2014 | Ricci |
| 2014/0306835 A1 | 10/2014 | Ricci |
| 2014/0307655 A1 | 10/2014 | Ricci |
| 2014/0307724 A1 | 10/2014 | Ricci |
| 2014/0308902 A1 | 10/2014 | Ricci |
| 2014/0309789 A1 | 10/2014 | Ricci |
| 2014/0309790 A1 | 10/2014 | Ricci |
| 2014/0309804 A1 | 10/2014 | Ricci |
| 2014/0309805 A1 | 10/2014 | Ricci |
| 2014/0309806 A1 | 10/2014 | Ricci |
| 2014/0309813 A1 | 10/2014 | Ricci |
| 2014/0309814 A1 | 10/2014 | Ricci et al. |
| 2014/0309815 A1 | 10/2014 | Ricci et al. |
| 2014/0309838 A1 | 10/2014 | Ricci |
| 2014/0309839 A1 | 10/2014 | Ricci et al. |
| 2014/0309847 A1 | 10/2014 | Ricci |
| 2014/0309849 A1 | 10/2014 | Ricci |
| 2014/0309852 A1 | 10/2014 | Ricci |
| 2014/0309853 A1 | 10/2014 | Ricci |
| 2014/0309862 A1 | 10/2014 | Ricci |
| 2014/0309863 A1 | 10/2014 | Ricci |
| 2014/0309864 A1 | 10/2014 | Ricci |
| 2014/0309865 A1 | 10/2014 | Ricci |
| 2014/0309866 A1 | 10/2014 | Ricci |
| 2014/0309867 A1 | 10/2014 | Ricci |
| 2014/0309868 A1 | 10/2014 | Ricci |
| 2014/0309869 A1 | 10/2014 | Ricci |
| 2014/0309870 A1 | 10/2014 | Ricci et al. |
| 2014/0309871 A1 | 10/2014 | Ricci |
| 2014/0309872 A1 | 10/2014 | Ricci |
| 2014/0309873 A1 | 10/2014 | Ricci |
| 2014/0309874 A1 | 10/2014 | Ricci |
| 2014/0309875 A1 | 10/2014 | Ricci |
| 2014/0309876 A1 | 10/2014 | Ricci |
| 2014/0309877 A1 | 10/2014 | Ricci |
| 2014/0309878 A1 | 10/2014 | Ricci |
| 2014/0309879 A1 | 10/2014 | Ricci |
| 2014/0309880 A1 | 10/2014 | Ricci |
| 2014/0309885 A1 | 10/2014 | Ricci |
| 2014/0309886 A1 | 10/2014 | Ricci |
| 2014/0309891 A1 | 10/2014 | Ricci |
| 2014/0309892 A1 | 10/2014 | Ricci |
| 2014/0309893 A1 | 10/2014 | Ricci |
| 2014/0309913 A1 | 10/2014 | Ricci et al. |
| 2014/0309919 A1 | 10/2014 | Ricci |
| 2014/0309920 A1 | 10/2014 | Ricci |
| 2014/0309921 A1 | 10/2014 | Ricci et al. |
| 2014/0309922 A1 | 10/2014 | Ricci |
| 2014/0309923 A1 | 10/2014 | Ricci |
| 2014/0309927 A1 | 10/2014 | Ricci |
| 2014/0309929 A1 | 10/2014 | Ricci |
| 2014/0309930 A1 | 10/2014 | Ricci |
| 2014/0309934 A1 | 10/2014 | Ricci |
| 2014/0309935 A1 | 10/2014 | Ricci |
| 2014/0309982 A1 | 10/2014 | Ricci |
| 2014/0310031 A1 | 10/2014 | Ricci |
| 2014/0310075 A1 | 10/2014 | Ricci |
| 2014/0310103 A1 | 10/2014 | Ricci |
| 2014/0310186 A1 | 10/2014 | Ricci |
| 2014/0310277 A1 | 10/2014 | Ricci |
| 2014/0310379 A1 | 10/2014 | Ricci et al. |
| 2014/0310594 A1 | 10/2014 | Ricci et al. |
| 2014/0310610 A1 | 10/2014 | Ricci |
| 2014/0310702 A1 | 10/2014 | Ricci et al. |
| 2014/0310739 A1 | 10/2014 | Ricci et al. |
| 2014/0310788 A1 | 10/2014 | Ricci |
| 2014/0322676 A1 | 10/2014 | Raman |
| 2014/0347207 A1 | 11/2014 | Zeng et al. |
| 2014/0347265 A1 | 11/2014 | Allen et al. |
| 2015/0007155 A1 | 1/2015 | Hoffman et al. |
| 2015/0012186 A1 | 1/2015 | Horseman |
| 2015/0032366 A1 | 1/2015 | Man et al. |
| 2015/0032670 A1 | 1/2015 | Brazell |
| 2015/0057839 A1 | 2/2015 | Chang et al. |
| 2015/0061895 A1 | 3/2015 | Ricci |
| 2015/0081133 A1 | 3/2015 | Schulz |
| 2015/0081167 A1 | 3/2015 | Pisz et al. |
| 2015/0088423 A1 | 3/2015 | Tuukkanen |
| 2015/0088515 A1 | 3/2015 | Beaumont et al. |
| 2015/0094544 A1* | 4/2015 | Spolin ............ A61B 5/7275 600/301 |
| 2015/0116200 A1 | 4/2015 | Kurosawa et al. |
| 2015/0158499 A1 | 6/2015 | Koravadi |
| 2015/0178034 A1 | 6/2015 | Penilla et al. |
| 2015/0178985 A1* | 6/2015 | Di Censo ............ G06T 17/05 345/419 |

(56) References Cited

U.S. PATENT DOCUMENTS

| | | | |
|---|---|---|---|
| 2015/0360617 A1* | 12/2015 | Schulz | B60R 11/04 |
| | | | 701/41 |
| 2016/0008985 A1 | 1/2016 | Kim et al. | |
| 2016/0070527 A1 | 3/2016 | Ricci | |
| 2016/0086391 A1 | 3/2016 | Ricci | |
| 2016/0269456 A1 | 9/2016 | Ricci | |
| 2016/0269469 A1 | 9/2016 | Ricci | |
| 2018/0012091 A1 | 1/2018 | Ricci | |

FOREIGN PATENT DOCUMENTS

| | | |
|---|---|---|
| CN | 101303878 | 11/2008 |
| CN | 102467827 | 5/2012 |
| EP | 1223567 | 7/2002 |
| EP | 1484729 | 12/2004 |
| EP | 2192015 | 6/2010 |
| JP | 2004-284450 | 10/2004 |
| KR | 2006-0128484 | 12/2006 |
| WO | WO 2007/126204 | 11/2007 |
| WO | WO 2012/102879 | 8/2012 |
| WO | WO 2013/074866 | 5/2013 |
| WO | WO 2013/074867 | 5/2013 |
| WO | WO 2013/074868 | 5/2013 |
| WO | WO 2013/074897 | 5/2013 |
| WO | WO 2013/074899 | 5/2013 |
| WO | WO 2013/074901 | 5/2013 |
| WO | WO 2013/074919 | 5/2013 |
| WO | WO 2013/074981 | 5/2013 |
| WO | WO 2013/074983 | 5/2013 |
| WO | WO 2013/075005 | 5/2013 |
| WO | WO 2013/181310 | 12/2013 |
| WO | WO 2014/014862 | 1/2014 |
| WO | WO 2014/143563 | 9/2014 |
| WO | WO 2014/158667 | 10/2014 |
| WO | WO 2014/158672 | 10/2014 |
| WO | WO 2014/158766 | 10/2014 |
| WO | WO 2014/172312 | 10/2014 |
| WO | WO 2014/172313 | 10/2014 |
| WO | WO 2014/172316 | 10/2014 |
| WO | WO 2014/172320 | 10/2014 |
| WO | WO 2014/172322 | 10/2014 |
| WO | WO 2014/172323 | 10/2014 |
| WO | WO 2014/172327 | 10/2014 |
| WO | WO 2016/145073 | 9/2016 |
| WO | WO 2016/145100 | 9/2016 |

OTHER PUBLICATIONS

"Nexus 10 Guidebook for Android," Google Inc., © 2012, Edition 1.2, 166 pages.

"Self-Driving: Self-Driving Autonomous Cars," available at http://www.automotivetechnologies.com/autonomous-self-driving-cars, accessed Dec. 2016, 9 pages.

Amor-Segan et al., "Towards the Self Healing Vehicle," Automotive Electronics, Jun. 2007, 2007 3rd Institution of Engineering and Technology Conference, 7 pages.

Bennett, "Meet Samsung's Version of Apple AirPlay," CNET.com, Oct. 10, 2012, 11 pages.

Cairnie et al., "Using Finger-Pointing to Operate Secondary Controls in Automobiles," Proceedings of the IEEE Intelligent Vehicles Symposium 2000, Oct. 3-5, 2000, 6 pages.

Clark, "How Self-Driving Cars Work: The Nuts and Bolts Behind Google's Autonomous Car Program," Feb. 21, 2015, available at http://www.makeuseof.com/tag/how-self-driving-cars-work-the-nuts-and-bolts-behind-googles-autonomous-car-program/, 9 pages.

Deaton et al., "How Driverless Cars Will Work," Jul. 1, 2008, HowStuffWorks.com. <http://auto.howstuffworks.com/under-the-hood/trends-innovations/driverless-car.htm> Sep. 18, 2017, 10 pages.

Dumbaugh, "Safe Streets, Livable Streets: A Positive Approach to urban Roadside Design," Ph.D. dissertation for School of Civil & Environ. Engr., Georgia Inst. of Technology, Dec. 2005, 235 pages.

Fei et al., "A QoS-aware Dynamic Bandwidth Allocation Algorithm for Relay Stations in IEEE 802.16j-based Vehicular Networks," Proceedings of the 2010 IEEE Global Telecommunications Conference, Dec. 10, 2010, 10 pages.

Ge et al., "Optimal Relay Selection in IEEE 802.16j Multihop Relay Vehicular Networks," IEEE Transactions on Vehicular Technology, 2010, vol. 59(5), pp. 2198-2206.

Guizzo, Erico, "How Google's Self-Driving Car Works," Oct. 18, 2011, available at https://spectrum.ieee.org/automaton/robotics/artificial-intelligence/how-google-self-driving-car-works, 5 pages.

Heer et al., "ALPHA: An Adaptive and Lightweight Protocol for Hop-by-hop Authentication," Proceedings of CoNEXT 2008, Dec. 2008, pp. 1-12.

Jahnich et al., "Towards a Middleware Approach for a Self-Configurable Automotive Embedded System," International Federation for Information Processing, 2008, pp. 55-65.

Persson "Adaptive Middleware for Self-Configurable Embedded Real-Time Systems," KTH Industrial Engineering and Management, 2009, pp. iii-71 and references.

Raychaudhuri et al., "Emerging Wireless Technologies and the Future Mobile Internet," p. 48, Cambridge Press, 2011, 3 pages.

Siephens, Leah, "How Driverless Cars Work," Interesting Engineering, Apr. 28, 2016, available at https://interestingengineering.com/driverless-cars-work/, 7 pages.

Stoller, "Leader Election in Distributed Systems with Crash Failures," Indiana University, 1997, pp. 1-15.

Strunk et al., "The Elements of Style," 3d ed., Macmillan Publishing Co., 1979, 3 pages.

Suwatthikul, "Fault detection and diagnosis for in-vehicle networks," Intech, 2010, pp. 283-286 [retrieved from: www.intechopen.com/books/fault-detection-and-diagnosis-for-in-vehicle-networks].

Walter et al., "The smart car seat: personalized monitoring of vital signs in automotive applications." Personal and Ubiquitous Computing, Oct. 2011, vol. 15, No. 7, pp. 707-715.

Wolf et al., "Design, Implementation, and Evaluation of a Vehicular Hardware Security Module," ICISC'11 Proceedings of the 14th Int'l Conf. Information Security & Cryptology, Springer-Verlag Berlin, Heidelberg, 2011, pp. 302-318.

Official Action for U.S. Appl. No. 15/393,114, dated Sep. 6, 2018 17 pages.

Final Action for U.S. Appl. No. 15/393,114, dated Jan. 11, 2019 18 pages.

Final Action for U.S. Appl. No. 15/393,114, dated Apr. 24, 2019 21 pages.

Final Action for U.S. Appl. No. 15/393,114, dated Oct. 81, 2019 18 pages.

* cited by examiner

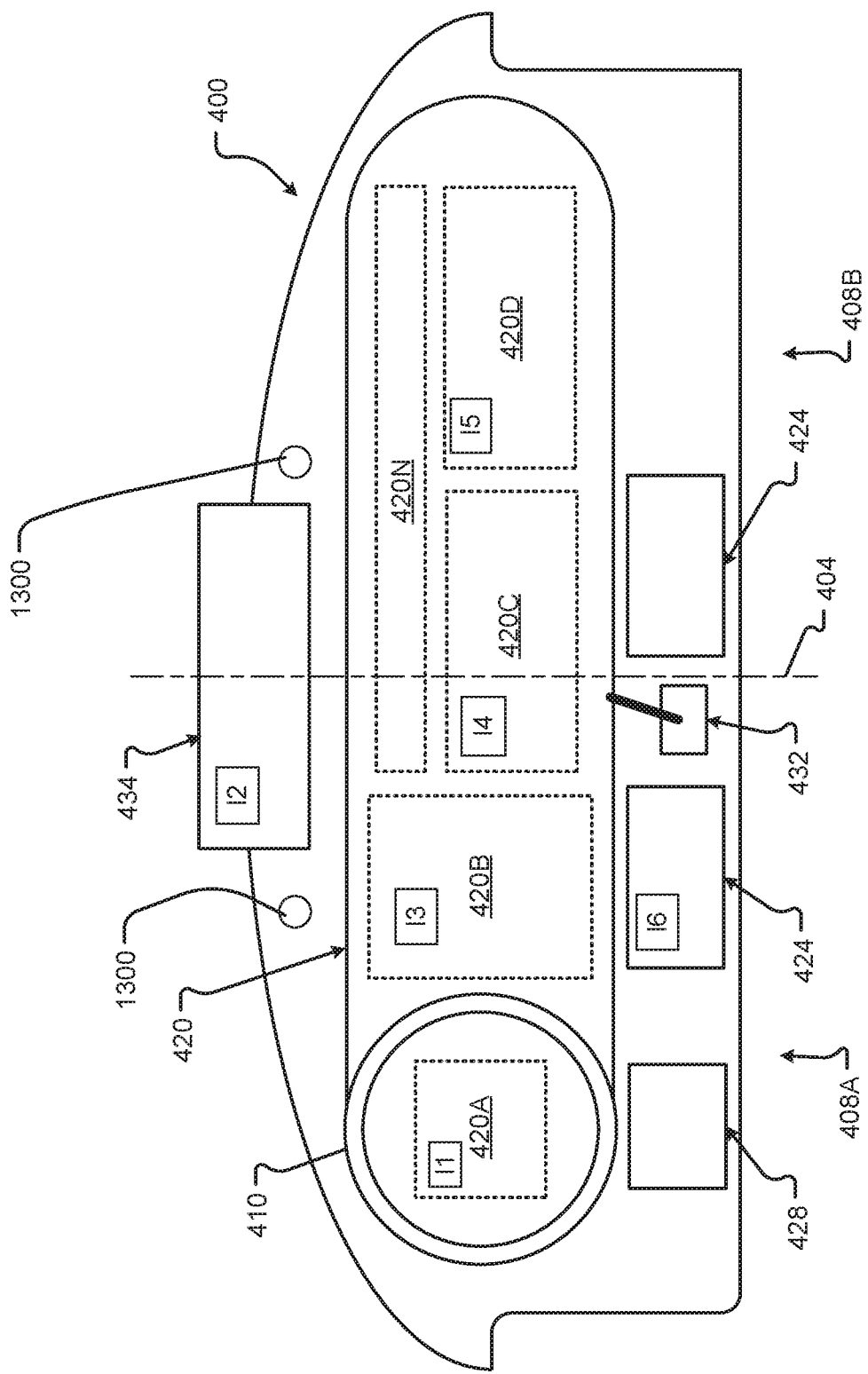

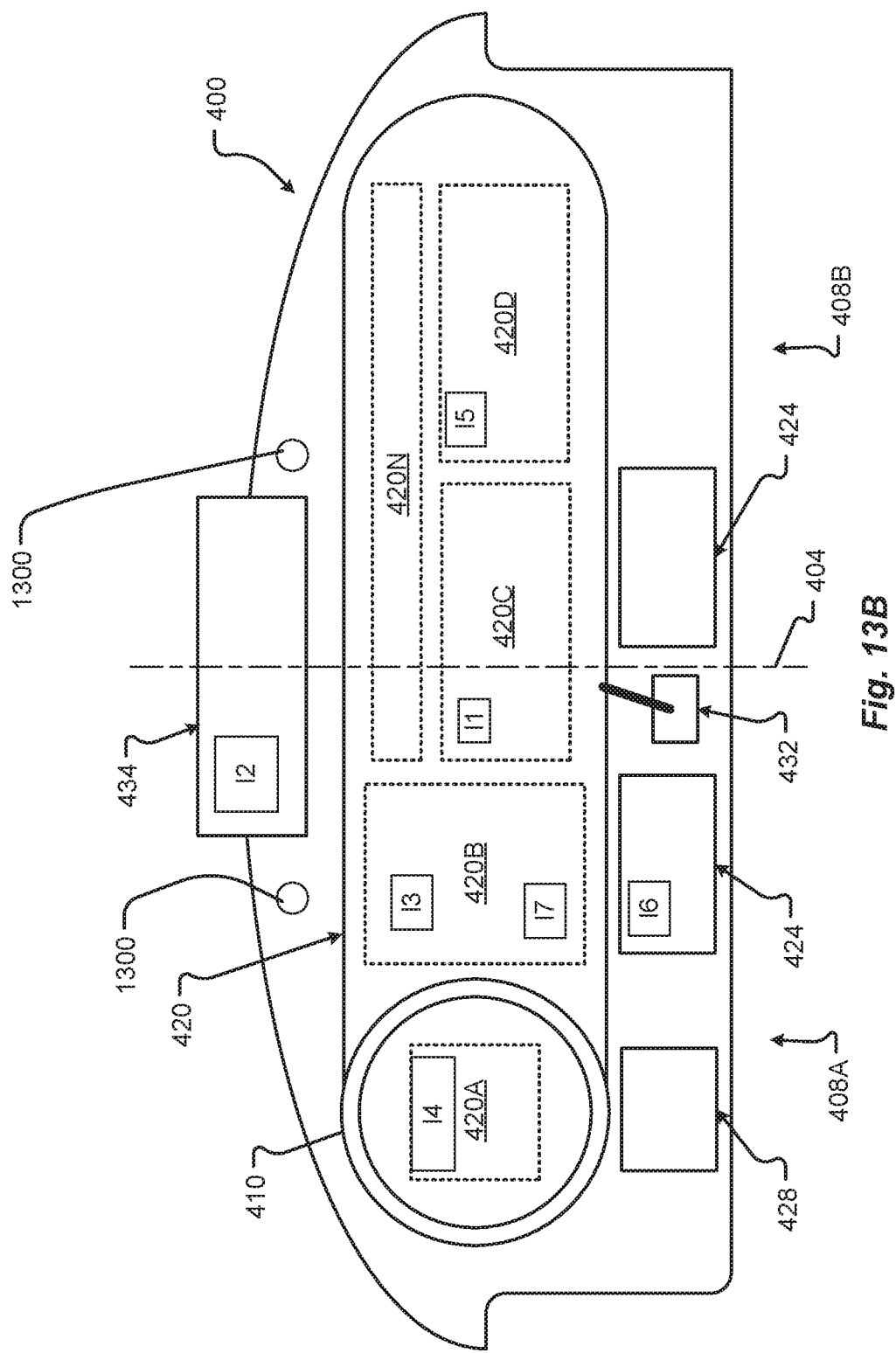

| Condition | Safety Score | Weight Associated with Safety Score | Raw Priority Score (RPS) | Priority Level | Recurrence Frequency Threshold to Exceed within Threshold Time | Presentation Effect | Occupant Preferences |
|---|---|---|---|---|---|---|---|
| Impaired driver | 10 | 1.0 | 10.0 | 1 | N/A | Add alert item(s) to display in primary viewing location | Flashing red font |
| Low-vision | 9 | 0.8 | 7.2 | 2 | N/A | Enlarge item(s) and/or change other visual settings | N/A |
| Repeated gaze toward temperature controls | 6 | 0.5 | 3.0 | 3 | 3 times in 3 minutes | Move temperature controls to primary viewing/interaction location | Blue font |
| Repeated gesture toward stereo controls | 6 | 0.5 | 3.0 | 3 | 3 times in 2 minutes | Move stereo controls to primary viewing/interaction location | Display stereo controls with stereo widget |
| High or low skin temperature | 5 | 0.2 | 1.0 | 4 | N/A | Add item to display skin temperature | Display skin temperature with temperature widget |

USER-ADJUSTED DISPLAY DEVICES AND METHODS OF OPERATING THE SAME

CROSS REFERENCE TO RELATED APPLICATIONS

The present application claims the benefits of and priority, under 35 U.S.C. § 119(e), to U.S. Provisional Application Ser. Nos. 62/359,563, filed on Jul. 7, 2016, entitled "Next Generation Vehicle"; and 62/378,348, filed Aug. 23, 2016, entitled "Next Generation Vehicle." The entire disclosures of the applications listed above are hereby incorporated by reference, in their entirety, for all that they teach and for all purposes.

FIELD

The present disclosure is generally directed to vehicle systems, in particular, toward electric and/or hybrid-electric vehicles.

BACKGROUND

In recent years, transportation methods have changed substantially. This change is due in part to a concern over the limited availability of natural resources, a proliferation in personal technology, and a societal shift to adopt more environmentally friendly transportation solutions. These considerations have encouraged the development of a number of new flexible-fuel vehicles, hybrid-electric vehicles, and electric vehicles.

While these vehicles appear to be new they are generally implemented as a number of traditional subsystems that are merely tied to an alternative power source. In fact, the design and construction of the vehicles is limited to standard frame sizes, shapes, materials, and transportation concepts. Among other things, these limitations fail to take advantage of the benefits of new technology, power sources, and support infrastructure.

BRIEF DESCRIPTION OF THE DRAWINGS

FIG. 13A illustrates one embodiment of a first presentation of information on a user-adjusted (or occupant-adjusted) display device of a vehicle;

FIG. 13B illustrates one embodiment of a second presentation of information on a user-adjusted (or occupant-adjusted) display device of a vehicle;

FIG. 16 illustrates an example look-up-table (LUT) that assists with determining effects for rendering for the second presentation according to at least one embodiment.

DETAILED DESCRIPTION

Embodiments of the present disclosure will be described in connection with a vehicle, and in some embodiments, an electric vehicle, rechargeable electric vehicle, and/or hybrid-electric vehicle and associated systems.

Figure 1:
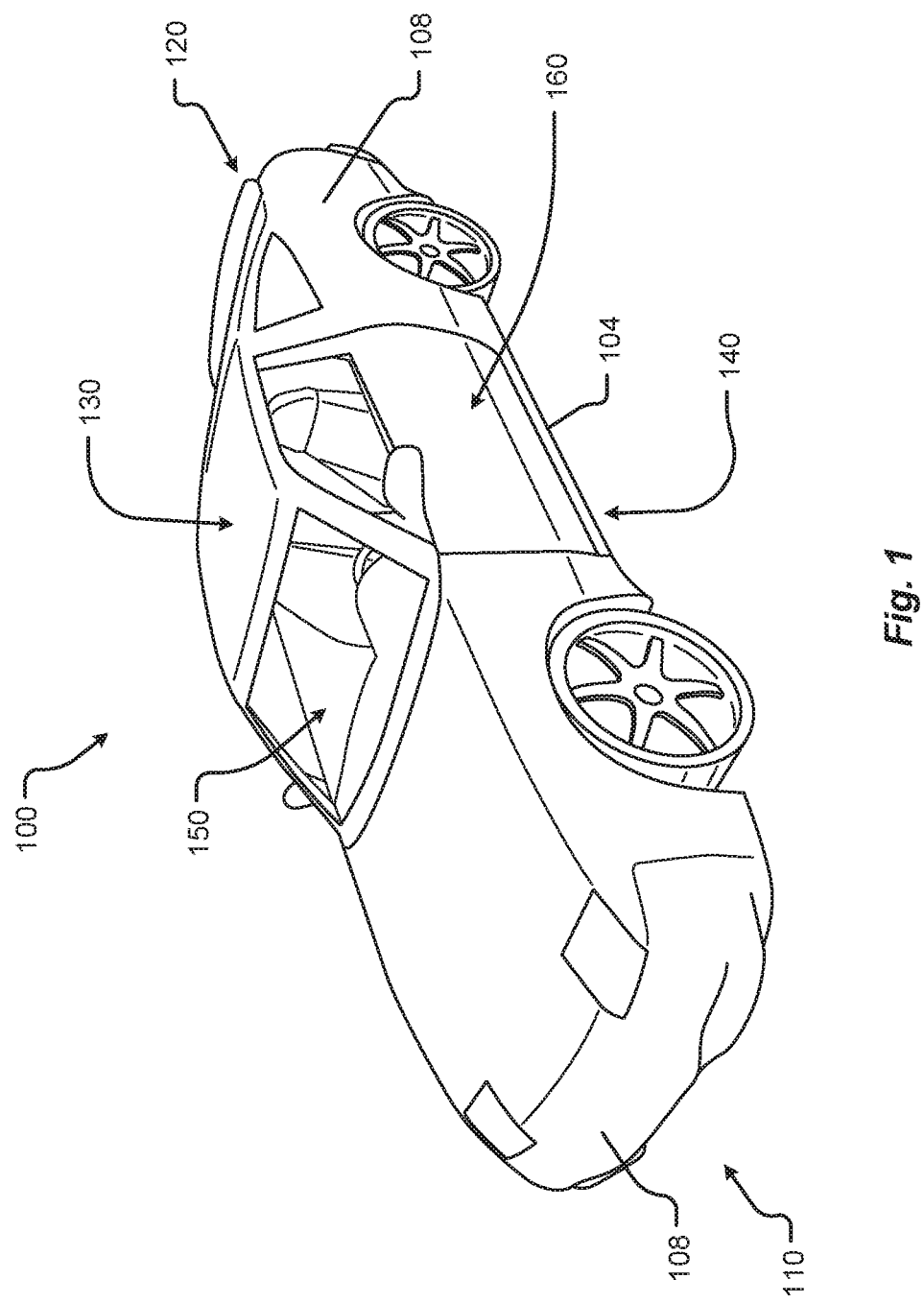
FIG. 1 shows a vehicle in accordance with embodiments of the present disclosure.

FIG. 1 shows a perspective view of a vehicle 100 in accordance with embodiments of the present disclosure. The electric vehicle 100 comprises a vehicle front 110, vehicle aft 120, vehicle roof 130, at least one vehicle side 160, a vehicle undercarriage 140, and a vehicle interior 150. In any event, the vehicle 100 may include a frame 104 and one or more body panels 108 mounted or affixed thereto. The vehicle 100 may include one or more interior components (e.g., components inside an interior space 150, or user space, of a vehicle 100, etc.), exterior components (e.g., components outside of the interior space 150, or user space, of a vehicle 100, etc.), drive systems, controls systems, structural components, etc.

Although shown in the form of a car, it should be appreciated that the vehicle 100 described herein may include any conveyance or model of a conveyance, where the conveyance was designed for the purpose of moving one or more tangible objects, such as people, animals, cargo, and the like. The term "vehicle" does not require that a conveyance moves or is capable of movement. Typical vehicles may include but are in no way limited to cars, trucks, motorcycles, busses, automobiles, trains, railed conveyances, boats, ships, marine conveyances, submarine conveyances, airplanes, space craft, flying machines, human-powered conveyances, and the like.

Figure 2:
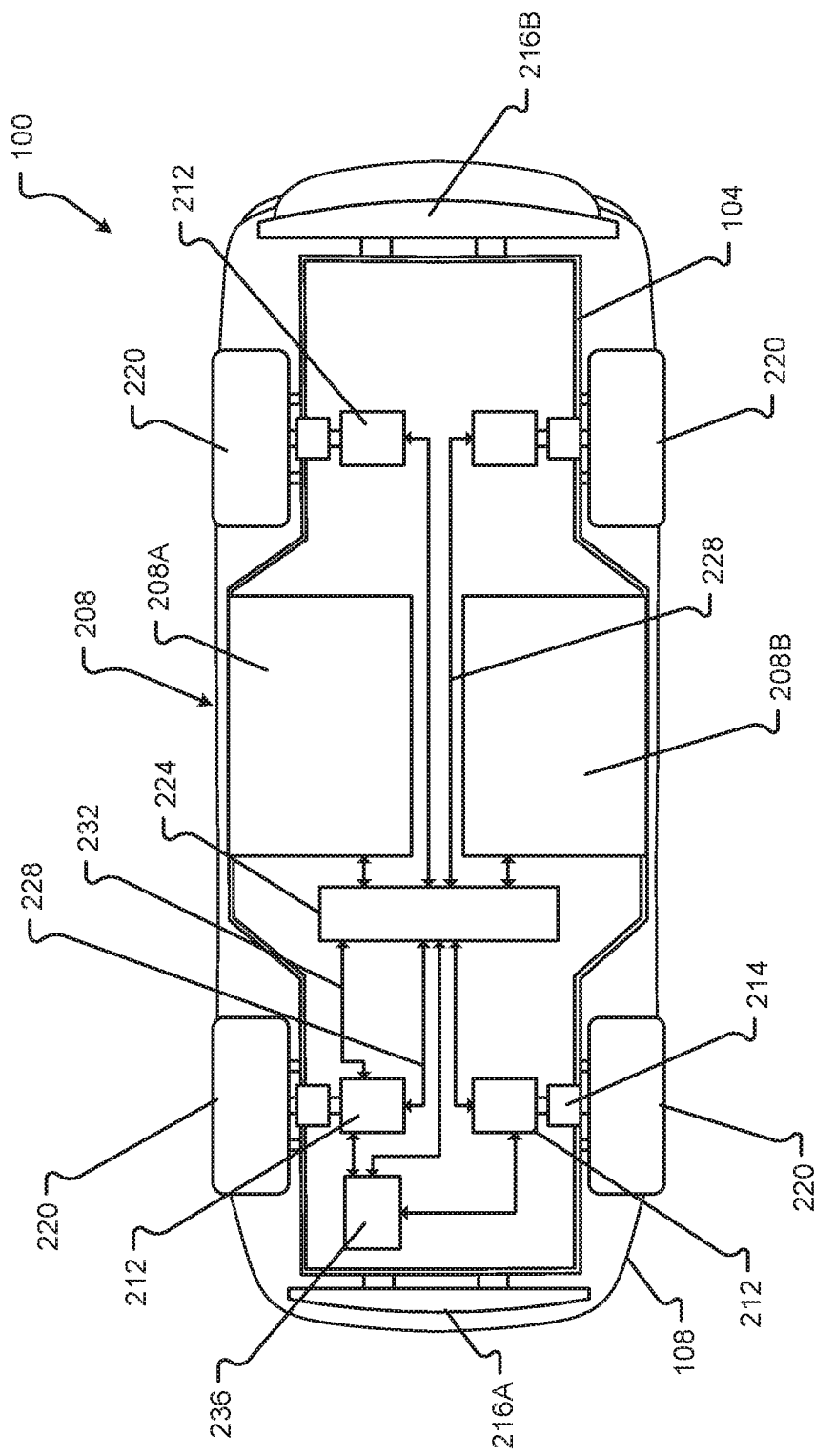
FIG. 2 shows a plan view of the vehicle in accordance with at least some embodiments of the present disclosure.

Referring now to FIG. 2, a plan view of a vehicle 100 will be described in accordance with embodiments of the present disclosure. As provided above, the vehicle 100 may comprise a number of electrical and/or mechanical systems, subsystems, etc. The mechanical systems of the vehicle 100 can include structural, power, safety, and communications subsystems, to name a few. While each subsystem may be described separately, it should be appreciated that the components of a particular subsystem may be shared between one or more other subsystems of the vehicle 100.

The structural subsystem includes the frame 104 of the vehicle 100. The frame 104 may comprise a separate frame and body construction (i.e., body-on-frame construction), a unitary frame and body construction (i.e., a unibody construction), or any other construction defining the structure of the vehicle 100. The frame 104 may be made from one or more materials including, but in no way limited to steel, titanium, aluminum, carbon fiber, plastic, polymers, etc., and/or combinations thereof. In some embodiments, the frame 104 may be formed, welded, fused, fastened, pressed, etc., combinations thereof, or otherwise shaped to define a physical structure and strength of the vehicle 100. In any event, the frame 104 may comprise one or more surfaces, connections, protrusions, cavities, mounting points, tabs, slots, or other features that are configured to receive other components that make up the vehicle 100. For example, the body panels 108, powertrain subsystem, controls systems, interior components, communications subsystem, and safety subsystem may interconnect with, or attach to, the frame 104 of the vehicle 100.

The frame 104 may include one or more modular system and/or subsystem connection mechanisms. These mechanisms may include features that are configured to provide a selectively interchangeable interface for one or more of the systems and/or subsystems described herein. The mechanisms may provide for a quick exchange, or swapping, of components while providing enhanced security and adaptability over conventional manufacturing or attachment. For instance, the ability to selectively interchange systems and/or subsystems in the vehicle 100 allow the vehicle 100 to adapt to the ever-changing technological demands of society and advances in safety. Among other things, the mechanisms may provide for the quick exchange of batteries, capacitors, power sources 208A, 208B, motors 212, engines, safety equipment, controllers, user interfaces, interiors exterior components, body panels 108, bumpers 216, sensors, etc., and/or combinations thereof. Additionally or alternatively, the mechanisms may provide unique security hardware and/or software embedded therein that, among other things, can prevent fraudulent or low quality construction replacements from being used in the vehicle 100. Similarly, the mechanisms, subsystems, and/or receiving features in the vehicle 100 may employ poka-yoke, or mistake-proofing, features that ensure a particular mechanism is always interconnected with the vehicle 100 in a correct position, function, etc.

By way of example, complete systems or subsystems may be removed and/or replaced from a vehicle 100 utilizing a single-minute exchange ("SME") principle. In some embodiments, the frame 104 may include slides, receptacles, cavities, protrusions, and/or a number of other features that allow for quick exchange of system components. In one embodiment, the frame 104 may include tray or ledge features, mechanical interconnection features, locking mechanisms, retaining mechanisms, etc., and/or combinations thereof. In some embodiments, it may be beneficial to quickly remove a used power source 208A, 208B (e.g., battery unit, capacitor unit, etc.) from the vehicle 100 and replace the used power source 208A, 208B with a charged or new power source. Continuing this example, the power source 208A, 208B may include selectively interchangeable features that interconnect with the frame 104 or other portion of the vehicle 100. For instance, in a power source 208A, 208B replacement, the quick release features may be configured to release the power source 208A, 208B from an engaged position and slide or move in a direction away from the frame 104 of a vehicle 100. Once removed, or separated from, the vehicle, the power source 208A, 208B may be replaced (e.g., with a new power source, a charged power source, etc.) by engaging the replacement power source into a system receiving position adjacent to the vehicle 100. In some embodiments, the vehicle 100 may include one or more actuators configured to position, lift, slide, or otherwise engage the replacement power source with the vehicle 100. In one embodiment, the replacement power source may be inserted into the vehicle 100 or vehicle frame 104 with mechanisms and/or machines that are external and/or separate from the vehicle 100.

In some embodiments, the frame 104 may include one or more features configured to selectively interconnect with other vehicles and/or portions of vehicles. These selectively interconnecting features can allow for one or more vehicles to selectively couple together and decouple for a variety of purposes. For example, it is an aspect of the present disclosure that a number of vehicles may be selectively coupled together to share energy, increase power output, provide security, decrease power consumption, provide towing services, and/or provide a range of other benefits. Continuing this example, the vehicles may be coupled together based on travel route, destination, preferences, settings, sensor information, and/or some other data. The coupling may be initiated by at least one controller of the vehicle and/or traffic control system upon determining that a coupling is beneficial to one or more vehicles in a group of vehicles or a traffic system. As can be appreciated, the power consumption for a group of vehicles traveling in a same direction may be reduced or decreased by removing any aerodynamic separation between vehicles. In this case, the vehicles may be coupled together to subject only the foremost vehicle in the coupling to air and/or wind resistance during travel. In one embodiment, the power output by the group of vehicles may be proportionally or selectively controlled to provide a specific output from each of the one or more of the vehicles in the group.

The interconnecting, or coupling, features may be configured as electromagnetic mechanisms, mechanical couplings, electromechanical coupling mechanisms, etc., and/or combinations thereof. The features may be selectively deployed from a portion of the frame 104 and/or body of the vehicle 100. In some cases, the features may be built into the frame 104 and/or body of the vehicle 100. In any event, the features may deploy from an unexposed position to an exposed position or may be configured to selectively engage/disengage without requiring an exposure or deployment of the mechanism from the frame 104 and/or body of the vehicle 100. In some embodiments, the interconnecting features may be configured to interconnect one or more of power, communications, electrical energy, fuel, and/or the like. One or more of the power, mechanical, and/or communications connections between vehicles may be part of a single interconnection mechanism. In some embodiments, the interconnection mechanism may include multiple connection mechanisms. In any event, the single interconnection mechanism or the interconnection mechanism may employ the poka-yoke features as described above.

The power system of the vehicle 100 may include the powertrain, power distribution system, accessory power system, and/or any other components that store power, provide power, convert power, and/or distribute power to one or more portions of the vehicle 100. The powertrain may include the one or more electric motors 212 of the vehicle 100. The electric motors 212 are configured to convert electrical energy provided by a power source into mechanical energy. This mechanical energy may be in the form of a rotational or other output force that is configured to propel or otherwise provide a motive force for the vehicle 100.

In some embodiments, the vehicle 100 may include one or more drive wheels 220 that are driven by the one or more electric motors 212 and motor controllers 214. In some cases, the vehicle 100 may include an electric motor 212 configured to provide a driving force for each drive wheel 220. In other cases, a single electric motor 212 may be configured to share an output force between two or more drive wheels 220 via one or more power transmission components. It is an aspect of the present disclosure that the powertrain may include one or more power transmission components, motor controllers 214, and/or power controllers that can provide a controlled output of power to one or more of the drive wheels 220 of the vehicle 100. The power transmission components, power controllers, or motor controllers 214 may be controlled by at least one other vehicle controller or computer system as described herein.

As provided above, the powertrain of the vehicle 100 may include one or more power sources 208A, 208B. These one or more power sources 208A, 208B may be configured to provide drive power, system and/or subsystem power, accessory power, etc. While described herein as a single power source 208 for sake of clarity, embodiments of the present disclosure are not so limited. For example, it should be appreciated that independent, different, or separate power sources 208A, 208B may provide power to various systems of the vehicle 100. For instance, a drive power source may be configured to provide the power for the one or more electric motors 212 of the vehicle 100, while a system power source may be configured to provide the power for one or more other systems and/or subsystems of the vehicle 100. Other power sources may include an accessory power source, a backup power source, a critical system power source, and/or other separate power sources. Separating the power sources 208A, 208B in this manner may provide a number of benefits over conventional vehicle systems. For example, separating the power sources 208A, 208B allow one power source 208 to be removed and/or replaced independently without requiring that power be removed from all systems and/or subsystems of the vehicle 100 during a power source 208 removal/replacement. For instance, one or more of the accessories, communications, safety equipment, and/or backup power systems, etc., may be maintained even when a particular power source 208A, 208B is depleted, removed, or becomes otherwise inoperable.

In some embodiments, the drive power source may be separated into two or more cells, units, sources, and/or systems. By way of example, a vehicle 100 may include a first drive power source 208A and a second drive power source 208B. The first drive power source 208A may be operated independently from or in conjunction with the second drive power source 208B and vice versa. Continuing this example, the first drive power source 208A may be removed from a vehicle while a second drive power source 208B can be maintained in the vehicle 100 to provide drive power. This approach allows the vehicle 100 to significantly reduce weight (e.g., of the first drive power source 208A, etc.) and improve power consumption, even if only for a temporary period of time. In some cases, a vehicle 100 running low on power may automatically determine that pulling over to a rest area, emergency lane, and removing, or "dropping off," at least one power source 208A, 208B may reduce enough weight of the vehicle 100 to allow the vehicle 100 to navigate to the closest power source replacement and/or charging area. In some embodiments, the removed, or "dropped off," power source 208A may be collected by a collection service, vehicle mechanic, tow truck, or even another vehicle or individual.

The power source 208 may include a GPS or other geographical location system that may be configured to emit a location signal to one or more receiving entities. For instance, the signal may be broadcast or targeted to a specific receiving party. Additionally or alternatively, the power source 208 may include a unique identifier that may be used to associate the power source 208 with a particular vehicle 100 or vehicle user. This unique identifier may allow an efficient recovery of the power source 208 dropped off. In some embodiments, the unique identifier may provide information for the particular vehicle 100 or vehicle user to be billed or charged with a cost of recovery for the power source 208.

The power source 208 may include a charge controller 224 that may be configured to determine charge levels of the power source 208, control a rate at which charge is drawn from the power source 208, control a rate at which charge is added to the power source 208, and/or monitor a health of the power source 208 (e.g., one or more cells, portions, etc.). In some embodiments, the charge controller 224 or the power source 208 may include a communication interface. The communication interface can allow the charge controller 224 to report a state of the power source 208 to one or more other controllers of the vehicle 100 or even communicate with a communication device separate and/or apart from the vehicle 100. Additionally or alternatively, the communication interface may be configured to receive instructions (e.g., control instructions, charge instructions, communication instructions, etc.) from one or more other controllers or computers of the vehicle 100 or a communication device that is separate and/or apart from the vehicle 100.

The powertrain includes one or more power distribution systems configured to transmit power from the power source 208 to one or more electric motors 212 in the vehicle 100. The power distribution system may include electrical interconnections 228 in the form of cables, wires, traces, wireless power transmission systems, etc., and/or combinations thereof. It is an aspect of the present disclosure that the vehicle 100 include one or more redundant electrical interconnections 232 of the power distribution system. The redundant electrical interconnections 232 can allow power to be distributed to one or more systems and/or subsystems of the vehicle 100 even in the event of a failure of an electrical interconnection portion of the vehicle 100 (e.g., due to an accident, mishap, tampering, or other harm to a particular electrical interconnection, etc.). In some embodiments, a user of a vehicle 100 may be alerted via a user interface associated with the vehicle 100 that a redundant electrical interconnection 232 is being used and/or damage has occurred to a particular area of the vehicle electrical system. In any event, the one or more redundant electrical interconnections 232 may be configured along completely different routes than the electrical interconnections 228 and/or include different modes of failure than the electrical interconnections 228 to, among other things, prevent a total interruption power distribution in the event of a failure.

In some embodiments, the power distribution system may include an energy recovery system 236. This energy recovery system 236, or kinetic energy recovery system, may be configured to recover energy produced by the movement of a vehicle 100. The recovered energy may be stored as electrical and/or mechanical energy. For instance, as a vehicle 100 travels or moves, a certain amount of energy is required to accelerate, maintain a speed, stop, or slow the vehicle 100. In any event, a moving vehicle has a certain amount of kinetic energy. When brakes are applied in a typical moving vehicle, most of the kinetic energy of the vehicle is lost as the generation of heat in the braking mechanism. In an energy recovery system 236, when a vehicle 100 brakes, at least a portion of the kinetic energy is converted into electrical and/or mechanical energy for storage. Mechanical energy may be stored as mechanical movement (e.g., in a flywheel, etc.) and electrical energy may be stored in batteries, capacitors, and/or some other electrical storage system. In some embodiments, electrical energy recovered may be stored in the power source 208. For example, the recovered electrical energy may be used to charge the power source 208 of the vehicle 100.

The vehicle 100 may include one or more safety systems. Vehicle safety systems can include a variety of mechanical and/or electrical components including, but in no way limited to, low impact or energy-absorbing bumpers 216A, 216B, crumple zones, reinforced body panels, reinforced frame components, impact bars, power source containment zones, safety glass, seatbelts, supplemental restraint systems, air bags, escape hatches, removable access panels, impact sensors, accelerometers, vision systems, radar systems, etc., and/or the like. In some embodiments, the one or more of the safety components may include a safety sensor or group of safety sensors associated with the one or more of the safety components. For example, a crumple zone may include one or more strain gages, impact sensors, pressure transducers, etc. These sensors may be configured to detect or determine whether a portion of the vehicle 100 has been subjected to a particular force, deformation, or other impact. Once detected, the information collected by the sensors may be transmitted or sent to one or more of a controller of the vehicle 100 (e.g., a safety controller, vehicle controller, etc.) or a communication device associated with the vehicle 100 (e.g., across a communication network, etc.).

Figure 3:
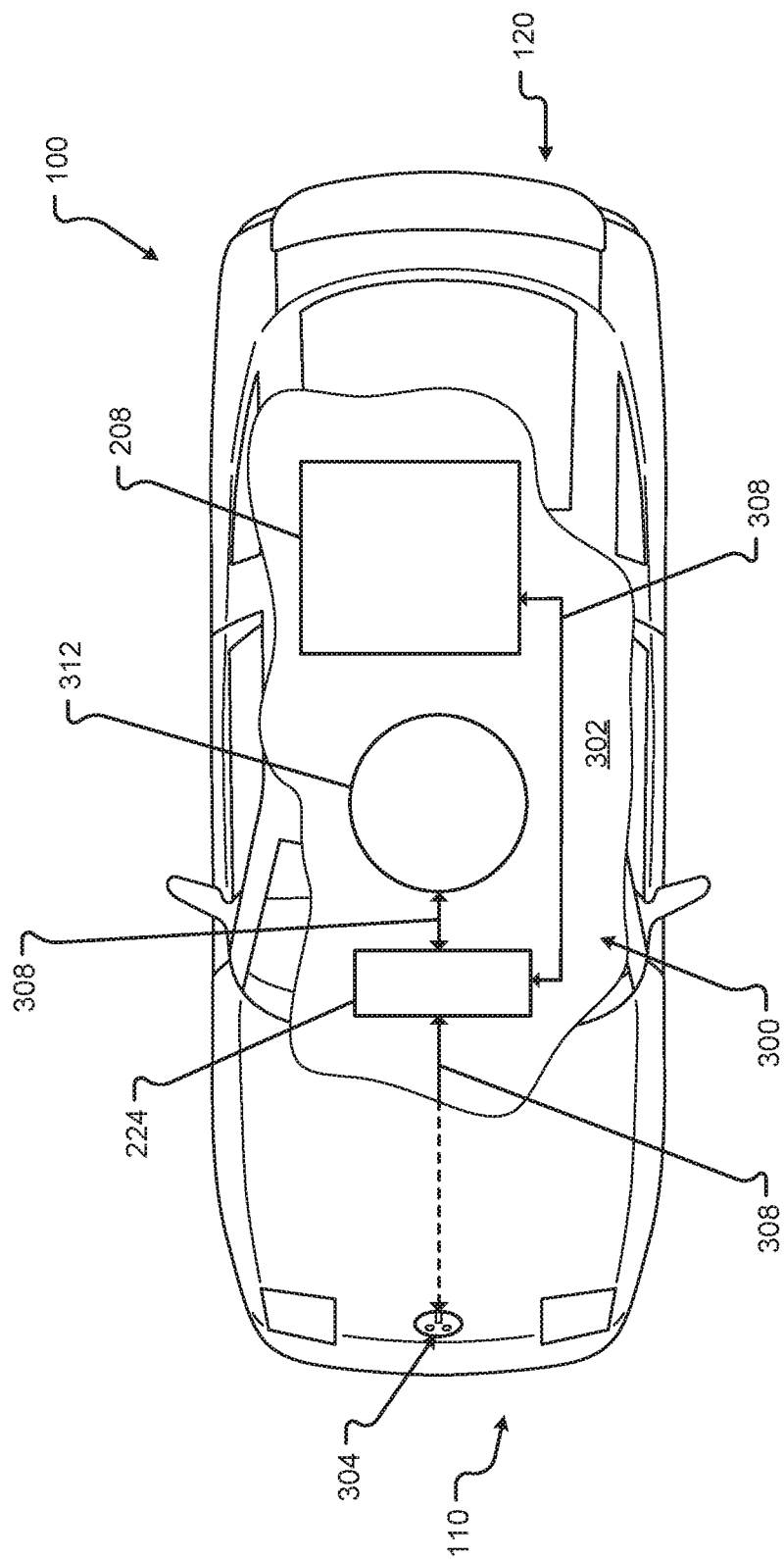
FIG. 3 shows a plan view of the vehicle in accordance with embodiments of the present disclosure

FIG. 3 shows a plan view of the vehicle 100 in accordance with embodiments of the present disclosure. In particular, FIG. 3 shows a broken section 302 of a charging system 300 for the vehicle 100. The charging system 300 may include a plug or receptacle 304 configured to receive power from an external power source (e.g., a source of power that is external to and/or separate from the vehicle 100, etc.). An example of an external power source may include the standard industrial, commercial, or residential power that is provided across power lines. Another example of an external power source may include a proprietary power system configured to provide power to the vehicle 100. In any event, power received at the plug/receptacle 304 may be transferred via at least one power transmission interconnection 308. Similar, if not identical, to the electrical interconnections 228 described above, the at least one power transmission interconnection 308 may be one or more cables, wires, traces, wireless power transmission systems, etc., and/or combinations thereof. Electrical energy in the form of charge can be transferred from the external power source to the charge controller 224. As provided above, the charge controller 224 may regulate the addition of charge to at least one power source 208 of the vehicle 100 (e.g., until the at least one power source 208 is full or at a capacity, etc.).

In some embodiments, the vehicle 100 may include an inductive charging system and inductive charger 312. The inductive charger 312 may be configured to receive electrical energy from an inductive power source external to the vehicle 100. In one embodiment, when the vehicle 100 and/or the inductive charger 312 is positioned over an inductive power source external to the vehicle 100, electrical energy can be transferred from the inductive power source to the vehicle 100. For example, the inductive charger 312 may receive the charge and transfer the charge via at least one power transmission interconnection 308 to the charge controller 324 and/or the power source 208 of the vehicle 100. The inductive charger 312 may be concealed in a portion of the vehicle 100 (e.g., at least partially protected by the frame 104, one or more body panels 108, a shroud, a shield, a protective cover, etc., and/or combinations thereof) and/or may be deployed from the vehicle 100. In some embodiments, the inductive charger 312 may be configured to receive charge only when the inductive charger 312 is deployed from the vehicle 100. In other embodiments, the inductive charger 312 may be configured to receive charge while concealed in the portion of the vehicle 100.

In addition to the mechanical components described herein, the vehicle 100 may include a number of user interface devices. The user interface devices receive and translate human input into a mechanical movement or electrical signal or stimulus. The human input may be one or more of motion (e.g., body movement, body part movement, in two-dimensional or three-dimensional space, etc.), voice, touch, and/or physical interaction with the components of the vehicle 100. In some embodiments, the human input may be configured to control one or more functions of the vehicle 100 and/or systems of the vehicle 100 described herein. User interfaces may include, but are in no way limited to, at least one graphical user interface of a display device, steering wheel or mechanism, transmission lever or button (e.g., including park, neutral, reverse, and/or drive positions, etc.), throttle control pedal or mechanism, brake control pedal or mechanism, power control switch, communications equipment, etc.

Figure 4:
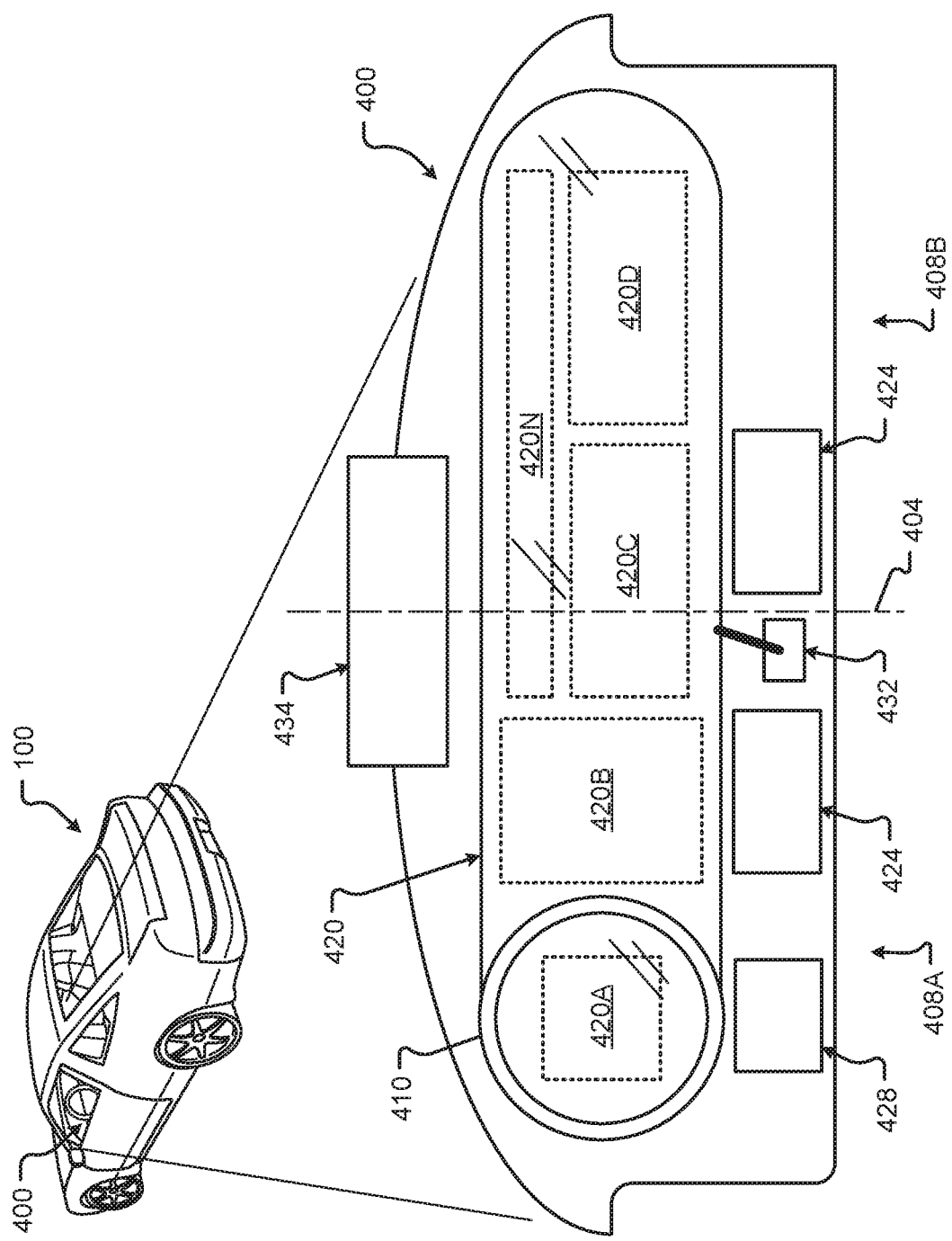
FIG. 4 shows an embodiment of the instrument panel of the vehicle according to one embodiment of the present disclosure.

FIG. 4 shows one embodiment of the instrument panel 400 of the vehicle 100. The instrument panel 400 of vehicle 100 comprises a steering wheel 410, a vehicle operational display 420 (e.g., configured to present and/or display driving data such as speed, measured air resistance, vehicle information, entertainment information, etc.), one or more auxiliary displays 424 (e.g., configured to present and/or display information segregated from the operational display 420, entertainment applications, movies, music, etc.), a heads-up display 434 (e.g., configured to display any information previously described including, but in no way limited to, guidance information such as route to destination, or obstacle warning information to warn of a potential collision, or some or all primary vehicle operational data such as speed, resistance, etc.), a power management display 428 (e.g., configured to display data corresponding to electric power levels of vehicle 100, reserve power, charging status, etc.), and an input device 432 (e.g., a controller, touchscreen, or other interface device configured to interface with one or more displays in the instrument panel or components of the vehicle 100. The input device 432 may be configured as a joystick, mouse, touchpad, tablet, 3D gesture capture device, etc.). In some embodiments, the input device 432 may be used to manually maneuver a portion of the vehicle 100 into a charging position (e.g., moving a charging plate to a desired separation distance, etc.).

While one or more of displays of instrument panel 400 may be touch-screen displays, it should be appreciated that the vehicle operational display may be a display incapable of receiving touch input. For instance, the operational display 420 that spans across an interior space centerline 404 and across both a first zone 408A and a second zone 408B may be isolated from receiving input from touch, especially from a passenger. In some cases, a display that provides vehicle operation or critical systems information and interface may be restricted from receiving touch input and/or be configured as a non-touch display. This type of configuration can prevent dangerous mistakes in providing touch input where such input may cause an accident or unwanted control.

In some embodiments, one or more displays of the instrument panel 400 may be mobile devices and/or applications residing on a mobile device such as a smart phone. Additionally or alternatively, any of the information described herein may be presented to one or more portions 420A-N of the operational display 420 or other display 424, 428, 434. In one embodiment, one or more displays of the instrument panel 400 may be physically separated or detached from the instrument panel 400. In some cases, a detachable display may remain tethered to the instrument panel.

The portions 420A-N of the operational display 420 may be dynamically reconfigured and/or resized to suit any display of information as described. Additionally or alternatively, the number of portions 420A-N used to visually present information via the operational display 420 may be dynamically increased or decreased as required, and are not limited to the configurations shown.

Figure 5:
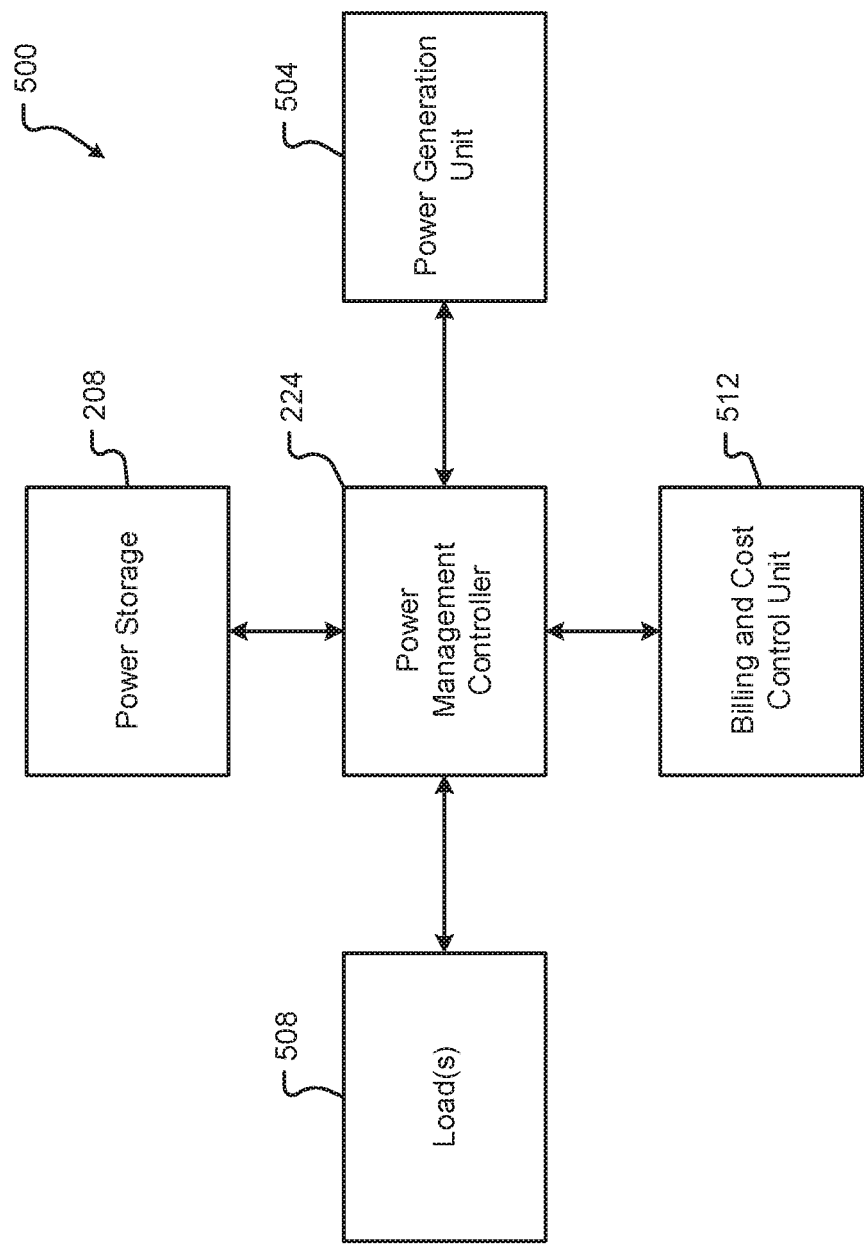
FIG. 5 is a block diagram of an embodiment of an electrical system of the vehicle.

An embodiment of the electrical system 500 associated with the vehicle 100 may be as shown in FIG. 5. The electrical system 500 can include power source(s) that generate power, power storage that stores power, and/or load(s) that consume power. Power sources may be associated with a power generation unit 504. Power storage may be associated with a power storage system 208. Loads may be associated with loads 508. The electrical system 500 may be managed by a power management controller 224. Further, the electrical system 500 can include one or more other interfaces or controllers, which can include the billing and cost control unit 512.

Figure 6:
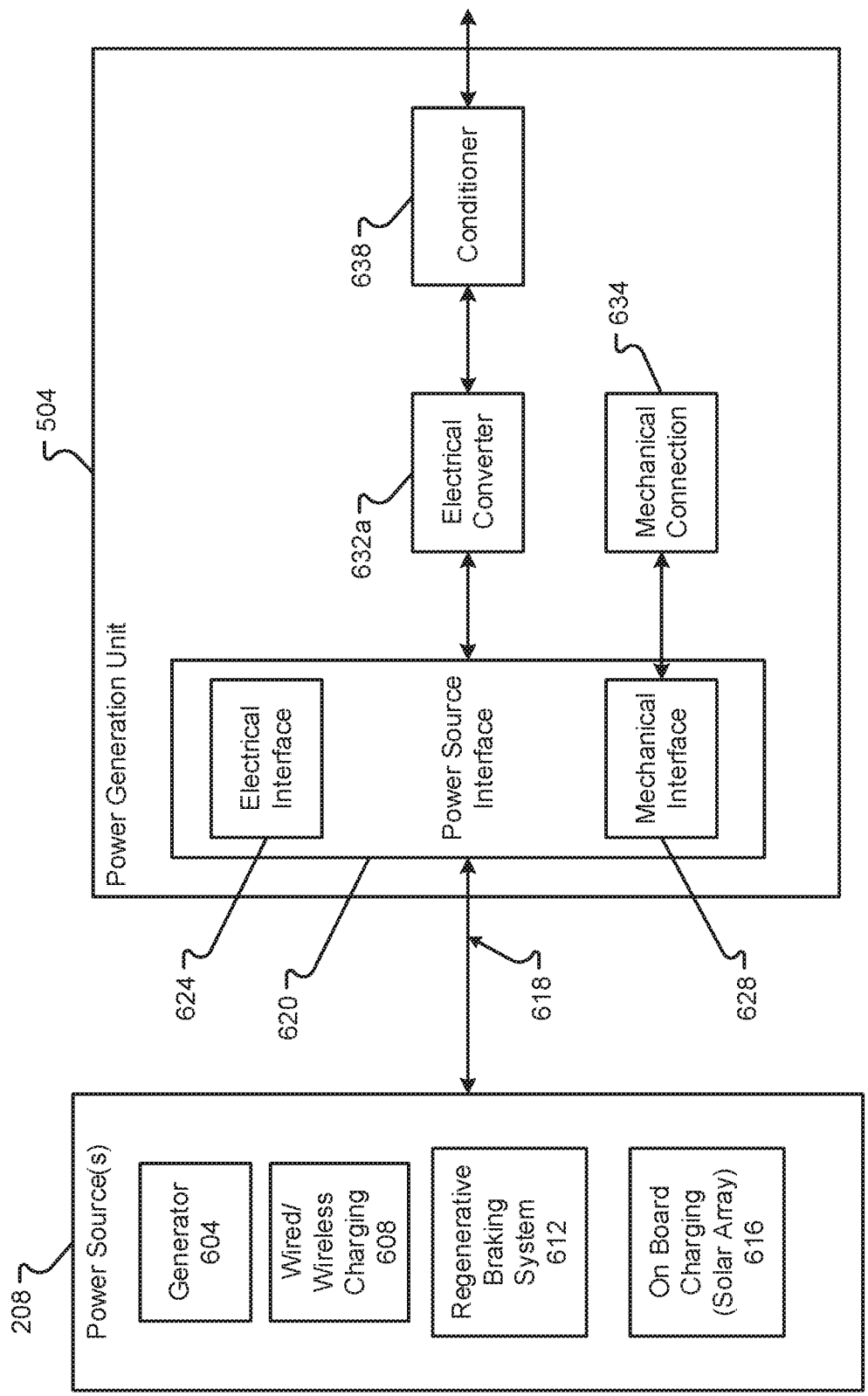
FIG. 6 is a block diagram of an embodiment of a power generation unit associated with the electrical system of the vehicle.

The power generation unit 504 may be as described in conjunction with FIG. 6. The power storage component 208 may be as described in conjunction with FIG. 7. The loads 508 may be as described in conjunction with FIG. 8.

The billing and cost control unit 512 may interface with the power management controller 224 to determine the amount of charge or power provided to the power storage 208 through the power generation unit 504. The billing and cost control unit 512 can then provide information for billing the vehicle owner. Thus, the billing and cost control unit 512 can receive and/or send power information to third party system(s) regarding the received charge from an external source. The information provided can help determine an amount of money required, from the owner of the vehicle, as payment for the provided power. Alternatively, or in addition, if the owner of the vehicle provided power to another vehicle (or another device/system), that owner may be owed compensation for the provided power or energy, e.g., a credit.

The power management controller 224 can be a computer or computing system(s) and/or electrical system with associated components, as described herein, capable of managing the power generation unit 504 to receive power, routing the power to the power storage 208, and then providing the power from either the power generation unit 504 and/or the power storage 208 to the loads 508. Thus, the power management controller 224 may execute programming that controls switches, devices, components, etc. involved in the reception, storage, and provision of the power in the electrical system 500.

An embodiment of the power generation unit 504 may be as shown in FIG. 6. Generally, the power generation unit 504 may be electrically coupled to one or more power sources 208. The power sources 208 can include power sources internal and/or associated with the vehicle 100 and/or power sources external to the vehicle 100 to which the vehicle 100 electrically connects. One of the internal power sources can include an on board generator 604. The generator 604 may be an alternating current (AC) generator, a direct current (DC) generator or a self-excited generator. The AC generators can include induction generators, linear electric generators, and/or other types of generators. The DC generators can include homopolar generators and/or other types of generators. The generator 604 can be brushless or include brush contacts and generate the electric field with permanent magnets or through induction. The generator 604 may be mechanically coupled to a source of kinetic energy, such as an axle or some other power take-off. The generator 604 may also have another mechanical coupling to an exterior source of kinetic energy, for example, a wind turbine.

Another power source 208 may include wired or wireless charging 608. The wireless charging system 608 may include inductive and/or resonant frequency inductive charging systems that can include coils, frequency generators, controllers, etc. Wired charging may be any kind of grid-connected charging that has a physical connection, although, the wireless charging may be grid connected through a wireless interface. The wired charging system can include connectors, wired interconnections, the controllers, etc. The wired and wireless charging systems 608 can provide power to the power generation unit 504 from external power sources 208.

Internal sources for power may include a regenerative braking system 612. The regenerative braking system 612 can convert the kinetic energy of the moving car into electrical energy through a generation system mounted within the wheels, axle, and/or braking system of the vehicle 100. The regenerative braking system 612 can include any coils, magnets, electrical interconnections, converters, controllers, etc. required to convert the kinetic energy into electrical energy.

Another source of power 208, internal to or associated with the vehicle 100, may be a solar array 616. The solar array 616 may include any system or device of one or more solar cells mounted on the exterior of the vehicle 100 or integrated within the body panels of the vehicle 100 that provides or converts solar energy into electrical energy to provide to the power generation unit 504.

The power sources 208 may be connected to the power generation unit 504 through an electrical interconnection 618. The electrical interconnection 618 can include any wire, interface, bus, etc. between the one or more power sources 208 and the power generation unit 504.

The power generation unit 504 can also include a power source interface 620. The power source interface 620 can be any type of physical and/or electrical interface used to receive the electrical energy from the one or more power sources 208; thus, the power source interface 620 can include an electrical interface 624 that receives the electrical energy and a mechanical interface 628 which may include wires, connectors, or other types of devices or physical connections. The mechanical interface 608 can also include a physical/electrical connection 634 to the power generation unit 504.

The electrical energy from the power source 208 can be processed through the power source interface 624 to an electric converter 632. The electric converter 632 may convert the characteristics of the power from one of the power sources into a useable form that may be used either by the power storage 208 or one or more loads 508 within the vehicle 100. The electrical converter 624 may include any electronics or electrical devices and/or component that can change electrical characteristics, e.g., AC frequency, amplitude, phase, etc. associated with the electrical energy provided by the power source 208. The converted electrical energy may then be provided to an optional conditioner 1638. The conditioner 1638 may include any electronics or electrical devices and/or component that may further condition the converted electrical energy by removing harmonics, noise, etc. from the electrical energy to provide a more stable and effective form of power to the vehicle 100.

Figure 7:
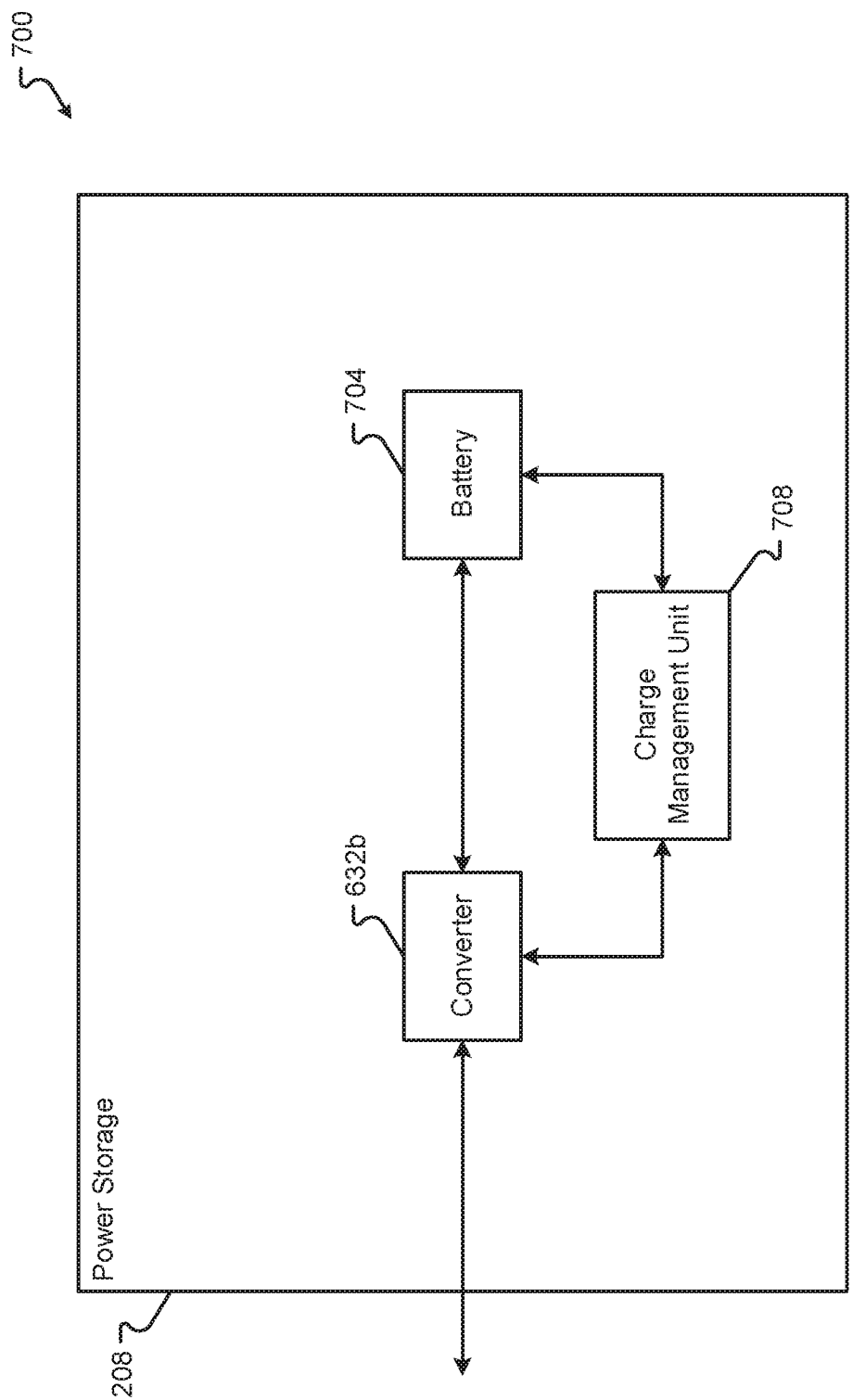
FIG. 7 is a block diagram of an embodiment of power storage associated with the electrical system of the vehicle.

An embodiment of the power storage 208 may be as shown in FIG. 7. The power storage unit can include an electrical converter 632b, one or more batteries, one or more rechargeable batteries, one or more capacitors, one or more accumulators, one or more supercapacitors, one or more ultrabatteries, and/or superconducting magnetics 704, and/or a charge management unit 708. The converter 632b may be the same or similar to the electrical converter 632a shown in FIG. 6. The converter 632b may be a replacement for the electric converter 632a shown in FIG. 6 and thus eliminate the need for the electrical converter 632a as shown in FIG. 6. However, if the electrical converter 632a is provided in the power generation unit 504, the converter 632b, as shown in the power storage unit 208, may be eliminated. The converter 632b can also be redundant or different from the electrical converter 632a shown in FIG. 6 and may provide a different form of energy to the battery and/or capacitors 704. Thus, the converter 632b can change the energy characteristics specifically for the battery/capacitor 704.

The battery 704 can be any type of battery for storing electrical energy, for example, a lithium ion battery, a lead acid battery, a nickel cadmium battery, etc. Further, the battery 704 may include different types of power storage systems, such as, ionic fluids or other types of fuel cell systems. The energy storage 704 may also include one or more high-capacity capacitors 704. The capacitors 704 may be used for long-term or short-term storage of electrical energy. The input into the battery or capacitor 704 may be different from the output, and thus, the capacitor 704 may be charged quickly but drain slowly. The functioning of the converter 632 and battery capacitor 704 may be monitored or managed by a charge management unit 708.

The charge management unit 708 can include any hardware (e.g., any electronics or electrical devices and/or components), software, or firmware operable to adjust the operations of the converter 632 or batteries/capacitors 704. The charge management unit 708 can receive inputs or periodically monitor the converter 632 and/or battery/capacitor 704 from this information; the charge management unit 708 may then adjust settings or inputs into the converter 632 or battery/capacitor 704 to control the operation of the power storage system 208.

Figure 8:
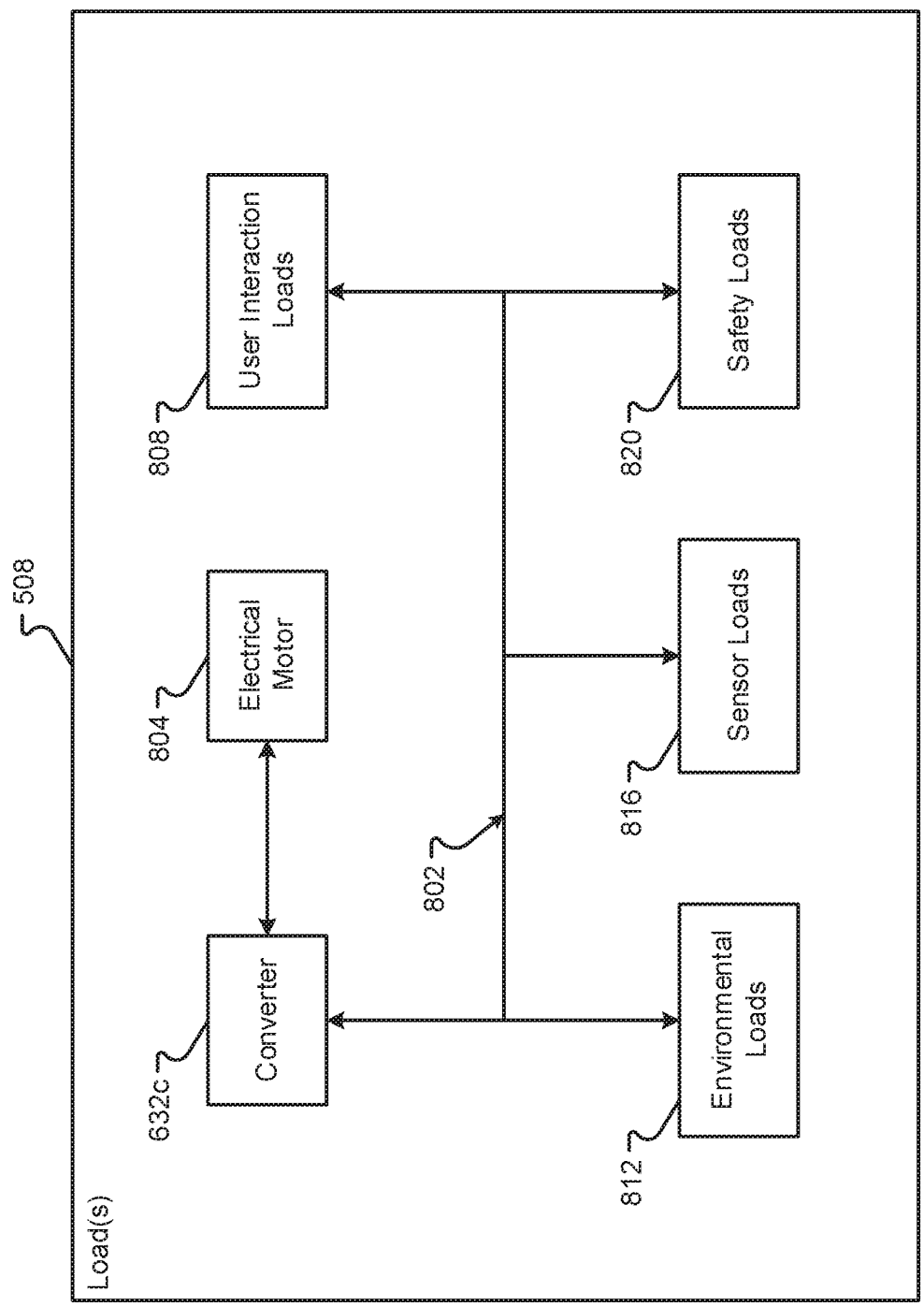
FIG. 8 is a block diagram of an embodiment of loads associated with the electrical system of the vehicle.

An embodiment of one or more loads 508 associated with the vehicle 100 may be as shown in FIG. 8. The loads 508 may include a bus or electrical interconnection system 802, which provides electrical energy to one or more different loads within the vehicle 100. The bus 802 can be any number of wires or interfaces used to connect the power generation unit 504 and/or power storage 208 to the one or more loads 508. The converter 632c may be an interface from the power generation unit 504 or the power storage 208 into the loads 508. The converter 632c may be the same or similar to electric converter 632a as shown in FIG. 6. Similar to the discussion of the converter 632b in FIG. 7, the converter 632c may be eliminated, if the electric converter 632a, shown in FIG. 6, is present. However, the converter 632c may further condition or change the energy characteristics for the bus 802 for use by the loads 508. The converter 632c may also provide electrical energy to electric motor 804, which may power the vehicle 100.

The electric motor 804 can be any type of DC or AC electric motor. The electric motor may be a direct drive or induction motor using permanent magnets and/or winding either on the stator or rotor. The electric motor 804 may also be wireless or include brush contacts. The electric motor 804 may be capable of providing a torque and enough kinetic energy to move the vehicle 100 in traffic. In some embodiments, the electric motor 804 may be similar, if not identical, to the electric motor 212 described in conjunction with FIG. 2.

The different loads 508 may also include environmental loads 812, sensor loads 816, safety loads 820, user interaction loads 808, etc. User interaction loads 808 can be any energy used by user interfaces or systems that interact with the driver and/or passenger(s) of the vehicle 100. These loads 808 may include, for example, the heads up display 434, the dash display 420, 424, 428, the radio, user interfaces on the head unit, lights, radio, and/or other types of loads that provide or receive information from the occupants of the vehicle 100. The environmental loads 812 can be any loads used to control the environment within the vehicle 100. For example, the air conditioning or heating unit of the vehicle 100 can be environmental loads 812. Other environmental loads can include lights, fans, and/or defrosting units, etc. that may control the environment within, and/or outside of, the vehicle 100. The sensor loads 816 can be any loads used by sensors, for example, air bag sensors, GPS, and other such sensors used to either manage or control the vehicle 100 and/or provide information or feedback to the vehicle occupants. The safety loads 820 can include any safety equipment, for example, seat belt alarms, airbags, headlights, blinkers, etc. that may be used to manage the safety of the occupants of the vehicle 100. There may be more or fewer loads than those described herein, although they may not be shown in FIG. 8.

Figure 9:
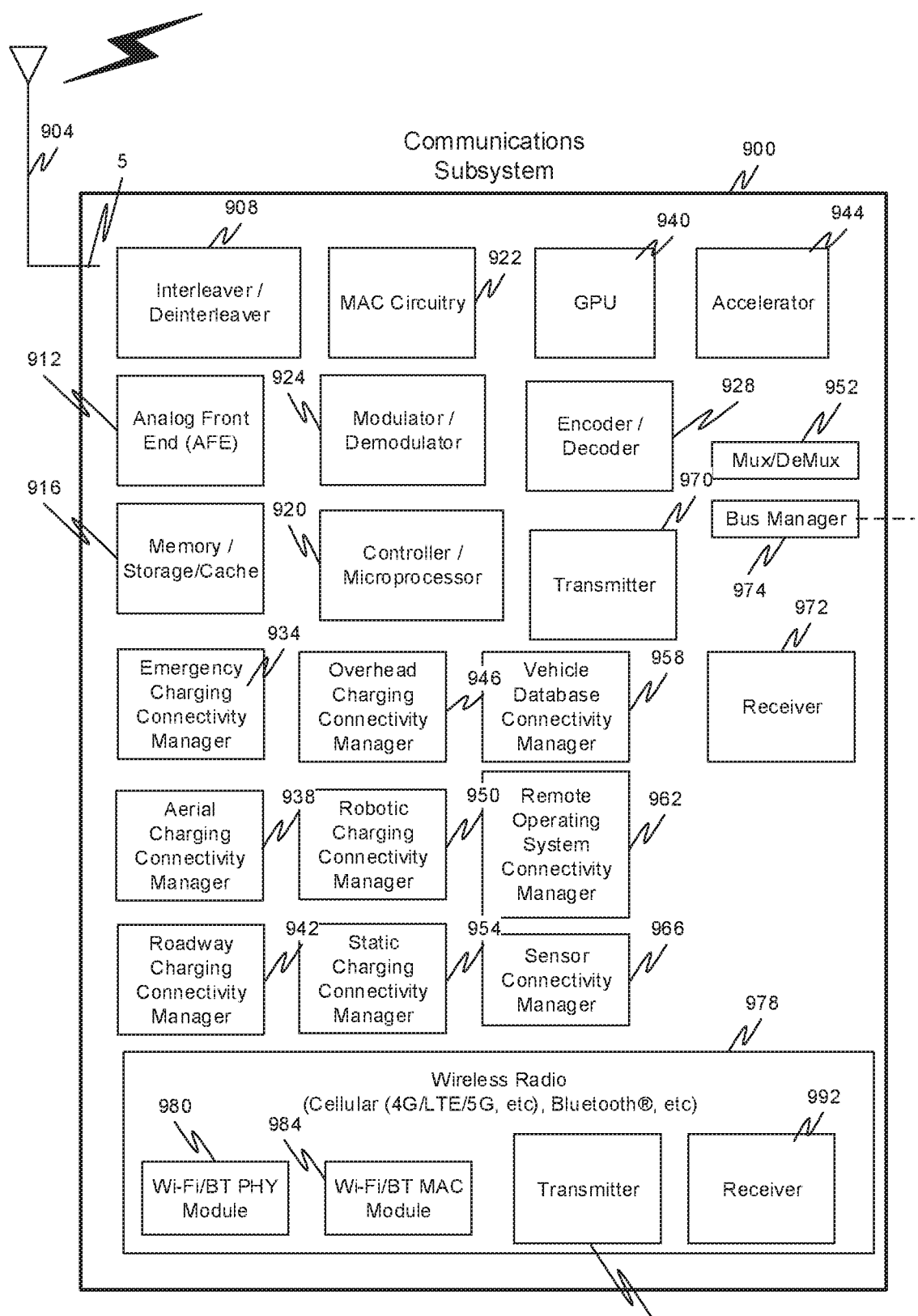
FIG. 9 is a block diagram of an embodiment of a communications subsystem of the vehicle.

FIG. 9 illustrates a hardware diagram of communications componentry that can be optionally associated with the vehicle 100 in accordance with embodiments of the present disclosure.

The communications componentry can include one or more wired or wireless devices such as a transceiver(s) and/or modem that allows communications not only between the various systems disclosed herein but also with other devices, such as devices on a network, and/or on a distributed network such as the Internet and/or in the cloud and/or with other vehicle(s).

The communications subsystem can also include inter- and intra-vehicle communications capabilities such as hotspot and/or access point connectivity for any one or more of the vehicle occupants and/or vehicle-to-vehicle communications.

Additionally, and while not specifically illustrated, the communications subsystem can include one or more communications links (that can be wired or wireless) and/or communications busses (managed by the bus manager 974), including one or more of CANbus, OBD-II, ARCINC 429, Byteflight, CAN (Controller Area Network), D2B (Domestic Digital Bus), FlexRay, DC-BUS, IDB-1394, IEBus, I2C, ISO 9141-1/-2, J1708, J1587, J1850, J1939, ISO 11783, Keyword Protocol 2000, LIN (Local Interconnect Network), MOST (Media Oriented Systems Transport), Multifunction Vehicle Bus, SMARTwireX, SPI, VAN (Vehicle Area Network), and the like or in general any communications protocol and/or standard(s).

The various protocols and communications can be communicated one or more of wirelessly and/or over transmission media such as single wire, twisted pair, fiber optic, IEEE 1394, MIL-STD-1553, MIL-STD-1773, power-line communication, or the like. (All of the above standards and protocols are incorporated herein by reference in their entirety).

As discussed, the communications subsystem enables communications between any if the inter-vehicle systems and subsystems as well as communications with non-collocated resources, such as those reachable over a network such as the Internet.

The communications subsystem 900, in addition to well-known componentry (which has been omitted for clarity), includes interconnected elements including one or more of: one or more antennas 904, an interleaver/deinterleaver 908, an analog front end (AFE) 912, memory/storage/cache 916, controller/microprocessor 920, MAC circuitry 922, modulator/demodulator 924, encoder/decoder 928, a plurality of connectivity managers 934-966, GPU 940, accelerator 944, a multiplexer/demultiplexer 952, transmitter 970, receiver 972 and wireless radio 978 components such as a Wi-Fi PHY/Bluetooth® module 980, a Wi-Fi/BT MAC module 984, transmitter 988 and receiver 992. The various elements in the device 900 are connected by one or more links/busses 5 (not shown, again for sake of clarity).

The device 400 can have one more antennas 904, for use in wireless communications such as multi-input multi-output (MIMO) communications, multi-user multi-input multi-output (MU-MIMO) communications Bluetooth®, LTE, 4G, 5G, Near-Field Communication (NFC), etc., and in general for any type of wireless communications. The antenna(s) 904 can include, but are not limited to one or more of directional antennas, omnidirectional antennas, monopoles, patch antennas, loop antennas, microstrip antennas, dipoles, and any other antenna(s) suitable for communication transmission/reception. In an exemplary embodiment, transmission/reception using MIMO may require particular antenna spacing. In another exemplary embodiment, MIMO transmission/reception can enable spatial diversity allowing for different channel characteristics at each of the antennas. In yet another embodiment, MIMO transmission/reception can be used to distribute resources to multiple users for example within the vehicle 100 and/or in another vehicle.

Antenna(s) 904 generally interact with the Analog Front End (AFE) 912, which is needed to enable the correct processing of the received modulated signal and signal conditioning for a transmitted signal. The AFE 912 can be functionally located between the antenna and a digital baseband system in order to convert the analog signal into a digital signal for processing and vice-versa.

The subsystem 900 can also include a controller/microprocessor 920 and a memory/storage/cache 916. The subsystem 900 can interact with the memory/storage/cache 916 which may store information and operations necessary for configuring and transmitting or receiving the information described herein. The memory/storage/cache 916 may also be used in connection with the execution of application programming or instructions by the controller/microprocessor 920, and for temporary or long term storage of program instructions and/or data. As examples, the memory/storage/cache 920 may comprise a computer-readable device, RAM, ROM, DRAM, SDRAM, and/or other storage device(s) and media.

The controller/microprocessor 920 may comprise a general purpose programmable processor or controller for executing application programming or instructions related to the subsystem 900. Furthermore, the controller/microprocessor 920 can perform operations for configuring and transmitting/receiving information as described herein. The controller/microprocessor 920 may include multiple processor cores, and/or implement multiple virtual processors. Optionally, the controller/microprocessor 920 may include multiple physical processors. By way of example, the controller/microprocessor 920 may comprise a specially configured Application Specific Integrated Circuit (ASIC) or other integrated circuit, a digital signal processor(s), a controller, a hardwired electronic or logic circuit, a programmable logic device or gate array, a special purpose computer, or the like.

The subsystem 900 can further include a transmitter 970 and receiver 972 which can transmit and receive signals, respectively, to and from other devices, subsystems and/or other destinations using the one or more antennas 904 and/or links/busses. Included in the subsystem 900 circuitry is the medium access control or MAC Circuitry 922. MAC circuitry 922 provides for controlling access to the wireless medium. In an exemplary embodiment, the MAC circuitry 922 may be arranged to contend for the wireless medium and configure frames or packets for communicating over the wired/wireless medium.

The subsystem 900 can also optionally contain a security module (not shown). This security module can contain information regarding but not limited to, security parameters required to connect the device to one or more other devices or other available network(s), and can include WEP or WPA/WPA-2 (optionally+AES and/or TKIP) security access keys, network keys, etc. The WEP security access key is a security password used by Wi-Fi networks. Knowledge of this code can enable a wireless device to exchange information with an access point and/or another device. The information exchange can occur through encoded messages with the WEP access code often being chosen by the network administrator. WPA is an added security standard that is also used in conjunction with network connectivity with stronger encryption than WEP.

In some embodiments, the communications subsystem 900 also includes a GPU 940, an accelerator 944, a Wi-Fi/BT/BLE PHY module 980 and a Wi-Fi/BT/BLE MAC module 984 and wireless transmitter 988 and receiver 992. In some embodiments, the GPU 940 may be a graphics processing unit, or visual processing unit, comprising at least one circuit and/or chip that manipulates and changes memory to accelerate the creation of images in a frame buffer for output to at least one display device. The GPU 940 may include one or more of a display device connection port, printed circuit board (PCB), a GPU chip, a metal-oxide-semiconductor field-effect transistor (MOSFET), memory (e.g., single data rate random-access memory (SDRAM), double data rate random-access memory (DDR) RAM, etc., and/or combinations thereof), a secondary processing chip (e.g., handling video out capabilities, processing, and/or other functions in addition to the GPU chip, etc.), a capacitor, heatsink, temperature control or cooling fan, motherboard connection, shielding, and the like.

The various connectivity managers 934-966 (even) manage and/or coordinate communications between the subsystem 900 and one or more of the systems disclosed herein and one or more other devices/systems. The connectivity managers include an emergency charging connectivity manager 934, an aerial charging connectivity manager 938, a roadway charging connectivity manager 942, an overhead charging connectivity manager 946, a robotic charging connectivity manager 950, a static charging connectivity manager 954, a vehicle database connectivity manager 958, a remote operating system connectivity manager 962 and a sensor connectivity manager 966.

The emergency charging connectivity manager 934 can coordinate not only the physical connectivity between the vehicle 100 and the emergency charging device/vehicle, but can also communicate with one or more of the power management controller, one or more third parties and optionally a billing system(s). As an example, the vehicle 100 can establish communications with the emergency charging device/vehicle to one or more of coordinate interconnectivity between the two (e.g., by spatially aligning the charging receptacle on the vehicle with the charger on the emergency charging vehicle) and optionally share navigation information. Once charging is complete, the amount of charge provided can be tracked and optionally forwarded to, for example, a third party for billing. In addition to being able to manage connectivity for the exchange of power, the emergency charging connectivity manager 934 can also communicate information, such as billing information to the emergency charging vehicle and/or a third party. This billing information could be, for example, the owner of the vehicle, the driver/occupant(s) of the vehicle, company information, or in general any information usable to charge the appropriate entity for the power received.

The aerial charging connectivity manager 938 can coordinate not only the physical connectivity between the vehicle 100 and the aerial charging device/vehicle, but can also communicate with one or more of the power management controller, one or more third parties and optionally a billing system(s). As an example, the vehicle 100 can establish communications with the aerial charging device/vehicle to one or more of coordinate interconnectivity between the two (e.g., by spatially aligning the charging receptacle on the vehicle with the charger on the emergency charging vehicle) and optionally share navigation information. Once charging is complete, the amount of charge provided can be tracked and optionally forwarded to, for example, a third party for billing. In addition to being able to manage connectivity for the exchange of power, the aerial charging connectivity manager 938 can similarly communicate information, such as billing information to the aerial charging vehicle and/or a third party. This billing information could be, for example, the owner of the vehicle 100, the driver/occupant(s) of the vehicle 100, company information, or in general any information usable to charge the appropriate entity for the power received etc., as discussed.

The roadway charging connectivity manager 942 and overhead charging connectivity manager 946 can coordinate not only the physical connectivity between the vehicle 100 and the charging device/system, but can also communicate with one or more of the power management controller, one or more third parties and optionally a billing system(s). As one example, the vehicle 100 can request a charge from the charging system when, for example, the vehicle 100 needs or is predicted to need power. As an example, the vehicle 100 can establish communications with the charging device/vehicle to one or more of coordinate interconnectivity between the two for charging and share information for billing. Once charging is complete, the amount of charge provided can be tracked and optionally forwarded to, for example, a third party for billing. This billing information could be, for example, the owner of the vehicle 100, the driver/occupant(s) of the vehicle 100, company information, or in general any information usable to charge the appropriate entity for the power received etc., as discussed. The person responsible for paying for the charge could also receive a copy of the billing information as is customary. The robotic charging connectivity manager 950 and static charging connectivity manager 954 can operate in a similar manner to that described herein.

The vehicle database connectivity manager 958 allows the subsystem to receive and/or share information stored in the vehicle database. This information can be shared with other vehicle components/subsystems and/or other entities, such as third parties and/or charging systems. The information can also be shared with one or more vehicle occupant devices, such as an app (application) on a mobile device the driver uses to track information about the vehicle 100 and/or a dealer or service/maintenance provider. In general any information stored in the vehicle database can optionally be shared with any one or more other devices optionally subject to any privacy or confidentially restrictions.

The remote operating system connectivity manager 962 facilitates communications between the vehicle 100 and any one or more autonomous vehicle systems. These communications can include one or more of navigation information, vehicle information, other vehicle information, weather information, occupant information, or in general any information related to the remote operation of the vehicle 100.

The sensor connectivity manager 966 facilitates communications between any one or more of the vehicle sensors and any one or more of the other vehicle systems. The sensor connectivity manager 966 can also facilitate communications between any one or more of the sensors and/or vehicle systems and any other destination, such as a service company, app, or in general to any destination where sensor data is needed.

In accordance with one exemplary embodiment, any of the communications discussed herein can be communicated via the conductor(s) used for charging. One exemplary protocol usable for these communications is Power-line communication (PLC). PLC is a communication protocol that uses electrical wiring to simultaneously carry both data, and Alternating Current (AC) electric power transmission or electric power distribution. It is also known as power-line carrier, power-line digital subscriber line (PDSL), mains communication, power-line telecommunications, or power-line networking (PLN). For DC environments in vehicles PLC can be used in conjunction with CAN-bus, LIN-bus over power line (DC-LIN) and DC-BUS.

The communications subsystem can also optionally manage one or more identifiers, such as an IP (internet protocol) address(es), associated with the vehicle and one or other system or subsystems or components therein. These identifiers can be used in conjunction with any one or more of the connectivity managers as discussed herein.

Figure 10:
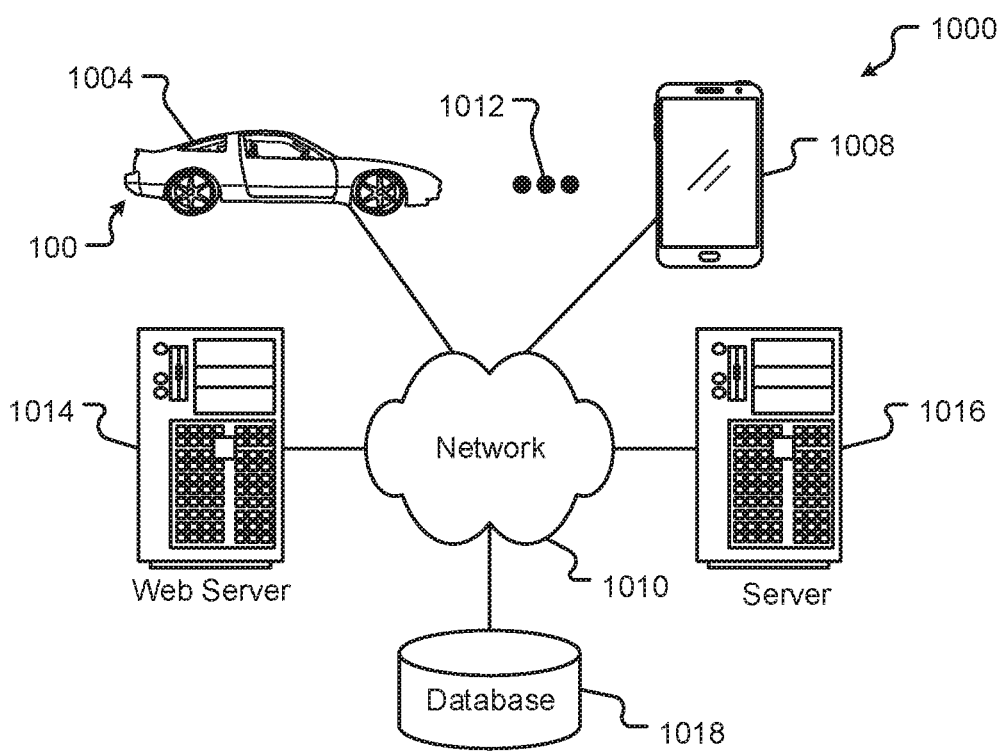
FIG. 10 is a block diagram of a computing environment associated with the embodiments presented herein.

FIG. 10 illustrates a block diagram of a computing environment 1000 that may function as the servers, user computers, or other systems provided and described herein. The environment 1000 includes one or more user computers, or computing devices, such as a vehicle computing device 1004, a communication device 1008, and/or more 1012. The computing devices 1004, 1008, 1012 may include general purpose personal computers (including, merely by way of example, personal computers, and/or laptop computers running various versions of Microsoft Corp.'s Windows® and/or Apple Corp.'s Macintosh® operating systems) and/or workstation computers running any of a variety of commercially-available UNIX® or UNIX-like operating systems. These computing devices 1004, 1008, 1012 may also have any of a variety of applications, including for example, database client and/or server applications, and web browser applications. Alternatively, the computing devices 1004, 1008, 1012 may be any other electronic device, such as a thin-client computer, Internet-enabled mobile telephone, and/or personal digital assistant, capable of communicating via a network 1010 and/or displaying and navigating web pages or other types of electronic documents. Although the exemplary computer environment 1000 is shown with two computing devices, any number of user computers or computing devices may be supported.

Environment 1000 further includes a network 1010. The network 1010 may can be any type of network familiar to those skilled in the art that can support data communications using any of a variety of commercially-available protocols, including without limitation SIP, TCP/IP, SNA, IPX, AppleTalk, and the like. Merely by way of example, the network 1010 maybe a local area network ("LAN"), such as an Ethernet network, a Token-Ring network and/or the like; a wide-area network; a virtual network, including without limitation a virtual private network ("VPN"); the Internet; an intranet; an extranet; a public switched telephone network ("PSTN"); an infra-red network; a wireless network (e.g., a network operating under any of the IEEE 802.9 suite of protocols, the Bluetooth® protocol known in the art, and/or any other wireless protocol); and/or any combination of these and/or other networks.

The system may also include one or more servers 1014, 1016. In this example, server 1014 is shown as a web server and server 1016 is shown as an application server. The web server 1014, which may be used to process requests for web pages or other electronic documents from computing devices 1004, 1008, 1012. The web server 1014 can be running an operating system including any of those discussed above, as well as any commercially-available server operating systems. The web server 1014 can also run a variety of server applications, including SIP (Session Initiation Protocol) servers, HTTP(s) servers, FTP servers, CGI servers, database servers, Java servers, and the like. In some instances, the web server 1014 may publish operations available operations as one or more web services.

The environment 1000 may also include one or more file and or/application servers 1016, which can, in addition to an operating system, include one or more applications accessible by a client running on one or more of the computing devices 1004, 1008, 1012. The server(s) 1016 and/or 1014 may be one or more general purpose computers capable of executing programs or scripts in response to the computing devices 1004, 1008, 1012. As one example, the server 1016, 1014 may execute one or more web applications. The web application may be implemented as one or more scripts or programs written in any programming language, such as Java™, C, C#®, or C++, and/or any scripting language, such as Perl, Python, or TCL, as well as combinations of any programming/scripting languages. The application server(s) 1016 may also include database servers, including without limitation those commercially available from Oracle®, Microsoft®, Sybase®, IBM® and the like, which can process requests from database clients running on a computing device 1004, 1008, 1012.

The web pages created by the server 1014 and/or 1016 may be forwarded to a computing device 1004, 1008, 1012 via a web (file) server 1014, 1016. Similarly, the web server 1014 may be able to receive web page requests, web services invocations, and/or input data from a computing device 1004, 1008, 1012 (e.g., a user computer, etc.) and can forward the web page requests and/or input data to the web (application) server 1016. In further embodiments, the server 1016 may function as a file server. Although for ease of description, FIG. 10 illustrates a separate web server 1014 and file/application server 1016, those skilled in the art will recognize that the functions described with respect to servers 1014, 1016 may be performed by a single server and/or a plurality of specialized servers, depending on implementation-specific needs and parameters. The computer systems 1004, 1008, 1012, web (file) server 1014 and/or web (application) server 1016 may function as the system, devices, or components described in FIGS. 1-10.

The environment 1000 may also include a database 1018. The database 1018 may reside in a variety of locations. By way of example, database 1018 may reside on a storage medium local to (and/or resident in) one or more of the computers 1004, 1008, 1012, 1014, 1016. Alternatively, it may be remote from any or all of the computers 1004, 1008, 1012, 1014, 1016, and in communication (e.g., via the network 1010) with one or more of these. The database 1018 may reside in a storage-area network ("SAN") familiar to those skilled in the art. Similarly, any necessary files for performing the functions attributed to the computers 1004, 1008, 1012, 1014, 1016 may be stored locally on the respective computer and/or remotely, as appropriate. The database 1018 may be a relational database, such as Oracle 20i®, that is adapted to store, update, and retrieve data in response to SQL-formatted commands.

Figure 11:
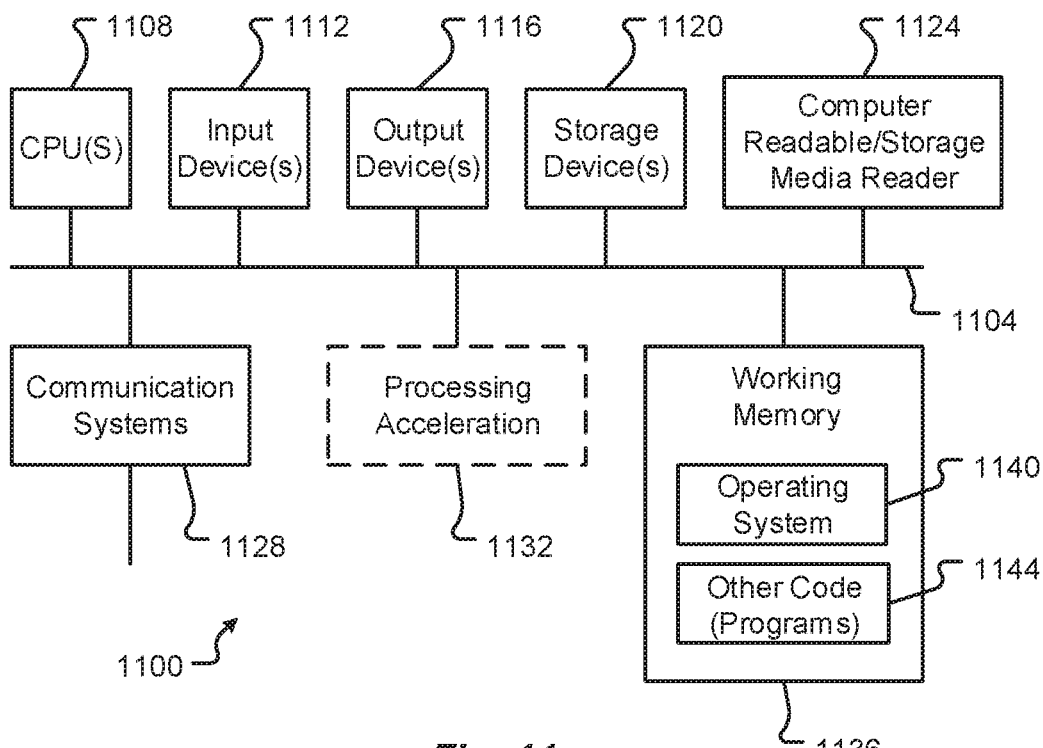
FIG. 11 is a block diagram of a computing device associated with one or more components described herein.

FIG. 11 illustrates one embodiment of a computer system 1100 upon which the servers, user computers, computing devices, or other systems or components described above may be deployed or executed. The computer system 1100 is shown comprising hardware elements that may be electrically coupled via a bus 1104. The hardware elements may include one or more central processing units (CPUs) 1108; one or more input devices 1112 (e.g., a mouse, a keyboard, etc.); and one or more output devices 1116 (e.g., a display device, a printer, etc.). The computer system 1100 may also include one or more storage devices 1120. By way of example, storage device(s) 1120 may be disk drives, optical storage devices, solid-state storage devices such as a random access memory ("RAM") and/or a read-only memory ("ROM"), which can be programmable, flash-updateable and/or the like.

The computer system 1100 may additionally include a computer-readable storage media reader 1124; a communications system 1128 (e.g., a modem, a network card (wireless or wired), an infra-red communication device, etc.); and working memory 1136, which may include RAM and ROM devices as described above. The computer system 1100 may also include a processing acceleration unit 1132, which can include a DSP, a special-purpose processor, and/or the like.

The computer-readable storage media reader 1124 can further be connected to a computer-readable storage medium, together (and, optionally, in combination with storage device(s) 1120) comprehensively representing remote, local, fixed, and/or removable storage devices plus storage media for temporarily and/or more permanently containing computer-readable information. The communications system 1128 may permit data to be exchanged with a network and/or any other computer described above with respect to the computer environments described herein. Moreover, as disclosed herein, the term "storage medium" may represent one or more devices for storing data, including read only memory (ROM), random access memory (RAM), magnetic RAM, core memory, magnetic disk storage mediums, optical storage mediums, flash memory devices and/or other machine readable mediums for storing information.

The computer system 1100 may also comprise software elements, shown as being currently located within a working memory 1136, including an operating system 1140 and/or other code 1144. It should be appreciated that alternate embodiments of a computer system 1100 may have numerous variations from that described above. For example, customized hardware might also be used and/or particular elements might be implemented in hardware, software (including portable software, such as applets), or both. Further, connection to other computing devices such as network input/output devices may be employed.

Examples of the processors 1108 as described herein may include, but are not limited to, at least one of Qualcomm® Snapdragon® 800 and 801, Qualcomm® Snapdragon® 620 and 615 with 4G LTE Integration and 64-bit computing, Apple® A7 processor with 64-bit architecture, Apple® M7 motion coprocessors, Samsung® Exynos® series, the Intel® Core™ family of processors, the Intel® Xeon® family of processors, the Intel® Atom™ family of processors, the Intel Itanium® family of processors, Intel® Core® i5-4670K and i7-4770K 22 nm Haswell, Intel® Core® i5-3570K 22 nm Ivy Bridge, the AMD® FX™ family of processors, AMD® FX-4300, FX-6300, and FX-8350 32 nm Vishera, AMD® Kaveri processors, Texas Instruments® Jacinto C6000™ automotive infotainment processors, Texas Instruments® OMAP™ automotive-grade mobile processors, ARM® Cortex™-M processors, ARM® Cortex-A and ARM926EJ-S™ processors, other industry-equivalent processors, and may perform computational functions using any known or future-developed standard, instruction set, libraries, and/or architecture.

Figure 12:
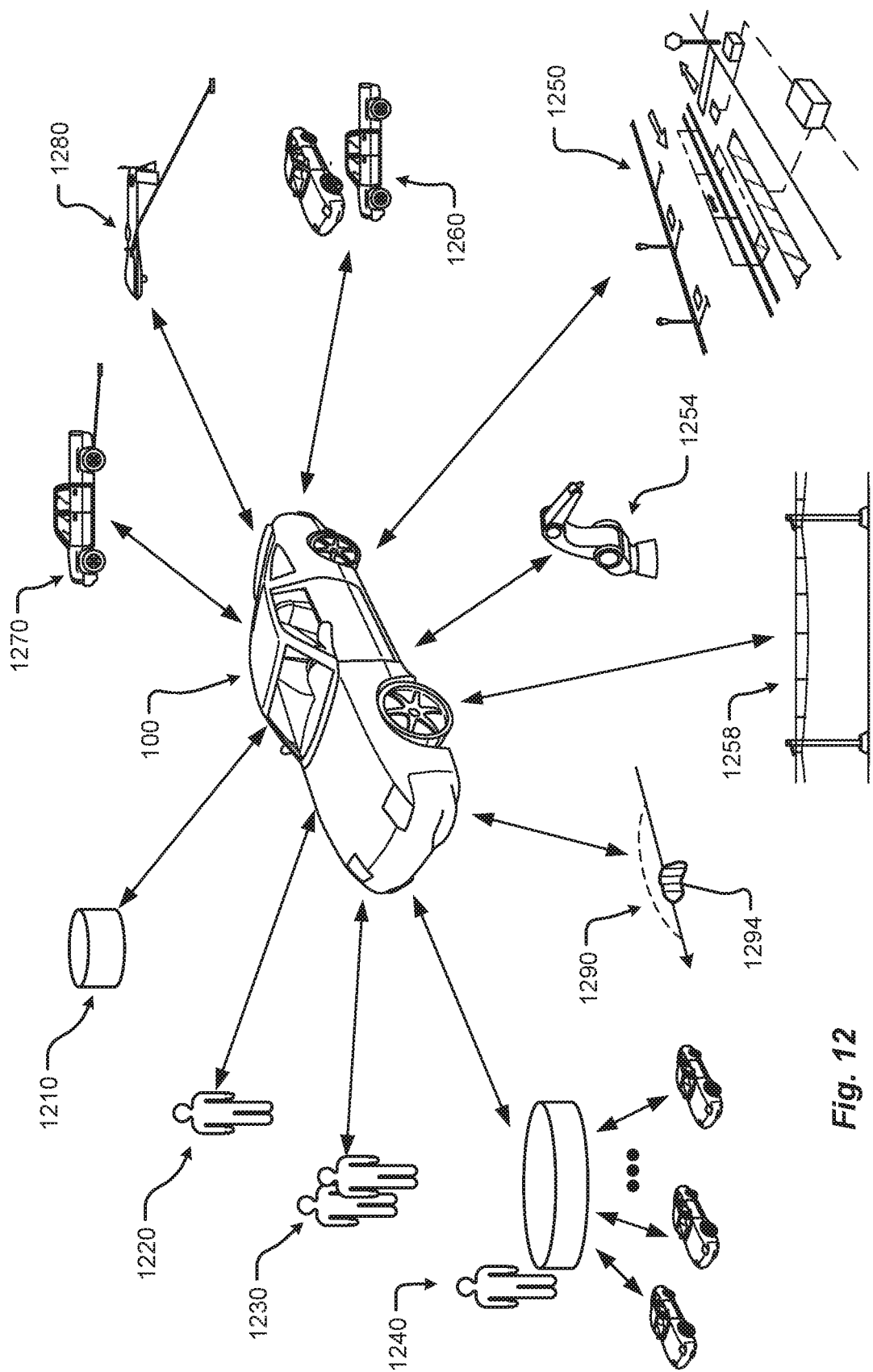
FIG. 12 shows a vehicle in an environment in accordance with embodiments of the present disclosure.

Referring to FIG. 12, the vehicle 100 is shown in a plurality of operational and/or charging environments. The vehicle 100 may operate in any one or more of the depicted environments in any combination. Other embodiments are possible but may not be depicted in FIG. 12. Generally, the vehicle 100 may operate in environments which enable charging of the vehicle 100 and/or operation of the vehicle 100. More specifically, the vehicle 100 may receive a charge via one or more means comprising emergency charging vehicle system 1270, aerial vehicle charging system 1280, roadway system 1250, robotic charging system 1254, and/or overhead charging system 1258. The vehicle 100 may interact and/or operate in an environment comprising one or more other roadway vehicles 1260. The vehicle 100 may engage with elements within the vehicle 100 comprising vehicle driver 1220, vehicle passengers 1230, and/or a vehicle database 1210. In one embodiment, vehicle database 1210 may not physically reside in the vehicle 100 and may instead be accessed remotely (e.g., by wireless communication, etc.), and as such, may reside in another location such as a residence or business location. The vehicle 100 may operate autonomously and/or semi-autonomously in an autonomous environment 1290 (here, depicted as a roadway environment presenting a roadway obstacle 1294 of which the vehicle 100 autonomously identifies and steers the vehicle 100 clear of the obstacle 1294). Furthermore, the vehicle 100 may engage with a remote operator system 1240, which may provide fleet management instructions or control.

In some embodiments, the vehicle 100 may be configured to receive charge via one or more compatible vehicle charging interfaces, such as one or more charging panels and/or interconnections. These compatible vehicle charging interfaces may be configured at one or more locations on, in, or about a vehicle 100. For instance, the locations may include locations on the vehicle 100 wherein charging may be received, via a vehicle roof 130, vehicle side 160 and vehicle lower or undercarriage 140.

FIG. 13A illustrates one embodiment of a first presentation of information on a user-adjusted (or occupant-adjusted) display device of a vehicle 100. FIG. 13A is the same as FIG. 4 except that FIG. 13A illustrates sensor(s) 1300 on either side of the heads-up display (HUD) 434 and a first presentation of information as items I1 to I6 on a display device of the vehicle 100, where the display device refers to the collection of the vehicle operational display 420, the one or more auxiliary displays 424, the heads-up display 434, the power management display 428, the input device 432, and/or other displays (mobile device displays) related to the vehicle 100. The information includes at least one of vehicle information about the vehicle and occupant information about the occupant of the vehicle 100. Examples of vehicle information include any information about the status or condition of the vehicle 100, such as vehicle speed, battery level, trip and/or overall mileage, car stereo settings, and the like. Examples of occupant information include any information about the status or condition of the occupants, such as skin temperature, alertness information, weight of the occupant, attention level, and the like. The first presentation of the information as items I1-I6 may be a default presentation of the information that is displayed each time the vehicle 100 is restarted. Items I1-I6 may be presented in the form of one or more widgets, one or more icons, one or more menus, one or more windows, one or more tabs, and the like.

The sensors 1300 are part of the sensor loads 816 discussed with respect to FIG. 8 and are managed by the sensor connectivity manager 966 discussed with reference to FIG. 9. According to one embodiment, the controller/microprocessor 920 automatically adjusts the display device of the vehicle 100 based on output received from the sensors 1300. Example operations of the controller/microprocessor 920 are discussed in more detail below with reference to FIGS. 14 and 15.

In one embodiment, the sensors 1300 monitor conditions of the occupants of the vehicle 100. Thus, each sensor 1300 may include one or more types of devices to assist with monitoring the condition of the occupants. For example, the sensors 1300 may include one or more cameras, such as infrared/near-infrared cameras (or depth cameras) used for eye tracking and/or gesture tracking. Such cameras may operate according to time-of-flight principles to achieve pupil detection and/or gesture detection. For example, a light source of the sensor 1300 (or associated with the sensor 1300) emits light (e.g., infrared light) toward an interior of the vehicle 100. Light emitted from the light source is then reflected by objects (including occupants) within the interior vehicle and the reflected light is sensed by individual pixels of a camera of the sensor 1300. Based on time-of-flight principles (i.e., a time taken for the light emitted from the light source to reflect off on an object and then be sensed by the pixels of the camera), the controller/microprocessor 920 generates a depth map (where each pixel is assigned a depth value based on the elapsed time between the light source emitting light and the camera receiving thee reflected light), which is a three-dimensional representation of the interior of the vehicle 100 that is within the camera's range. For gesture tracking, the ongoing generation of the depth map is analyzed by the controller/microprocessor 920 to track the gestures of the occupants. For eye tracking, the controller/microprocessor 920 analyzes the reflected light from pupils of the eyes (e.g., light reflected from the corneas) to detect eye rotations. It should be understood that example embodiments are not limited to the above described method for gesture and eye tracking, and that other known methods may be used.

Other types and locations of sensors 1300 for monitoring conditions of occupants include vibration sensors (e.g., accelerometers built in to the seats of the vehicle 100) for monitoring occupant movement, temperature sensors for monitoring skin and/or ambient temperature, ultrasonic sensors configured to detect movement in an interior 150 of the vehicle 100, pressure sensors configured to detect ambient pressure conditions in the interior 150 of the vehicle 100, etc., and/or combinations thereof. It should be understood that a number, type, and location of the sensors 1300 are not limited to the options shown in FIG. 13A and may vary according to design parameters, such as a condition to be monitored and/or an anticipated location of the occupant being monitored. Thus, additional sensors 1300 may be located in parts of the interior 150 of the vehicle 100 not specifically illustrated in FIG. 13A.

FIG. 13B illustrates one embodiment of a second presentation of information on a user-adjusted (or occupant-adjusted) display device of a vehicle 100. Elements in FIG. 13B are the same as FIG. 13A except that FIG. 13B illustrates a second presentation of information as items I1 to I7 on a display device on the vehicle 100. Comparing the first presentation of the information in FIG. 13A and the second presentation of the information in FIG. 13B reveals that the second presentation of information includes additional information as item I7 as well as a re-rendering items I1 and I4, where locations of items I1 and I4 have swapped and item I4 has been resized (e.g., increased in size). In addition to changing sizes, locations, and content of the information (e.g., by adding and/or subtracting information items from the display device), it should be understood that the controller/microprocessor 920 may also change other properties of the information, such as a brightness of the items, a color of the items, and/or other visual settings associated with displaying information when rendering the second presentation.

Further, the controller/microprocessor 920 may associate a presentation of the information with a particular occupant, such as the driver, and store the association as a user profile in the memory/storage/cache 916. Upon determining that an occupant has an associated user profile indicating a preferred presentation of the information (e.g., based on output from at least one sensor 1300), the controller/microprocessor 920 may automatically switch to the presentation of the information indicated by the user profile. The sensors 1300 may include a biometric sensor (e.g., retina scanner, fingerprint scanner, etc.) to assist with identifying the occupant to select an associated user profile.

Figure 14:
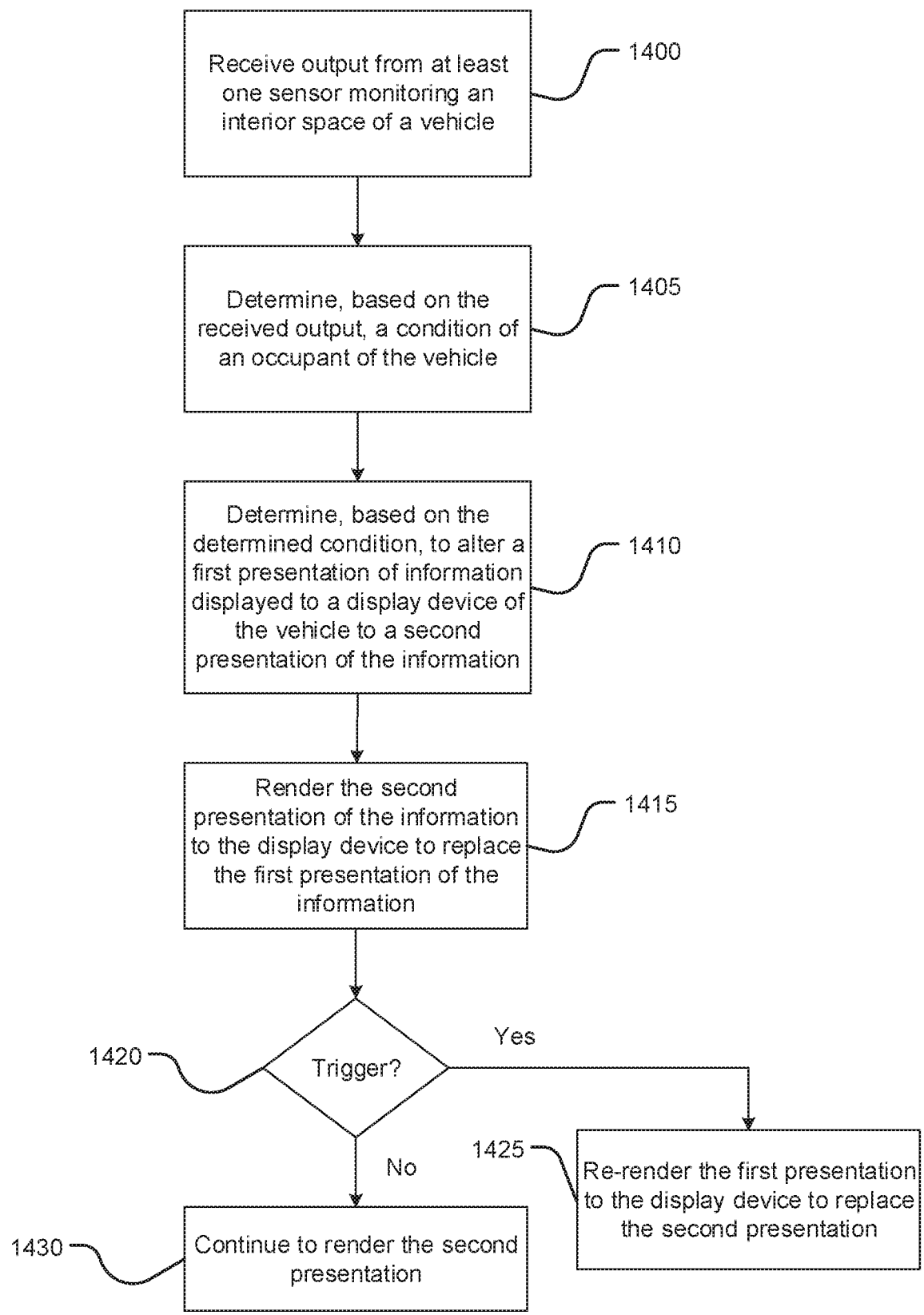
FIG. 14 illustrates example operations of the controller/microprocessor in FIG. 9 according to at least one embodiment.

The controller/microprocessor 920 may render the second presentation of the information shown in FIG. 13B to replace the first presentation of information shown in FIG. 13A for reasons discussed in more detail below with reference to FIGS. 14-16. FIG. 14 illustrates example operations of the controller/microprocessor 920 according to at least one embodiment. FIG. 14 is a flow diagram of a first method for rendering a second presentation of information to a display device to replace a first presentation of the information on the display device accordance with embodiments of the present disclosure. While a general order for the steps of the method is shown in FIG. 14, the method can include more or fewer steps or can arrange the order of the steps differently than those shown in FIG. 14. Generally, the method starts at operation 1400 and ends at operation 1430. The method can be executed as a set of computer-executable instructions executed by a computer system and encoded or stored on a computer readable medium. For example, the operations discussed with respect to FIG. 14 may be implemented by the controller/microprocessor 920 carrying instructions stored on a computer readable medium, such as the memory/storage/cache 916. Hereinafter, the FIG. 14 shall be explained with reference to the systems, components, assemblies, devices, user interfaces, environments, software, etc. described in conjunction with FIGS. 1-13B.

In operation 1400, the controller/microprocessor 920 receives output from at least one sensor 1300 monitoring an interior space 150 of a vehicle 100.

In operation 1405, the controller/microprocessor 920 determines, based on the received output, a condition of an occupant in the interior space 150 of the vehicle 100. For example, the controller/microprocessor 920 may use the output from the sensor 1300 as well as information from other vehicle sensors in sensor loads 816 to determine the condition of the occupant. FIG. 15 illustrates specific examples of conditions determined by the controller/microprocessor 920 based on output of the sensor 1300, and is discussed in more detail below.

In operation 1410, the controller/microprocessor 920 determines, based on the determined condition of the occupant, to alter a first presentation of information displayed to a display device (i.e., one or more of displays 420, 424, 434, 428, 432) of the vehicle 100 to a second presentation of the information displayed to the display device. As discussed with reference to FIGS. 13A and 13B, the information includes at least one of vehicle information about the vehicle 100 and occupant information about the occupant of the vehicle 100.

In operation 1415, the controller/microprocessor 920 renders the second presentation of the information to the display device of the vehicle 100 to replace the first presentation of the information displayed to the display device of the vehicle 100. The controller/microprocessor 920 may render the second presentation based on at least one of one or more preferences of the occupant, a recurrence frequency of the condition (e.g., a number of times the condition occurs over a desired time interval, for example, 5 minutes), and a priority level associated with the condition determined in operation 1405. The one or more preferences may include a size, a color, a brightness, a location, and/or other occupant defined visual settings for the information to be displayed. The condition may have an associated recurrence frequency threshold that should be met within a threshold amount of time before the controller/microprocessor 920 renders the second presentation to include information about the condition. Specific examples of operations 1405-1415 are described in more detail below with reference to FIGS. 15 and 16.

The priority level is based on at least a safety score associated with the condition. Thus, the priority level may be representative of how relevant the information to be displayed is to passenger safety (e.g., a drowsy driver). The safety score may be represented as a number that has an associated weight that assists with determining the priority level. For example, each condition detectable by the controller/microprocessor 920 may have an initial (or default) priority level that is assigned in advance or determined with the assistance of a raw priority score (RPS) in Equation 1. Additionally or alternatively, the controller/microprocessor 920 may continuously update the raw priority score for each condition using Equation 1.

$$RPS = \beta S \qquad \text{Equation 1}$$

In Equation 1, S is a value that represents the safety score associated with the condition and $\beta$ is the weight associated with the safety score. Value S and weight $\beta$ may be fixed and/or changeable design parameters based on user input and/or empirical evidence. The controller/microprocessor 920 may assign a priority level to a condition based on the raw priority score by evaluating the raw priority score against one or more thresholds associated with each priority level. The controller/microprocessor 920 may store the priority level in the memory/storage/cache 916. According to one embodiment, the controller/microprocessor 920 may store the priority level as part of a look-up-table (LUT) to assist with determining effects for rendering for the second presentation based on the priority level, one or more occupant preferences, and/or a recurrence frequency of the condition. FIG. 16 illustrates an example LUT and is discussed below in more detail.

Still referring to FIG. 14, the controller/microprocessor 920 may re-render the first presentation to the display device to replace the second presentation in response to a trigger. For example, in operation 1420, the controller/microprocessor 920 determines whether a trigger has occurred. If so, then the controller/microprocessor 920 performs operation 1425 to re-renders the first presentation to replace the second presentation on the display device. If not, then the controller/microprocessor continues to render the second presentation to the display device in operation 1430. The trigger may be a power reset event in which the display device loses, then regains power, for example, as a result of the vehicle 100 being shut-off and then restarted. In this case, the first presentation may be a default presentation of the information to the display device set by, for example, the manufacturer of the vehicle 100 and/or the user profile mentioned above. According to one embodiment, the trigger is tied to an elapsed time from the performance of operation 1415. For example, the controller/microprocessor 920 may re-render the first presentation if the elapsed time is over a desired threshold time, such as 5 minutes. The threshold time may be a design parameter set based on user input and/or empirical evidence. In another example, the controller/microprocessor 920 re-renders the first presentation after failing to detect any changes in the condition of the occupant within the threshold time. In some embodiments, the controller/microprocessor 920 may re-render the first presentation upon detecting a change in the driving, operating, or controlling, occupant associated with the vehicle 100. For instance, control may be transferred from one occupant to another in the vehicle 100. In one control-transfer scenario, an occupant may switch positions with another occupant in a controlling position (e.g., the driver's seat, etc.). In another control-transfer scenario, an occupant may transfer control of the vehicle 100 to another occupant in a different seat or area of the vehicle 100. In any event, a change in an occupant associated with a control of one or more operations of the vehicle 100 may trigger the re-rendering of the first presentation. Although not specifically described herein, it should be understood that additional triggers are within the scope of example embodiments.

Figure 15:
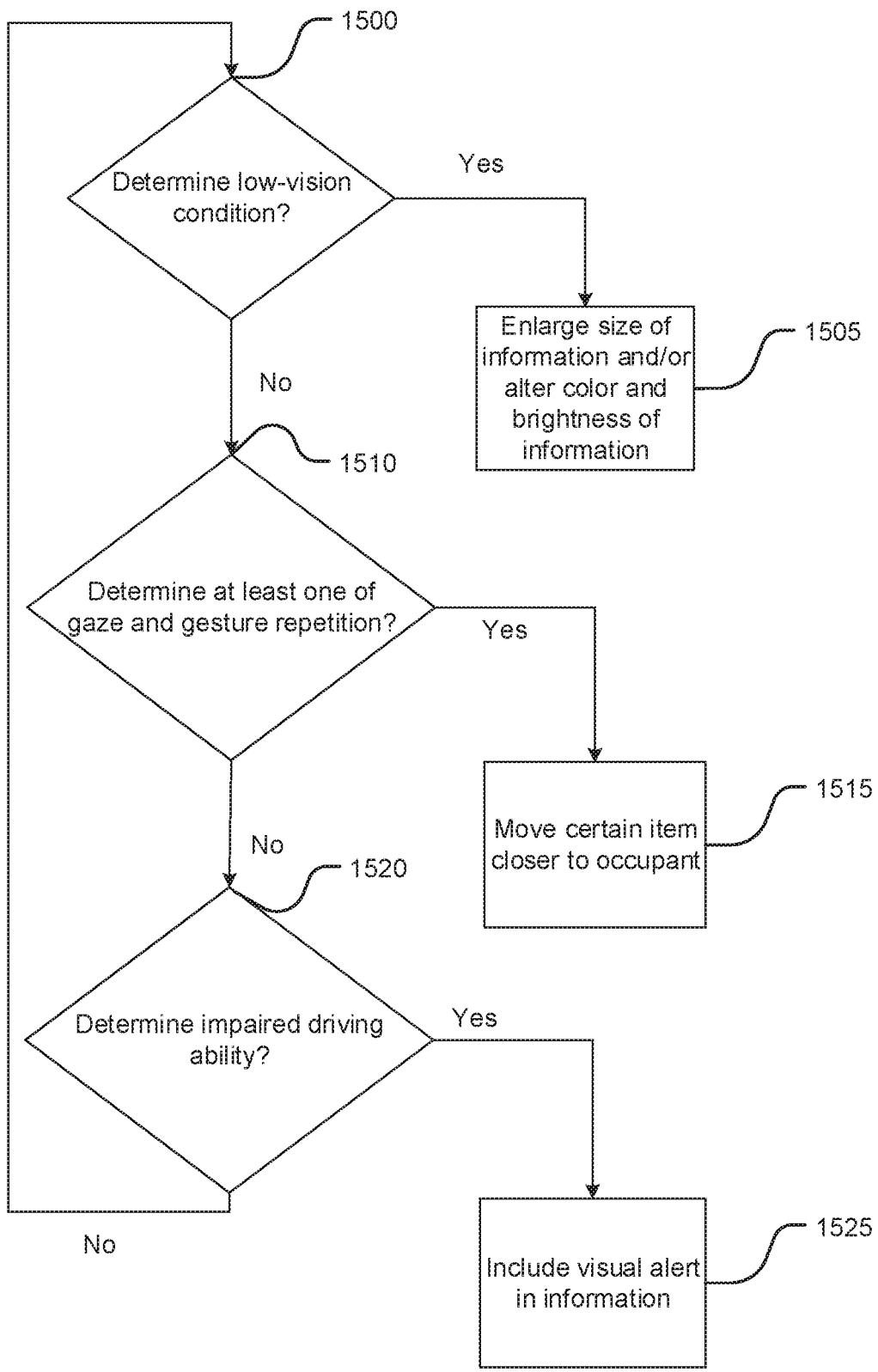
FIG. 15 illustrates example operations of the controller/microprocessor in FIG. 9 according to at least one embodiment.

FIG. 15 illustrates example operations of the controller/microprocessor 920 according to at least one embodiment. FIG. 15 is a flow diagram of a method for rendering a second presentation of information to a display device to replace a first presentation of the information on the display device accordance with embodiments of the present disclosure. FIG. 15 illustrates specific examples of conditions and second presentations mentioned in FIGS. 13A-14. While a general order for the steps of the method is shown in FIG. 15, the method can include more or fewer steps or can arrange the order of the steps differently than those shown in FIG. 15. Generally, the method starts at operation 1500 and ends at operation 1525. The method can be executed as a set of computer-executable instructions executed by a computer system and encoded or stored on a computer readable medium. For example, the operations discussed with respect to FIG. 15 may be implemented by the controller/microprocessor 920 carrying instructions stored on a computer readable medium, such as the memory/storage/cache 916. Hereinafter, the FIG. 15 shall be explained with reference to the systems, components, assemblies, devices, user interfaces, environments, software, etc. described in conjunction with FIGS. 1-14.

In operation 1500, the controller/microprocessor 920 determines whether the condition is determined to include that the occupant has low-vision. If so, the controller/microprocessor 920 performs operation 1505 to render the second presentation by at least one of i) increasing a size of the information on the display device, and ii) altering at least one of a color and a brightness of the information on the display device. For example, in FIG. 13B, item I2 has been enlarged on HUD 434 compared to item I2 in FIG. 13A. The low-vision condition may be determined for an occupant wearing glasses. In this case, the low-vision condition may be detectable by the controller/microprocessor 920 by sensing reflections from the occupant's glasses via output from the sensor 1300. In some cases, the low-vision condition of the occupant may be detected via at least one camera sensor identifying an optical accessory worn or used by the occupant while in the interior space 150 of the vehicle 100. In another example, the controller/microprocessor 920 may determine that the occupant has low-vision by using pupil detection to deduce that the occupant is squinting in the direction of the display device. In some embodiments, the occupant may be detected as being photo-sensitive. In this example, the controller/microprocessor 920 may receive sensor information identifying the occupant as squinting, wearing photo-sensitive glasses, or otherwise shielding the eyes from bright light conditions. Continuing this example, the bright light condition may be corroborated via at least one light sensor in the vehicle 100 as described above.

If the controller/microprocessor 920 does not determine a low-vision condition in operation 1500, the controller/microprocessor 920 performs operation 1510 to determine whether the condition includes that at least one of i) a gaze of the occupant is repeatedly toward a certain item of the information in the first presentation, and ii) repeated hand motions of the occupant are toward the certain item in the first presentation. If so, the controller/microprocessor 920 performs operation 1515 to render the second presentation by moving the certain item closer to the occupant on the display device. For example, if the occupant being monitored is the driver of the vehicle 100 and the controller/microprocessor determines that the driver is repeatedly gazing at the stereo display/controls represented by item I4, FIG. 13B shows moving item I4 closer to the driver by swapping locations with item I1. The controller/microprocessor 920 may determine i) and ii) by counting a number of repeated gazes and/or gestures (i.e., a recurrence frequency of the condition) determined by the controller/microprocessor 920 within a threshold amount of time, and comparing the number of repeated gazes and/or gestures to a threshold number. For example, as shown in FIG. 16, the controller/microprocessor 920 determines that a repeated gaze toward temperature controls occurs if output from the sensor 1300 indicates that the occupant has looked toward the temperature controls 3 times in 3 minutes. The threshold amount of time and threshold number may be design parameters set based on user input and/or empirical evidence.

If the controller/microprocessor 920 does not determine that the condition includes a repeated gaze or hand gesture in operation 1510 and the occupant being monitored is the driver of the vehicle 100, the controller/microprocessor 920 performs operation 1520 to determine whether the condition includes that the driver has impaired driving ability. If so, the controller/microprocessor 920 performs operation 1525 to render the second presentation by including a visual warning in the information. For example, item I7 in FIG. 13B may represent the visual warning. To determine that the driver has impaired driving ability, the controller/microprocessor 920 may process output of the sensor 1300 in addition to output from other vehicle sensors. For example, the controller/microprocessor 920 may use output of the sensor 1300 to determine that the driver's pupils are dilated, indicating a possibility of impairment. The controller/microprocessor 920 may use this information in combination with information from other vehicle sensors such as speed sensors, steering sensors, lane sensors, etc. to deduce that the driver may be impaired.

If the controller/microprocessor 920 does not determine impaired driving ability in operation 1520, the controller/microprocessor 920 returns to operation 1500.

In FIG. 15, it should be understood that the controller/microprocessor 920 may determine that multiple occupant conditions are occurring simultaneously, in which case the controller/microprocessor 920 may consult the priority level of each condition to determine an arrangement of the information for rendering the second presentation (see discussion of FIG. 16 for more detail).

FIG. 16 illustrates an example LUT that assists with determining effects for rendering for the second presentation based on the priority level of the condition, one or more occupant preferences associated with the condition, and/or a recurrence frequency of the condition.

FIG. 16 illustrates various conditions that may be determined by the controller/microprocessor 920 in accordance with the operations described in FIGS. 13A-15. The conditions include impaired driving, low-vision, repeated gaze toward temperature controls, repeated gesture toward stereo controls, and high or low skin temperature. As described with reference to FIG. 14, each of these conditions may have one or more of an associated safety score, a weight associated with the safety score, a raw priority score, a priority level, a recurrence frequency threshold to exceed within a threshold time, a presentation effect, and occupant preference(s). The safety score is representative of how relevant the information to be displayed is to occupant safety. For example, the more likely a condition is to have a negative impact on occupant safety, the higher the safety score. Thus, the condition of an impaired driver has a highest safety score of 10 and weight of 1.0 in FIG. 16, while the condition of high or low skin temperature of receives a lower safety score of 5 and weight 0.2 because the high or low skin temperature could be a result of ambient temperature making it is less likely to negatively impact occupant safety.

The LUT includes a raw priority score (RPS) for each condition and an associated priority level that is determined based on the RPS. In FIG. 16, a higher RPS receives a higher priority level such that the impaired driver condition receives a highest priority among the listed conditions. The LUT also includes presentation effects and occupant preferences that guide how to display the presentation effects. When the controller/microprocessor 920 determines that multiple occupant conditions are occurring simultaneously, the controller/microprocessor 920 may consult the priority level of each condition to determine an arrangement of the second presentation. In one embodiment, presentation effects of conditions with higher priority levels may receive priority over presentation effects of conditions with lower priority levels. For example, if the controller/microprocessor 920 determines that an impaired driver condition occurs simultaneously with a repeated gaze toward temperature controls condition (both of which indicate that something should be displayed in a primary viewing location on the display device, which is a location on the display device that is within the driver's immediate field of vision), the controller/microprocessor 920 will give preference to the higher priority condition and render the second presentation to display the alert in the primary viewing location (e.g., to display 420A) while maintaining the location of the temperature controls or moving the location of the temperature controls to a secondary viewing location (e.g., to display 420B).

It should be understood that example embodiments contemplate the possibility for updating safety scores, weights, and/or presentation effects based on user input and/or empirical evidence. For example, if the controller/microprocessor 920 determines, based on output from sensor 1300, that the occupant's skin temperature is particularly high or low (i.e., over or above a safety threshold) for the current ambient temperature so as to indicate a possibility of heat-exhaustion or hypothermia, then the controller/microprocessor 920 may increase (e.g., temporarily increase) one of the safety score and the weight for that condition so that a priority level of the condition also increases. The sudden increase in priority level may trigger additional presentation effects such as a visual warning in a primary viewing location to indicate that increased or decreased skin temperature has been detected. This may be particularly useful for monitoring the body temperature of occupants that are infants or pets.

It should be understood that every condition does not necessarily have an associated safety score, associated preferences, and/or an associated recurrence frequency, in which case the LUT includes only an initial or default values for those categories. It should be further understood that example embodiments are not limited to the conditions and presentations described with respect to FIGS. 13A-16, and that other conditions and presentations are within the scope of example embodiments.

In view of the above description, it should be understood that one or more sensors 1300 can observe or monitor the driver and/or passengers (or occupants) in a vehicle 100. From the observations and/or other information, a display device (e.g., the vehicle operational display 420, the one or more auxiliary displays 424, the heads-up display 434, the power management display 428, and/or the input device 432) may be adjusted automatically to assist the driver/passenger(s). For example, if the user is viewed as wearing glasses, one or more of the widgets forming the display may be increased in size or may change color or brightness. If the user is seen as changing the radio frequently, the radio controls may be positioned temporarily in a HUD to add in finding a radio station. Further, new widgets may be added when needed, such as, a temperature gauge for body temperature, etc.

Any of the steps, functions, and operations discussed herein can be performed continuously and automatically.

The exemplary systems and methods of this disclosure have been described in relation to vehicle systems and electric vehicles. However, to avoid unnecessarily obscuring the present disclosure, the preceding description omits a number of known structures and devices. This omission is not to be construed as a limitation of the scope of the claimed disclosure. Specific details are set forth to provide an understanding of the present disclosure. It should, however, be appreciated that the present disclosure may be practiced in a variety of ways beyond the specific detail set forth herein.

Furthermore, while the exemplary embodiments illustrated herein show the various components of the system collocated, certain components of the system can be located remotely, at distant portions of a distributed network, such as a LAN and/or the Internet, or within a dedicated system. Thus, it should be appreciated, that the components of the system can be combined into one or more devices, such as a server, communication device, or collocated on a particular node of a distributed network, such as an analog and/or digital telecommunications network, a packet-switched network, or a circuit-switched network. It will be appreciated from the preceding description, and for reasons of computational efficiency, that the components of the system can be arranged at any location within a distributed network of components without affecting the operation of the system.

Furthermore, it should be appreciated that the various links connecting the elements can be wired or wireless links, or any combination thereof, or any other known or later developed element(s) that is capable of supplying and/or communicating data to and from the connected elements. These wired or wireless links can also be secure links and may be capable of communicating encrypted information. Transmission media used as links, for example, can be any suitable carrier for electrical signals, including coaxial cables, copper wire, and fiber optics, and may take the form of acoustic or light waves, such as those generated during radio-wave and infra-red data communications.

While the flowcharts have been discussed and illustrated in relation to a particular sequence of events, it should be appreciated that changes, additions, and omissions to this sequence can occur without materially affecting the operation of the disclosed embodiments, configuration, and aspects.

A number of variations and modifications of the disclosure can be used. It would be possible to provide for some features of the disclosure without providing others.

In yet another embodiment, the systems and methods of this disclosure can be implemented in conjunction with a special purpose computer, a programmed microprocessor or microcontroller and peripheral integrated circuit element(s), an ASIC or other integrated circuit, a digital signal processor, a hard-wired electronic or logic circuit such as discrete element circuit, a programmable logic device or gate array such as PLD, PLA, FPGA, PAL, special purpose computer, any comparable means, or the like. In general, any device(s) or means capable of implementing the methodology illustrated herein can be used to implement the various aspects of this disclosure. Exemplary hardware that can be used for the present disclosure includes computers, handheld devices, telephones (e.g., cellular, Internet enabled, digital, analog, hybrids, and others), and other hardware known in the art. Some of these devices include processors (e.g., a single or multiple microprocessors), memory, nonvolatile storage, input devices, and output devices. Furthermore, alternative software implementations including, but not limited to, distributed processing or component/object distributed processing, parallel processing, or virtual machine processing can also be constructed to implement the methods described herein.

In yet another embodiment, the disclosed methods may be readily implemented in conjunction with software using object or object-oriented software development environments that provide portable source code that can be used on a variety of computer or workstation platforms. Alternatively, the disclosed system may be implemented partially or fully in hardware using standard logic circuits or VLSI design. Whether software or hardware is used to implement the systems in accordance with this disclosure is dependent on the speed and/or efficiency requirements of the system, the particular function, and the particular software or hardware systems or microprocessor or microcomputer systems being utilized.

In yet another embodiment, the disclosed methods may be partially implemented in software that can be stored on a storage medium, executed on programmed general-purpose computer with the cooperation of a controller and memory, a special purpose computer, a microprocessor, or the like. In these instances, the systems and methods of this disclosure can be implemented as a program embedded on a personal computer such as an applet, JAVA® or CGI script, as a resource residing on a server or computer workstation, as a routine embedded in a dedicated measurement system, system component, or the like. The system can also be implemented by physically incorporating the system and/or method into a software and/or hardware system.

Although the present disclosure describes components and functions implemented in the embodiments with reference to particular standards and protocols, the disclosure is not limited to such standards and protocols. Other similar standards and protocols not mentioned herein are in existence and are considered to be included in the present disclosure. Moreover, the standards and protocols mentioned herein and other similar standards and protocols not mentioned herein are periodically superseded by faster or more effective equivalents having essentially the same functions. Such replacement standards and protocols having the same functions are considered equivalents included in the present disclosure.

The present disclosure, in various embodiments, configurations, and aspects, includes components, methods, processes, systems and/or apparatus substantially as depicted and described herein, including various embodiments, subcombinations, and subsets thereof. Those of skill in the art will understand how to make and use the systems and methods disclosed herein after understanding the present disclosure. The present disclosure, in various embodiments, configurations, and aspects, includes providing devices and processes in the absence of items not depicted and/or described herein or in various embodiments, configurations, or aspects hereof, including in the absence of such items as may have been used in previous devices or processes, e.g., for improving performance, achieving ease, and/or reducing cost of implementation.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments, configurations, or aspects for the purpose of streamlining the disclosure. The features of the embodiments, configurations, or aspects of the disclosure may be combined in alternate embodiments, configurations, or aspects other than those discussed above. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment, configuration, or aspect. Thus, the following claims are hereby incorporated into this Detailed Description, with each claim standing on its own as a separate preferred embodiment of the disclosure.

Moreover, though the description of the disclosure has included description of one or more embodiments, configurations, or aspects and certain variations and modifications, other variations, combinations, and modifications are within the scope of the disclosure, e.g., as may be within the skill and knowledge of those in the art, after understanding the present disclosure. It is intended to obtain rights, which include alternative embodiments, configurations, or aspects to the extent permitted, including alternate, interchangeable and/or equivalent structures, functions, ranges, or steps to those claimed, whether or not such alternate, interchangeable and/or equivalent structures, functions, ranges, or steps are disclosed herein, and without intending to publicly dedicate any patentable subject matter.

Embodiments include a device comprising a microprocessor and a computer readable medium coupled to the microprocessor. The computer readable medium comprises instructions stored thereon that cause the microprocessor to receive output from at least one sensor monitoring an interior space of a vehicle, and determine, based on the received output, a condition of an occupant in the interior space of the vehicle. The instructions cause the microprocessor to determine, based on the determined condition of the occupant, to alter a first presentation of information displayed to a display device of the vehicle to a second presentation of the information displayed to the display device. The instructions cause the microprocessor to render the second presentation of the information to the display device of the vehicle to replace the first presentation of the information displayed to the display device of the vehicle.

Aspects of the above device include that the information includes at least one of vehicle information about the vehicle and occupant information about the occupant of the vehicle.

Aspects of the above device include instructions to cause the microprocessor to render the second presentation based on at least one of one or more preferences of the occupant, a recurrence frequency of the condition, and a priority level associated with the condition.

Aspects of the above device include that the priority level is based on at least a safety score associated with the condition.

Aspects of the above device include instructions that cause the microprocessor to render the second presentation based on at least one of the one or more preferences of the occupant, the recurrence frequency of the condition, and the priority level associated with the condition by changing at least one of a location, a size, a brightness, and a color of at least one item of the information on the display device.

Aspects of the above device include that if the condition is determined to include that the occupant has low-vision, the instructions cause the microprocessor to render the second presentation by at least one of i) increasing a size of the information on the display device, and ii) altering at least one of a color and a brightness of the information on the display device.

Aspects of the above device include that if the condition is determined to include that at least one of i) a gaze of the occupant is repeatedly toward a certain item of the information in the first presentation, and ii) repeated hand motions of the occupant are toward the certain item in the first presentation, the instructions cause the microprocessor to render the second presentation by moving the certain item closer to the occupant on the display device.

Aspects of the above device include that if the occupant is a driver of the vehicle and the condition is determined to include that the driver has impaired driving ability, the instructions cause the microprocessor to render the second presentation by including a visual warning in the information.

Aspects of the above device include instructions that cause the microprocessor to re-render the first presentation to the display device to replace the second presentation in response to a trigger event.

Aspects of the above device include that the first presentation is a default presentation of the information.

Aspects of the above device include instructions that cause the microprocessor to render the information in the first presentation and the second presentation via at least one widget.

Aspects of the above device include the at least one sensor.

Embodiments include a method that comprises receiving output from at least one sensor monitoring an interior space of a vehicle, and determining, based on the received output, a condition of an occupant in the interior space of the vehicle. The method includes determining, based on the determined condition of the occupant, to alter a first presentation of information displayed to a display device of the vehicle to a second presentation of the information displayed to the display device. The method includes rendering the second presentation of the information to the display device of the vehicle to replace the first presentation of the information displayed to the display device of the vehicle.

Aspects of the above method include that the information includes at least one of vehicle information about the vehicle and occupant information about the occupant of the vehicle.

Aspects of the above method include that the second presentation is based on at least one of one or more preferences of the occupant, a recurrence frequency of the condition, and a priority level associated with the condition by changing at least one of a location, a size, a brightness, and a color of at least one item of the information on the display device.

Aspects of the above method include that if the condition is determined to include that the occupant has low-vision, the rendering renders the second presentation by at least one of i) increasing a size of the information on the display device, and ii) altering at least one of a color and a brightness of the information on the display device.

Aspects of the above method include that if the condition is determined to include that at least one of i) a gaze of the occupant is repeatedly toward a certain item of the information in the first presentation, and ii) repeated hand motions of the occupant are toward the certain item in the first presentation, the rendering renders the second presentation by moving the certain item closer to the occupant on the display device.

Aspects of the above method include that if the occupant is a driver of the vehicle and the condition is determined to include that the driver has impaired driving ability, the rendering renders the second presentation by including a visual warning in the information.

Embodiments include a vehicle that comprises at least one sensor, a microprocessor coupled to the at least one sensor, and a computer readable medium coupled to the microprocessor. The computer readable medium comprises instructions stored thereon that cause the microprocessor to receive output from at least one sensor monitoring an interior space of a vehicle, and determine, based on the received output, a condition of an occupant in the interior space of the vehicle. The instructions case the microprocessor to determine, based on the determined condition of the occupant, to alter a first presentation of information displayed to a display device of the vehicle to a second presentation of the information displayed to the display device. The instructions cause the microprocessor to render the second presentation of the information to the display device of the vehicle to replace the first presentation of the information displayed to the display device of the vehicle.

Aspects of the vehicle include that if the instructions cause the microprocessor to render the second presentation based on at least one of one or more preferences of the occupant, a recurrence frequency of the condition, and a priority level associated with the condition by changing at least one of a location, a size, a brightness, and a color of at least one item of the information on the display device.

Any one or more of the aspects/embodiments as substantially disclosed herein.

Any one or more of the aspects/embodiments as substantially disclosed herein optionally in combination with any one or more other aspects/embodiments as substantially disclosed herein.

One or means adapted to perform any one or more of the above aspects/embodiments as substantially disclosed herein.

The phrases "at least one," "one or more," "or," and "and/or" are open-ended expressions that are both conjunctive and disjunctive in operation. For example, each of the expressions "at least one of A, B and C," "at least one of A, B, or C," "one or more of A, B, and C," "one or more of A, B, or C," "A, B, and/or C," and "A, B, or C" means A alone, B alone, C alone, A and B together, A and C together, B and C together, or A, B and C together.

The term "a" or "an" entity refers to one or more of that entity. As such, the terms "a" (or "an"), "one or more," and "at least one" can be used interchangeably herein. It is also to be noted that the terms "comprising," "including," and "having" can be used interchangeably.

The term "automatic" and variations thereof, as used herein, refers to any process or operation, which is typically continuous or semi-continuous, done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material."

Aspects of the present disclosure may take the form of an embodiment that is entirely hardware, an embodiment that is entirely software (including firmware, resident software, micro-code, etc.) or an embodiment combining software and hardware aspects that may all generally be referred to herein as a "circuit," "module," or "system." Any combination of one or more computer-readable medium(s) may be utilized. The computer-readable medium may be a computer-readable signal medium or a computer-readable storage medium.

A computer-readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer-readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer-readable storage medium may be any tangible medium that can contain or store a program for use by or in connection with an instruction execution system, apparatus, or device.

A computer-readable signal medium may include a propagated data signal with computer-readable program code embodied therein, for example, in baseband or as part of a carrier wave. Such a propagated signal may take any of a variety of forms, including, but not limited to, electro-magnetic, optical, or any suitable combination thereof. A computer-readable signal medium may be any computer-readable medium that is not a computer-readable storage medium and that can communicate, propagate, or transport a program for use by or in connection with an instruction execution system, apparatus, or device. Program code embodied on a computer-readable medium may be transmitted using any appropriate medium, including, but not limited to, wireless, wireline, optical fiber cable, RF, etc., or any suitable combination of the foregoing.

The terms "determine," "calculate," "compute," and variations thereof, as used herein, are used interchangeably and include any type of methodology, process, mathematical operation or technique.

The term "electric vehicle" (EV), also referred to herein as an electric drive vehicle, may use one or more electric motors or traction motors for propulsion. An electric vehicle may be powered through a collector system by electricity from off-vehicle sources, or may be self-contained with a battery or generator to convert fuel to electricity. An electric vehicle generally includes a rechargeable electricity storage system (RESS) (also called Full Electric Vehicles (FEV)). Power storage methods may include: chemical energy stored on the vehicle in on-board batteries (e.g., battery electric vehicle or BEV), on board kinetic energy storage (e.g., flywheels), and/or static energy (e.g., by on-board double-layer capacitors). Batteries, electric double-layer capacitors, and flywheel energy storage may be forms of rechargeable on-board electrical storage.

The term "hybrid electric vehicle" refers to a vehicle that may combine a conventional (usually fossil fuel-powered) powertrain with some form of electric propulsion. Most hybrid electric vehicles combine a conventional internal combustion engine (ICE) propulsion system with an electric propulsion system (hybrid vehicle drivetrain). In parallel hybrids, the ICE and the electric motor are both connected to the mechanical transmission and can simultaneously transmit power to drive the wheels, usually through a conventional transmission. In series hybrids, only the electric motor drives the drivetrain, and a smaller ICE works as a generator to power the electric motor or to recharge the batteries. Power-split hybrids combine series and parallel characteristics. A full hybrid, sometimes also called a strong hybrid, is a vehicle that can run on just the engine, just the batteries, or a combination of both. A mid hybrid is a vehicle that cannot be driven solely on its electric motor, because the electric motor does not have enough power to propel the vehicle on its own.

The term "rechargeable electric vehicle" or "REV" refers to a vehicle with on board rechargeable energy storage, including electric vehicles and hybrid electric vehicles.

What is claimed is:

1. A vehicle, comprising:
a camera to monitor an interior of the vehicle;
a microprocessor; and a computer readable medium coupled to the microprocessor and comprising instructions stored thereon that cause the microprocessor to:

render a first presentation of selected information on a display device of the vehicle, the selected information in the first presentation including a certain item in a first location on the display device;

identify, from output of the camera, a temporary condition including a counted number of hand motions of an operator of the vehicle toward the certain item in the first presentation;

determine a priority level associated with the certain item, a magnitude of the priority level being related to a level of occupant safety;

automatically determine, when the priority level exceeds a threshold priority level and when the counted number of hand motions exceeds a threshold count of hand motions, to alter the first presentation of the selected information currently displayed by the display device of the vehicle to a different second presentation of the selected information to be displayed by the display device, the second presentation being associated with a higher degree of occupant safety than the first presentation and including at least the certain item of the selected information in a second location on the display device that is closer to the operator compared to the first location;

automatically render, in response to the determination to alter the first presentation to the second presentation, the second presentation to the display device of the vehicle to replace the display of the first presentation; and upon occurrence of a selected triggering event associated with the identified temporary condition, automatically re-render the first presentation to the display device of the vehicle to replace the second presentation so that the certain item of information returns to the first location on the display device.

2. The vehicle of claim 1, wherein the microprocessor generates, from the camera output, a three-dimensional representation of the interior of the vehicle including one or more vehicle occupants, the one or more vehicle occupants comprising the operator, and identifies the temporary condition from the three-dimensional representation and wherein the microprocessor assigns each pixel of the three-dimensional representation a depth value based on an elapsed time between a light source emitting light and the camera receiving the light after reflection by the operator.

3. The vehicle of claim 2, wherein the microprocessor analyzes the light reflected from a pupil or cornea or of an occupant to detect a rotation of the eye of the operator.

4. The vehicle of claim 1, wherein the microprocessor determines a safety score for the identified temporary condition, the priority level being based on at least the safety score associated with the identified temporary condition, and a weighting factor associated with the safety score and determines the priority level based on the safety score and associated weighting factor, and wherein the microprocessor temporarily increases the safety score in response to a change in the identified temporary condition, the change being related to reduced safety of the one or more vehicle occupants.

5. The vehicle of claim 3, wherein the identified temporary condition includes a skin temperature of the one or more occupants, wherein the change relates to the skin temperature being above a first temperature or below a second temperature, wherein the microprocessor determines the first temperature and the second temperature based on a current ambient temperature.

6. The vehicle of claim 1, wherein the selected triggering event is a determination by the microprocessor that the identified temporary condition has remained unchanged over a selected threshold time interval or the operator is no longer operating the vehicle, and wherein the first and second presentations differ in one or more of a size of the selected information displayed, a color of the selected information displayed, and a brightness of the selected information displayed.

7. The vehicle of claim 1, wherein a third presentation of the selected information has an associated third priority level and second temporary condition, wherein the second presentation has an associated second priority level and is associated with the identified temporary condition, wherein the second priority level is higher than the third priority level, wherein the microprocessor identifies that the second temporary condition is occurring concurrently with the identified temporary condition, and wherein the microprocessor uses the higher second priority level of the identified temporary condition rather than the lower third priority level of the third temporary condition in selecting the second presentation.

8. The vehicle of claim 1, wherein the display device includes a plurality of vehicle operational display portions that are physically separated from one another, and wherein the selected information in the second presentation appears in a different vehicle operational display portion than in the first presentation.

9. A method for operating a vehicle, comprising:

providing a vehicle comprising a camera to monitor an interior of the vehicle, a microprocessor, and a computer readable medium coupled to the microprocessor;

rendering, by the microprocessor, a first presentation of selected information on a display device of the vehicle, the selected information in the first presentation including a certain item in a first location on the display device;

identifying, by the microprocessor and from output of the camera, a temporary condition including a counted number of hand motions of an operator of the vehicle toward the certain item in the first presentation;

determining, by the microprocessor, a priority level associated with the certain item, a magnitude of the priority level being related to a level of occupant safety;

automatically determining, by the microprocessor and when the priority level exceeds a threshold priority level and when the counted number of hand motions exceeds a threshold count of hand motions, to alter the first presentation of the selected information currently displayed by the display device of the vehicle to a different second presentation of the selected information to be displayed by the display device, the second presentation, for the identified temporary condition, being associated with a higher degree of occupant safety than the first presentation and including at least the certain item of the selected information in a second location on the display device that is closer to the operator compared to the first location;

automatically rendering, by the microprocessor, in response to the determination to alter the first presentation to the second presentation, the second presentation to the display device of the vehicle to replace the display of the first presentation;

detecting, by the microprocessor, that a selected triggering event associated with the identified temporary condition has occurred; and in response to the detecting, automatically re-rendering, by the microprocessor, the first presentation to the display device of the vehicle to replace the second presentation so that the certain item of information returns to the first location on the display device.

10. The method of claim 9, wherein the microprocessor generates, from the camera output, a three-dimensional representation of the interior of the vehicle including one or more vehicle occupants, the one or more vehicle occupants comprising the operator, and identifies the temporary condition from the three-dimensional representation and wherein the microprocessor assigns each pixel of the three-dimensional representation a depth value based on an elapsed time between a light source emitting light and the camera receiving the light after reflection by the operator.

11. The method of claim 10, wherein the microprocessor analyzes the light reflected from a pupil or cornea or of an occupant to detect a rotation of the eye of the operator.

12. The method of claim 9, wherein the microprocessor determines a safety score for the identified temporary condition, the priority level being based on at least the safety score associated with the identified temporary condition, and a weighting factor associated with the safety score and determines the priority level based on the safety score and associated weighting factor.

13. The method of claim 12, wherein the microprocessor assigns the priority level to the identified temporary condition by evaluating the priority score against one or more thresholds.

14. The method of claim 9, wherein the selected triggering event is a determination by the microprocessor that the identified temporary condition has remained unchanged over a selected threshold time interval or the operator is no longer operating the vehicle, and wherein the first and second presentations differ in one or more of a size of the selected information displayed, a color of the selected information displayed, and a brightness of the selected information displayed.

15. The method of claim 9, wherein a third presentation of the selected information has an associated third priority level and second temporary condition, wherein the second presentation has an associated second priority level and is associated with the identified temporary condition, wherein the second priority level is higher than the third priority level, wherein the microprocessor identifies that the second temporary condition is occurring concurrently with the identified temporary condition, and wherein the microprocessor uses the higher second priority level of the identified temporary condition rather than the lower third priority level of the third temporary condition in selecting the second presentation.

16. A method for operating a vehicle, comprising:
providing a vehicle comprising a camera to monitor an interior of the vehicle, a microprocessor, and a computer readable medium coupled to the microprocessor;

rendering, by the microprocessor, a first presentation of selected information on a display device of the vehicle, the selected information in the first presentation including a certain item in a first location on the display device;

identifying, by the microprocessor and from output of the camera, a temporary condition including a counted number of hand motions of an operator of the vehicle toward the certain item in the first presentation;

determining, by the microprocessor, a priority level associated with the certain item, a magnitude of the priority level being related to a level of occupant safety;

automatically determining, by the microprocessor and when the priority level exceeds a threshold priority level and when the counted number of hand motions exceeds a threshold count of hand motions within a threshold amount of time, to alter the first presentation of the selected information currently displayed by the display device of the vehicle to a different second presentation of the selected information to be displayed by the display device, the second presentation, for the identified temporary condition, having a higher degree of occupant safety than the first presentation, wherein the certain item of the selected information on the display device is in a different location in the second presentation such that the selected information is closer to the operator in the second presentation than in the first presentation;

automatically rendering, by the microprocessor, in response to the determination to alter the first presentation to the second presentation, the second presentation to the display device of the vehicle to replace the display of the first presentation;

detecting, by the microprocessor, that a selected triggering event associated with the identified temporary condition has occurred; and in response to the detecting, automatically re-rendering, by the microprocessor, the first presentation to the display device of the vehicle to replace the second presentation so that the certain item of information returns to the first location on the display device, wherein the selected triggering event is a determination by the microprocessor that the operator is no longer operating the vehicle.

17. The method of claim 16, wherein a third presentation of the selected information has an associated third priority level and second temporary condition, wherein the second presentation has an associated second priority level and is associated with the identified temporary condition, wherein the second priority level is higher than the third priority level, wherein the microprocessor identifies that the second temporary condition is occurring concurrently with the identified temporary condition, and wherein the microprocessor uses the higher second priority level of the identified temporary condition rather than the lower third priority level of the third temporary condition in selecting the second presentation.

* * * * *

UNITED STATES PATENT AND TRADEMARK OFFICE
CERTIFICATE OF CORRECTION

PATENT NO. : 10,699,326 B2  
APPLICATION NO. : 15/393097  
DATED : June 30, 2020  
INVENTOR(S) : Christopher P. Ricci Page 1 of 1

It is certified that error appears in the above-identified patent and that said Letters Patent is hereby corrected as shown below:

In the Claims

Claim 5, Column 33, Line 64, delete "claim 3" and insert --claim 4-- therein.

Signed and Sealed this  
Twenty-fifth Day of August, 2020

Andrei Iancu  
*Director of the United States Patent and Trademark Office*